(12) United States Patent
Bibian et al.

(10) Patent No.: US 11,109,789 B1
(45) Date of Patent: Sep. 7, 2021

(54) FIELD DEPLOYABLE BRAIN MONITOR AND METHOD

(71) Applicants: Stéphane Bibian, Cleveland Heights, OH (US); Tatjana Zikov, Cleveland Heights, OH (US); Sankar Barua, Stow, OH (US)

(72) Inventors: Stéphane Bibian, Cleveland Heights, OH (US); Tatjana Zikov, Cleveland Heights, OH (US); Sankar Barua, Stow, OH (US)

(73) Assignee: NeuroWave Systems Inc., Cleveland, OH (US)

( * ) Notice: Subject to any disclaimer, the term of this patent is extended or adjusted under 35 U.S.C. 154(b) by 1000 days.

(21) Appl. No.: 13/962,533

(22) Filed: Aug. 8, 2013

Related U.S. Application Data

(60) Provisional application No. 61/680,888, filed on Aug. 8, 2012.

(51) Int. Cl.
  *A61B 5/372* (2021.01)
  *A61B 5/291* (2021.01)

(52) U.S. Cl.
  CPC .................................. *A61B 5/291* (2021.01)

(58) Field of Classification Search
  CPC ............................ A61B 5/0476; A61B 5/0482
  See application file for complete search history.

(56) References Cited

U.S. PATENT DOCUMENTS

| | | | | |
|---|---|---|---|---|
| 4,674,512 A | * | 6/1987 | Rolf | H01B 1/20 600/391 |
| 5,273,037 A | * | 12/1993 | Itil | A61B 5/0478 600/383 |
| 5,817,029 A | * | 10/1998 | Gevins | A61B 5/0478 600/544 |
| 2002/0173729 A1 | * | 11/2002 | Viertio-Oja | A61B 5/0476 600/544 |
| 2004/0193068 A1 | * | 9/2004 | Burton | A61B 5/0476 600/544 |
| 2008/0091090 A1 | * | 4/2008 | Guillory | A61B 5/0478 600/301 |
| 2008/0139894 A1 | * | 6/2008 | Szydlo-Moore | A61B 5/0002 600/300 |
| 2009/0024044 A1 | * | 1/2009 | Virtanen | A61B 5/0205 600/509 |

(Continued)

OTHER PUBLICATIONS

"Residual brain dysfunction observed one year post-mild traumatic brain injury: Combined EEG and balance study" by Slobounov et al., Clinical Neurophysiology, V. 123, Iss. 9, pp. 1755-1761, 2012.*

*Primary Examiner* — Etsub D Berhanu
(74) *Attorney, Agent, or Firm* — Brian Kolkowski

(57) ABSTRACT

A system and method for using electroencephalographic (EEG) signals to monitor brain function, preferably detect occurrence of traumatic brain injury (TBI) to screen, assess, and potentially provide mitigating treatment to improve short and long term adverse outcomes of mild TBI (mTBI) and TBI. The system and method provides a readily available tool to assist in accurate and objective assessment of subjects with TBI, immediately at the point of injury (POI), during transportation, or upon arrival at a care facility, that preferably is applicable without advanced training or expertise.

10 Claims, 56 Drawing Sheets

(56) References Cited

U.S. PATENT DOCUMENTS

| | | | |
|---|---|---|---|
| 2009/0054750 A1* | 2/2009 | Jennewine | A61B 5/14532 600/316 |
| 2009/0076336 A1* | 3/2009 | Mazar | A61B 5/0402 600/300 |
| 2009/0247894 A1* | 10/2009 | Causevic | A61B 5/0478 600/544 |
| 2010/0241064 A1* | 9/2010 | Puri | A61M 5/1452 604/66 |
| 2011/0077473 A1* | 3/2011 | Lisogurski | A61B 5/14551 600/301 |
| 2011/0130675 A1* | 6/2011 | Bibian | A61B 5/0476 600/544 |
| 2012/0041330 A1* | 2/2012 | Prichep | A61B 5/0478 600/544 |
| 2012/0277548 A1* | 11/2012 | Burton | A61B 5/0205 600/301 |
| 2013/0109995 A1* | 5/2013 | Rothman | G06K 9/6217 600/544 |
| 2013/0184603 A1* | 7/2013 | Rothman | A61B 5/7264 600/544 |
| 2013/0281797 A1* | 10/2013 | Sabesan | A61B 5/0205 600/301 |
| 2013/0331660 A1* | 12/2013 | Al-Ali | A61B 5/0476 600/301 |

* cited by examiner

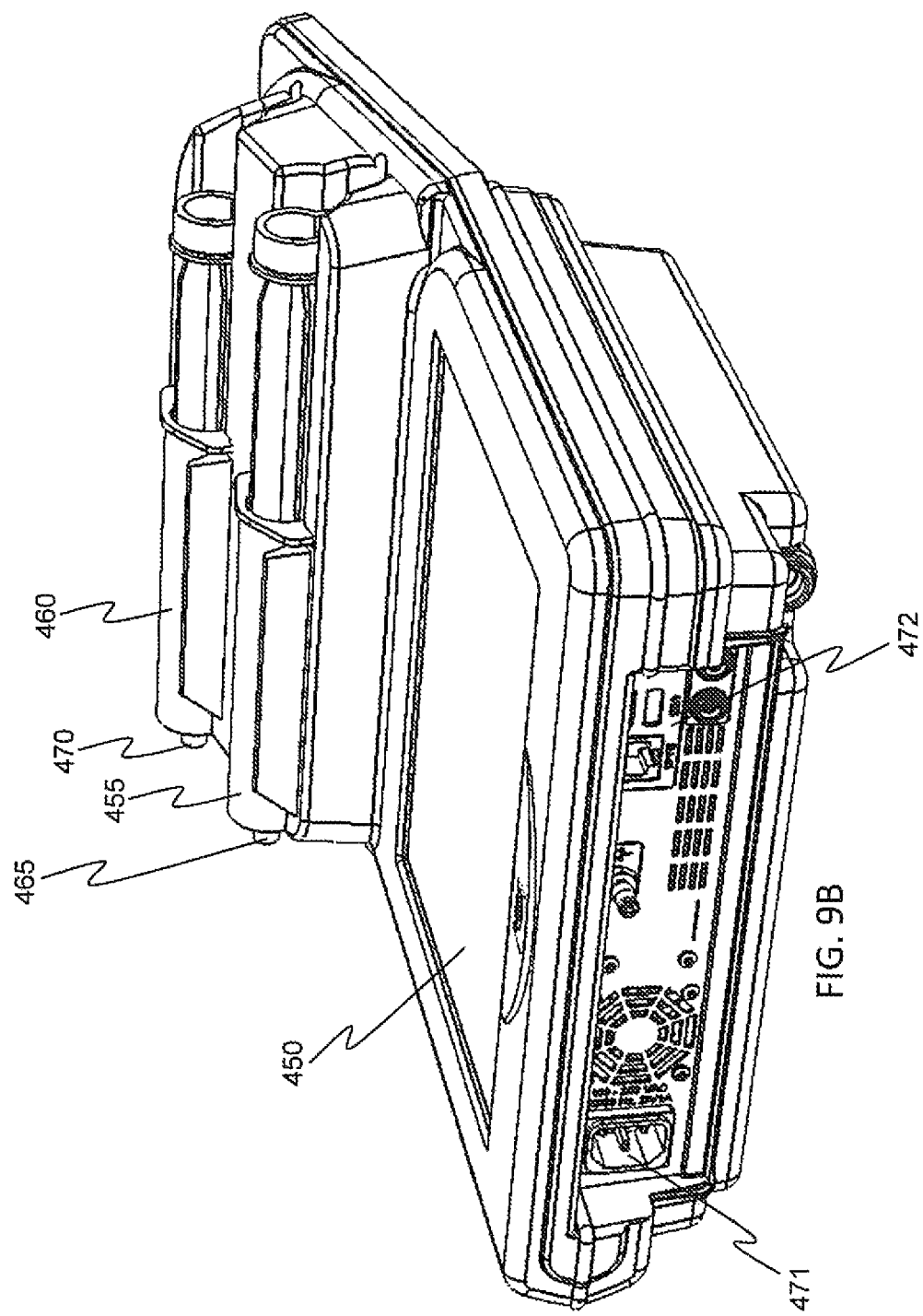

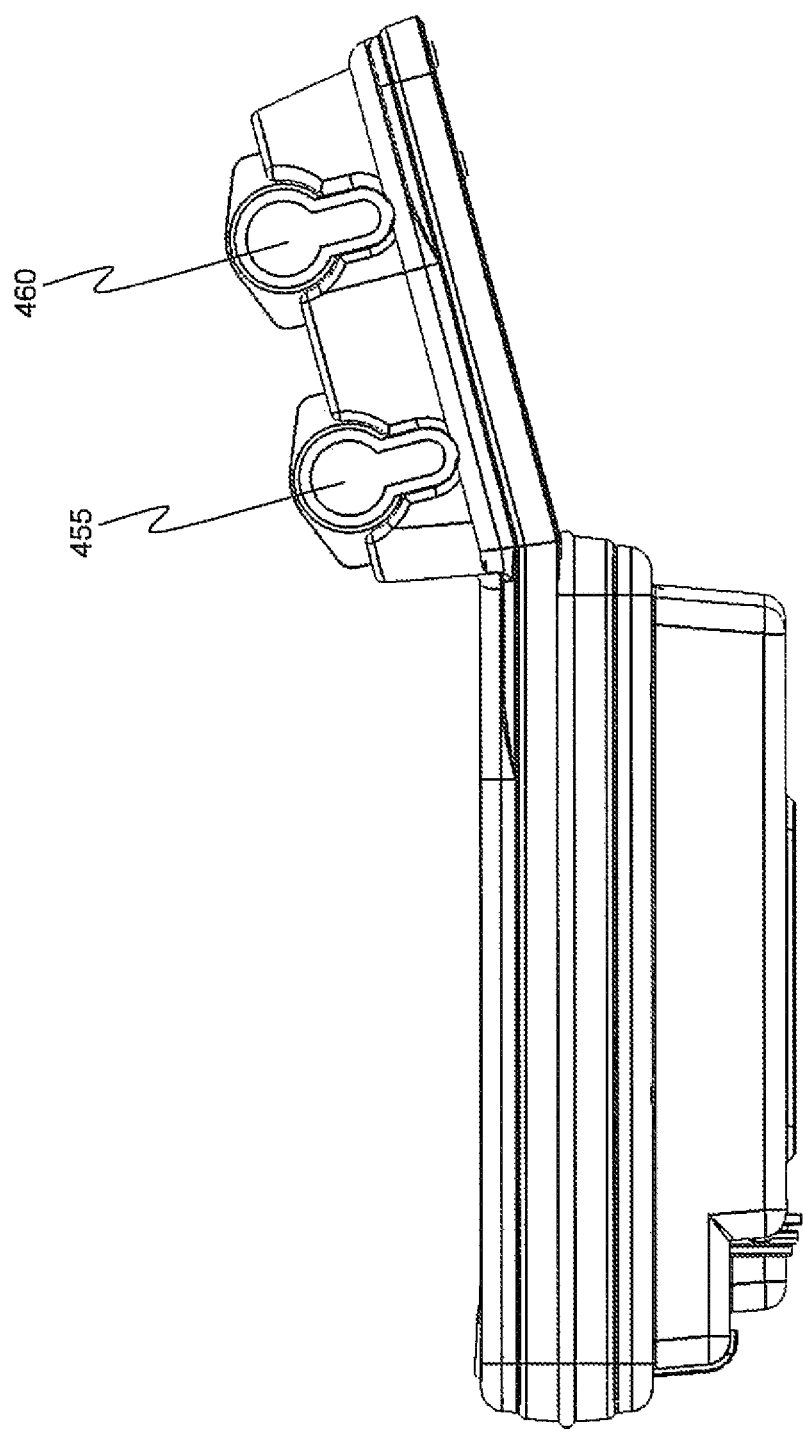

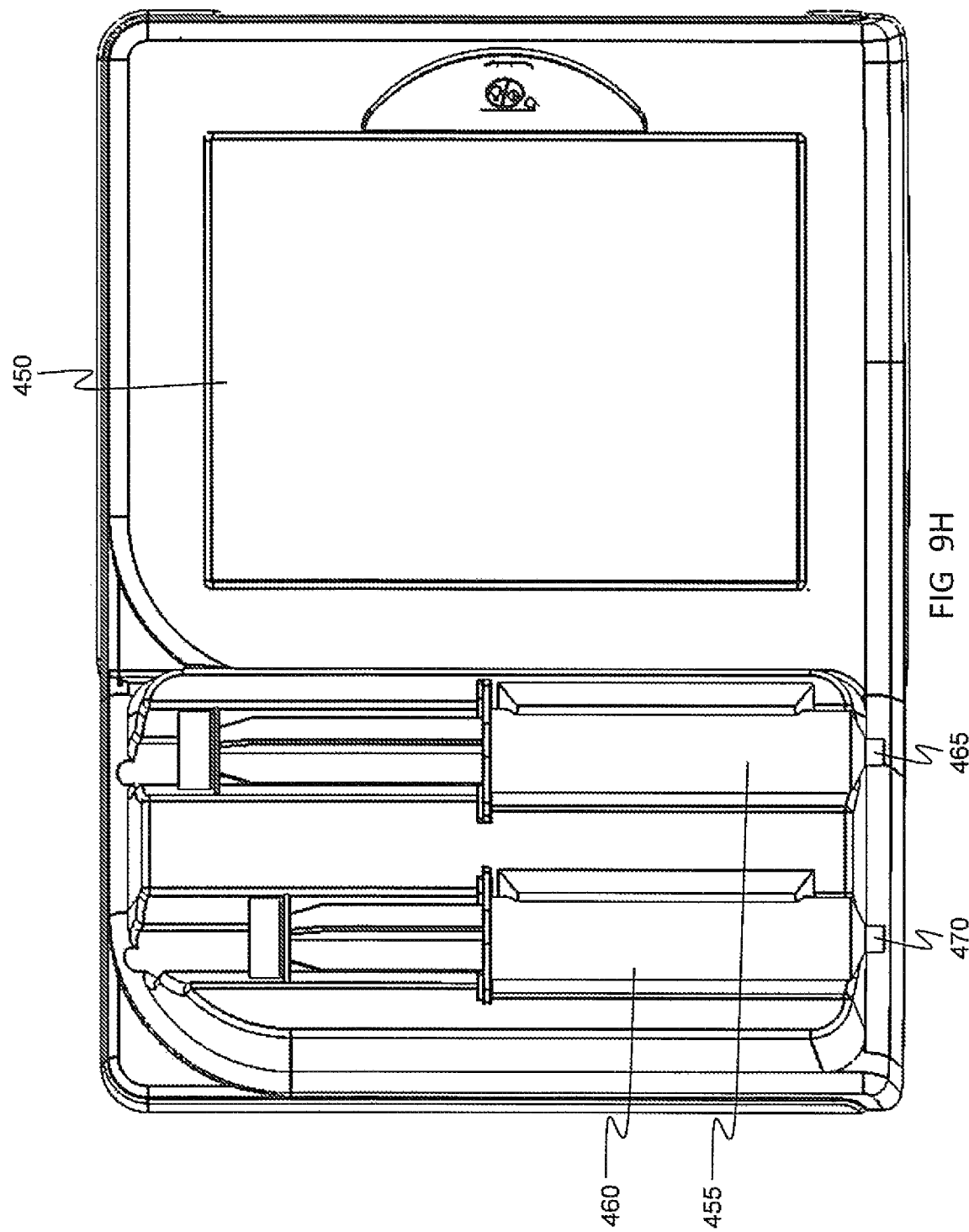

FIG. 10H

FIELD DEPLOYABLE BRAIN MONITOR AND METHOD

CROSS-REFERENCE TO RELATED APPLICATION

This application claims priority to U.S. provisional patent application No. 61/680,888, filed Aug. 8, 2012.

LICENSE RIGHTS-FEDERAL SPONSORED RESEARCH

The U.S. Government has a paid-up license in this invention and the right in limited circumstances to require the patent owner to license others on reasonable terms provided for by the terms of contract number W81XWH-12-C-0162 awarded by United States Army Medical Research Acquisition Activity (USAMRAA).

BACKGROUND OF THE INVENTION

1. Field of the Invention

The present invention relates to the monitoring and processing of signals, and particularly to the monitoring and processing of electrophysiological signals. More particularly, the present invention relates to processing electroencephalographic (EEG) signals to monitor brain function, detect the occurrence of traumatic brain injury (TBI). Even more particularly, the present invention relates to a system and method for screening, assessing, and providing mitigating treatment to improve the short- and long-term adverse outcomes of mild TBI (mTBI) and TBI. Further, the present invention relates to a system and method for providing a readily available tool to assist in the accurate and objective assessment of subjects with TBI, immediately at the point of injury (POI), during transportation, or upon arrival at a care facility, that is applicable without advanced training or expertise. Further still, the present invention relates to a system for providing closed-loop sedation for transportation or evacuation of the injured as well as closed-loop sedation or anesthesia at all echelons of care, including civilian care facilities.

2. Technical Background

Traumatic brain injury (TBI) is the leading cause of death for military personnel and civilians under the age of 45 in the United States. It has been called the "signature wound" of the war in Iraq. More than 11,800 troops have been seriously injured in an improvised explosive device (IED) attack, and many thousands more have been near enough to the explosion to cause a concussion. Based on currently existing data, veterans' advocates believe that between 150,000 and 300,000 veterans suffer from some level of TBI. The rate of TBI rises to 33 percent among wounded troops.

TBI is also a preeminent concern in the civilian population. According to the National Center for Injury Prevention and Control, over 1.4 million Americans sustain a TBI each year. Out of those 1.4 million, approximately 50,000 die, 235,000 are hospitalized, and almost 1.1 million are treated and released from an emergency department. The total direct and indirect cost of TBI among the civilian population was estimated to be about $60 billion in the United States in 2000. The major causes of such injuries among civilians include falls, motor vehicle accidents, struck by/against events, assaults, and blasts. Also, an estimated 1.6 million to 3.8 million sports-related TBIs occur each year.

If left untreated, TBI can result in permanent brain damage, which in turn can lead to a variety of disabilities such as hemiplegia, amnesia, epilepsy, loss of speech, loss of hearing, loss of vision, increased risk of Alzheimer's and Parkinson's disease, sleep disorders/insomnia, etc. TBI can also result in long-term psychological problems such as Post Traumatic Stress Disorder (PTSD), attention deficit disorder (ADD), anxiety, and depression. Over 5 million Americans suffer from some sort of TBI-related disability and have a long-term need for help to perform normal day-to-day activities.

Rapid recognition and diagnosis of the injury are paramount for the proper intervention and successful treatment of TBI. Unfortunately, TBI, and in particular mild TBI (mTBI), is difficult to detect and is considered to be vastly underdiagnosed. In addition, initial delays in diagnosis or misdiagnosis are exacerbated by environmental factors surrounding the injury, particularly in wartime and battle situations. Over 90 percent of combat-related TBIs are closed brain injuries. Soldiers who have unknowingly suffered a TBI may still appear to be in peak physical shape, yet they could potentially begin to encounter a host of psychological and cognitive problems. Failure to diagnose TBI threatens warfighters' health on many fronts. First, undiagnosed warfighters may not receive follow-up observation to look for signs of deterioration in psychological and physical condition. Second, affected individuals may be returned to duty while still being vulnerable to a second injury, with repeated injury leading to much more severe forms of TBI. Finally, in the absence of a correct diagnosis, persistent or delayed symptoms may not be correctly attributed to TBI.

Currently, there is no single diagnostic modality or device that is effective and readily available for the early detection of TBI/mTBI at the point of injury (POI)/point of departure (POD) or at higher echelons of care. It has been noted that diagnostic standards for mTBI are complex and must be considered in the larger context of neuro-psychiatric diagnosis. The classical syndrome conceptualization must be discarded and more sophisticated techniques for a multimodality approach must be developed for the battlefield and for higher echelon treatment.

In light of these needs, it is therefore an object of the present invention to provide a system and method for using electroencephalogram (EEG) recordings to non-invasively detect and diagnose TBI and mTBI. It is a further object of the present invention to provide such a system and method that is small and lightweight, capable of being carried easily, easily deployable, and preferably disposable. It is still a further object of the present invention to provide such a system and method for application and at the point of injury (POI) or upon return to the point of departure (POD) or a command outpost—in other words, to provide a system for in-the-field automated screening and assessment of TBI, to enable accurate diagnosis in conjunction with other diagnostic modalities in order to further facilitate early treatment and to prevent adverse outcomes.

In addition to TBI screening and diagnosis, there is another established and unmet need for providing enhanced capabilities in forward surgical, combat casualty care, and en-route care. Over the past 70 years, there have been attempts to use the electrical brain activity as a monitor of anesthetic depth. With increasing depth of sedation, the EEG shows a common progression from low-amplitude/high-frequency signal to high-amplitude/low-frequency signal, and finally to isoelectricity (i.e., flat signal characteristic of pharmacological coma). Changes in EEG signals following the administration of drugs, ischemic episodes, changes in perfusion, etc., tend to occur rapidly. In order to detect them in a timely manner, trained EEG technologists must interpret the EEG signals in real-time and make rapid decisions based on their expertise. This is a particularly time consuming task, reserved only for a few specific clinical applications, such as the detection of ischemia during carotid endarterectomy, or the detection of ictal activity in the long-term EEG monitoring units in epileptic patients. Raw EEG signals are typically of little value to anesthesiologists and critical care physicians, as they lack the expertise and time required for their interpretation.

Since the late 1990s, a number of processed EEG monitors have been developed to simplify the interpretation of complex EEG signals, hence providing anesthesiologists with an additional, more direct means for drug effect assessment. The use of such monitors for drug titration to achieve optimal depth of anesthesia has been shown to improve the quality of anesthetic regimen, leading to a number of advantages directly related to patient outcome, e.g., (a) avoidance of excessive depth of anesthesia, (b) avoidance of intra-operative awareness, (c) reduction in post-operative recovery times, less post-operative and ICU delirium and less time spent on a ventilator in the ICU with lesser incidence of related pulmonary infections, (d) reduction in post-operative nausea and vomiting, and (e) reduction in duration of post-operative care units stay. Additionally, using such monitors, clinicians are able to manually adjust the amount of drugs administered in order to reduce the incidence of under- and over-dosing. In fact, the use of brain function monitors has been shown to help clinicians decrease the overall amount of drug administered to their patients, which in turn leads to faster wake up and discharge time, in addition to the other benefits for patient outcome listed above. Recent research has also shown that maintaining patients at too deep anesthetic levels is associated with an increased cognitive decline and post-operative mortality rate, which can be ameliorated with brain function monitoring.

At least one recent study has shown that a brain-monitored group showed a 78 percent reduction in patient recall of unpleasant experiences as compared to the standard practice group, along with an 18 percent decrease in cost of sedative drugs. In addition, the use of brain function monitors in chemically sedated patients has been found to facilitate the conflicting goals of maintaining sedation and safely interrupting sedation to perform a neurological examination. Today, there is a high incidence of oversedation in ICUs (40 percent to 60 percent of patients). Oversedation in the ICU is a serious problem, resulting in delayed weaning from mechanical ventilation, which lengthens ICU stay and significantly increases patient risks and healthcare costs. In 2003, prolonged mechanical ventilation (>96 hours) occurred in about 300,000 cases, and accounted for nearly 7 million additional hospital days and $16 billion in hospital costs annually, projected to more than double by 2020.

Further, in spite of the advancements that have been made in anesthesia and sedation with the inclusion of brain monitoring, these systems are still relegated to mainly to surgical suites and the like. There is currently no sedation or anesthesia system utilizing brain monitoring which can be used in a setting other than a stationary one such as hospital operating room or similar facility.

In light of the above, it is therefore an object of the present invention to provide a system using brain function monitoring to enable safe anesthesia or sedation delivery in forward surgical, combat casualty care or en-route care. It is further an object of the present invention to provide a closed-loop anesthesia or sedation system capable of being applied even by a person with minimal training, and requiring no continuous human interaction or continuous human presence at the bedside. It is still further an object of the present invention to provide a system for closed-loop anesthesia or sedation which is portable, lightweight, or disposable. It is yet another object of the present invention to provide a system and method for providing closed-loop anesthesia or sedation in the field, at the point of injury (POI), or during transport between the POI and upper echelons of care (e.g., hospital, surgical suite, etc.), in addition to all echelons of care, including civilian care facilities including but not limited to operating rooms, emergency rooms and intensive care units.

SUMMARY OF THE INVENTION

The present invention relates to the acquisition, monitoring and processing of signals, and particularly to the acquisition, monitoring and processing of electrophysiological signals. More particularly, the present invention relates to processing electroencephalographic (EEG) signals to monitor brain function, detect the occurrence of specific signal patterns indicative of traumatic brain injury (TBI). Even more particularly, the present invention relates to a system and method for screening, assessing, quantifying and providing mitigating treatment to improve the short and long term adverse outcomes of mild TBI (mTBI) and TBI. Further, the present invention relates to a system and method for providing a readily available tool to assist in the accurate and objective assessment of subjects with TBI, immediately at the point of injury (POI), during transportation, or upon arrival at a care facility, that is applicable even without advanced training or expertise. Further still, the present invention relates to a system for providing closed-loop sedation for transportation or evacuation of the injured, or closed-loop anesthesia for forward surgical care, in addition to all echelons of care, including civilian care facilities.

The system collects electroencephalographic (EEG) signals from a subject and utilizes various novel algorithms to analyze and quantify those EEG signals, or at least portions thereof, to monitor the subject. It should be noted that the EEG signals acquired by the system also contain electromyographic and electro-oculographic information. Many aspects of the subject's brain function can be monitored, including, but not limited to, monitoring the occurrence of seizures, occurrence of brain hypoperfusion or ischemia, alertness, sleep architecture and quality, cognition, memory, brain functional (or neuronal) connectivity, state of consciousness, EEG slowing, loss of EEG amplitude, cortical suppression, and the like. The system can also monitor the EEG for the presence of artifacts, like environmental extraneous noise, or physiological noise (e.g., muscle activity, movements, ocular activity, etc.).

Many embodiments of the system include a small, portable, and preferably disposable brain function monitor. The brain function monitor is preferably a small or miniaturized device which is capable of being easily carried or transported for rapid deployment in the field. The monitor preferably is capable of fitting into a pack, or even a pocket, or even as a part of the electrode array or sensing system applied to a subject's head or forehead, and is thus capable of being carried without providing burdensome weight, bulk, or awkwardness to the individual carrying the system. The monitor is further preferably substantially autonomous in that it should require little or no training for the individual to apply it to an injured person, and for brain function monitoring to occur. The monitor is preferably designed such that once it is applied to the injured subject, and secured to his or her person, clothing, gear, part of his or her body part such as the head or the forehead or the like, it provides continuous or automated brain function monitoring with little or no need for human interaction, monitoring, or assessment during both subject's transportation to a location of higher echelon care (e.g., ambulance, medical evacuation transport, hospital, etc.) and at the higher echelons of care, including civilian care facilities.

Preferably, the system or monitor is constructed to be rugged. By rugged it is meant that the system, including portable enclosures and electronic components, is constructed to withstand transport even in rough terrain or air vehicles (including unmanned ones), to further withstand handling and use in all applications including in emergency scenarios (e.g., on the battlefield or in mass casualty situations), to yet further allow reliable daily use by medical personnel including emergency medical personnel or other first responders, by incorporating design features for robust and safe performance in the presence of excessive vibrations, mechanical shocks, dust or liquid ingress, EMI and electrostatic fields and discharges. The system or monitor should preferably be splash-proof (or water tight), air-tight, dust-tight, scratch-resistant, and resistant to mechanical shock and vibration. The system or monitor should preferably be portable and field-deployable in particular embodiments to a military theater of operation or transport, the scene of an accident, the home of a patient, other harsh environments, or to any clinical setting.

The system or monitor should preferably be capable of use by even non-experts. By this, it is meant that a person should not be required to possess extraordinary or specialized medical training in order to be easily taught to use the system effectively and reliably. The system should therefore preferably be automatic in operation in a number of respects. First, the system should be capable of automatic calibration of its electronic circuits, their gains, filters and the like components and features in order to maintain the accurate signal acquisition and analysis without the need for human supervision of the instrumentation during the entire course of employment. Second, the system should preferably have automatic detection of poor electrode impedance, disconnected leads, and input signal quality; for example, the system should also be capable of detecting an imbalance in electrode impedances, physiological and environmental artifacts, and electrical and magnetic interferences and noise, including those due to electrostatic fields and discharges. Third, the system should preferably be capable of artifact detection and removal on one or more levels, so as to isolate, identify or recover for analysis that part of the signal which conveys meaningful information related to a subject's brain or cortical activity pertaining to: level of consciousness; occurrence of a seizure; level of sedation or depth-of-anesthesia; brain functional (or neuronal) connectivity that, for example, can be affected by diseases such as Parkinson's and Alzheimer's; occurrence of brain hypoperfusion; brain ischemia or impaired cerebral blood flow; brain death or dysfunction or impairment; brain metabolic demand; sleep disorders; sleep architecture and quality; alertness and cognition, memory; hypo- and hyperglycemia; psychiatric disorders such as depression, ADHD, autism, OCD, etc.; person's intentions, truthfulness or substance abuse; use in brain-computer interfaces such as for control of artificial prosthetics or dysfunctional body parts or objects or devices such as robots, game consoles, vehicles and the like; and use for detection or control of another person's or one's own thought or physiologic processes. Fourth, the system should preferably include outputs which result in visual and/or audible feedback capable of informing the user of the state of the patient related to quantification of brain or cortical activity, level of consciousness, occurrence of a seizure, level of sedation and the like as previously mentioned, at any time during the period of time that the system was monitoring the patient.

Preferably, the system should operate in real time. One example of real-time operation is the ability of the system to detect a seizure or brain dysfunction event, or other pathologic or nonpathologic brain event essentially as it is happening, rather than being limited to analysis that takes place several seconds, minutes or hours afterward. Preferably, by real-time detection, it is meant that the system operates to detect brain dysfunction or injury within 3 minutes of application of the system and/or occurrence of the dysfunction or injury. More preferably, the system operates to detect brain dysfunction or injury within 1 minute of application of the system and/or occurrence of the dysfunction or injury. Still more preferably, the system operates to detect brain dysfunction or injury within 30 seconds of application of the system and/or occurrence of the dysfunction or injury. Yet more preferably, the system operates to detect brain dysfunction or injury within 15 seconds of application of the system and/or occurrence of the dysfunction or injury. Even more preferably, the system operates to detect brain dysfunction or injury within 10 seconds of application of the system and/or occurrence of the dysfunction or injury. Still yet more preferably, the system operates to detect brain dysfunction or injury within 5 seconds of application of the system and/or occurrence of the dysfunction or injury. Still even more preferably, the system operates to detect brain dysfunction or injury within 1 second of application of the system and/or occurrence of the dysfunction or injury. Most preferably, the system operates to detect brain dysfunction or injury substantially instantaneously upon application of the system and/or occurrence of the dysfunction or injury. The system further operates in real-time with respect to monitoring of the subject's physiological signals such that there is substantially no lag or delay between the body's production of the signal, and the system's monitoring of the signal. The system described in this invention also preferably incorporates a number of unique features that improve safety, performance, durability, and reliability. The system should be cardiac defibrillator proof or other electric shock proof, meaning that its electrical components are capable of withstanding the surge of electrical current associated with the application of a cardiac defibrillator or other electric shock to a patient being monitored by the system, and that the system remains operable after sustaining such a surge. The system should have shielded leads so as to reduce as much as possible the effects of external electromagnetic interference on the collection of biopotentials or physiological signals from the patient being monitored by the system. The system should be auto-calibrating, more preferably capable of compensating for the potential differences in the gains of the different acquisition channels or in the impedances of the input electrodes.

Many embodiments of the brain function monitor include a sensing system comprising an electrode array or separate, individual electrodes, and in some embodiments a brain function monitor embedded within such an array. Preferably, at least two electrodes are utilized, comprising a monitoring electrode and a ground electrode. Alternatively, at least four electrodes may be utilized. In the four electrode array, preferably two electrodes are for monitoring EEG signals in the fronto-temporal region, one reference electrode is for providing a common reference signal, and one electrode is for grounding. Other electrode arrangements including larger number of electrodes, configurations, and placements are also contemplated for use with the system. Such electrode montages may or may not include a subset of 10-20 electrode placement system, or may go beyond it in both electrode locations and their number.

The electrodes used, when either separate electrodes or when part of an array, may be any of those commonly known in the art of EEG monitoring. The electrodes preferably do not require the application of conductive paste or gel. Therefore, the electrode lead or array preferably has any necessary conductive fluids pre-applied, or, more preferably, is a dry physiological electrode requiring no conductive fluid at all. Alternatively or in addition, the electrode is a wet-dry hybrid electrode as disclosed in U.S. patent application Ser. No. 13/110,505 (which application is entirely incorporated by reference) and the like. The electrode lead or array may be affixed to or embedded into a flexible, wearable substrate or apparatus, which can be applied directly to the injured subject's head or other body part, preferably the forehead. Preferably, the substrate is designed to be flexible, easy to don and doff, and disposable yet still resilient and capable of withstanding forces common in emergency settings such as excessive vibration, movement, electric noise, EMI, electric and mechanical shock, an the like, in addition to such forces present to a lesser degree in non-emergency settings. The apparatus may be secured about the subject's head or other body part by means commonly known to those in the art, including, but not limited to, a cap or other garment or garment attachment completely encompassing the subject's head, a strap that is secured by compression or elastic means, or may utilize common fastening methods such as hook-and-loop, belt-type, snap connectors, or the like. Additionally, or in conjunction with one of the above means, an adhesive layer may be used in conjunction with a wearable apparatus to further ensure a stable, secure placement of the electrodes. In a preferred embodiment, the flexible substrate is a small patch-type or adhesive bandage (BAND-AID-type) garment comprising an adhesive layer which, when applied to the injured subject's forehead, is capable of maintaining a secure placement with minimal shifting, drift, or other movement of the apparatus, for the entire length of time necessary for monitoring. The adhesive layer is also preferably capable of providing a secure, stable attachment to the subject in the presence of dirt, sweat, and other detritus which may be covering the subject's skin during application, without the need for washing, cleaning or otherwise preparing the area of application. Preferably, in the preferred embodiments where the electrode array is integrated in the flexible substrate, the patch is small and easily applied, and integrates the acquisition electronics in the form of a few integrated circuits (ICs) or chipsets whose role is to amplify, filter, digitize, analyze, process, store or transmit, optionally wirelessly, the EEG and QEEG analog or converted digital signals. Preferably, the integrated electronics are small and inexpensive, such that the array is cost effective, such that it can be fully disposed of after use, minimizing the need for maintenance and re-shelving, or refurbishing. Preferably, the flexible substrate also embeds a connector, which allows it to be connected to a monitoring device comprising a display device. Such monitoring/display device can provide the necessary power to the flexible substrate electronics, and can perform all other necessary processing and displaying of the results.

In many embodiments, the monitoring/display device is small, rugged, and easily transportable. Also preferably, both the device and the display device may be constructed to be inexpensive and disposable. In many embodiments, the display comprises internal memory for recording the monitored EEG signals and the various processed signals and calculated values, indices, and the like for later analysis by a trained clinician. Also, in many embodiments, the display comprises an internal power source, such as a battery, that powers the device during monitoring and is sufficient to provide power at least until the injured subject can be transported to an upper echelon care location, at which point the device could be removed, data could be uploaded, and the monitor and display could be discarded. The display is preferably capable of depicting a variety of outputs from the brain function monitor, including, but not limited to, EEG signal waveforms, processed EEG signal waveforms, indices calculated by the system to indicate various aspects of the subject's brain function (e.g., suppression, seizure occurrence, state of consciousness, sedation or anesthesia level, subject's pain or analgesia level, occurrence of TBI, sleep architecture and quality, alertness, cognition, brain functional connectivity, brain hypoperfusion, ischemia or metabolic demand, memory, brain death or impaired function, hypo- or hyperglycemia and the like).

In other embodiments, the display device can be a portable medical-grade computer system, providing a graphical user interface to view in real-time the acquired EEG signals, and review all processed quantitative EEG parameters.

Also, in some embodiments of the present invention, the display device or the device itself can communicate, optionally wirelessly, with other medical equipment, such as life signs monitors and drug delivery systems, or transmit the information to internet or upload it to a cloud, preferably in real time, for remote review, analysis or storage and the like. In some embodiments, the display device or the device itself can directly control one, two or more infusion pumps to deliver intravenous drugs to the patient. In one embodiment, a single infusion pump may be used to automatically adjust the infusion rate of a drug to provide and maintain a stable and suitable concentration of said drug in the injured subject's blood plasma. In many embodiments, the drug provided is a sedative or anesthetic drug, which is infused to maintain the subject at a stable sedation or anesthesia level with minimal or no human supervision. In many embodiments, alternatively, or in conjunction with the sedation or anesthetic drug, at least one (additional) infusion pump may be provided for infusion of analgesic medication to provide a stable and suitable level of pain relief or analgesia to the injured subject. In yet other embodiments, a third pump may be used to provide muscle relaxation medication. In other embodiments, additional pumps may be used to provide various therapeutic substances such as fluids, insulin, heart rate and blood pressure regulating medications, anti-anxiety drugs, various antagonists and the like. In all embodiments, the patient's reaction to these drugs and substances is monitored via the brain monitoring system, which includes the electrode array, the device and the display device described above, which further could be integrated in a single system, potentially implantable. Such a system can enable the use of Total Intravenous Anesthesia (TIVA); or the use of other patient management therapies (e.g. fluid management, intravenous sedation, diabetes management, epilepsy management, pain management, etc.); or the delivery of other therapeutics such as electric shocks and signals (e.g., ECT, DBS), mechanical shocks and signals, chemical substances and signals, light signals, sound signals; or the use of brain-computer interface; in situations where it was not safe or possible to use such technique before.

In yet other embodiments, the display device or the device itself can directly integrate an infusion mechanism to deliver 1, 2 or more intravenous drugs. Such system, referred in the following as the Integrated Monitoring and Infusion System (IMIS), is preferably designed and constructed to be small, lightweight, and easily portable without providing cumbersome bulk or awkwardness to the person carrying it. The IMIS is also preferably constructed to be rugged and able to withstand forces and shocks attendant to the circumstances in which it is deployed (such as but not limited to battlefield, transport, etc.). In many embodiments, the IMIS comprises at least one syringe infusion pump for automatically adjusting infusion rates of a drug to be administered to the injured subject attached to, embedded in, or otherwise integrated with a portable enclosure or modular system or case. The infusion pump preferably is used to provide and maintain a stable and suitable concentration of at least one drug or substance to the injured subject. In many embodiments, the drug provided is preferably a sedative or anesthetic drug, which the IMIS infuses and monitors to maintain the subject at a stable sedation level with minimal or no human supervision. In many embodiments, alternatively, or in conjunction with the sedation or anesthesia drug, at least one additional infusion pump may be provided for infusion of analgesic medication to provide a stable and suitable level of pain relief or analgesia to the injured subject. In many embodiments, the IMIS is used for sedation and/or pain management purposes to stabilize the patient for en-route care provided while waiting and/or during transport from the point of injury to a location of higher echelon care as well as at all echelons of care including civilian care facilities.

In many embodiments, the IMIS embeds a control algorithm which utilizes input from the brain function monitor, and optionally from a user, to calculate preferred infusion rates of the sedation or anesthetic and/or analgesic drugs. For example, in many embodiments to control algorithm calculates preferred infusion rates based at least in part on a calculated index (e.g., $WAV_{CNS}$) in combination with user inputted data specific to the subject (e.g., weight, height, age, sec, etc.). Preferably, the algorithm performs these calculations substantially in real-time to provide the necessary modifications to the drug infusion rates immediately. In some embodiments the IMIS embeds a control algorithm which utilizes input from the brain function monitor to calculate preferred infusion rates of other therapeutic drugs and substances for patient management (e.g., fluids, insulin, heart rate and blood pressure regulating medications, anti-anxiety drugs, various antagonists and the like), or to control the delivery of other patient management and therapy solutions that were previously mentioned and that not necessarily utilize only infusion but by other avenues including but not limited to gaseous administration and absorption, and utilizing other therapeutic signals and methods (electrical, mechanical, etc.).

The IMIS device may be operated manually or in a closed-loop manner. In one preferred embodiment, the IMIS and the associated electrode array are used in the field, on injured subjects, to deliver and maintain a proper level of sedation and analgesia, or other therapeutic substances and methods, while waiting for medical evacuation. In other embodiments, the IMIS can be used in medical evacuation vehicles, for en-route care, to control the level of stress and pain of the patient, or to provide other substances and therapies (e.g., management of fluids, insulin, heart rate and blood pressure regulating medications, anti-anxiety drugs, various antagonists, as well as electrical, mechanical, sound, light and the like therapeutic signals) and keep him or her safe or comfortable. In yet another preferred embodiment, the IMIS is used in the emergency room or other clinical setting and the like in higher echelons of care facilities, to provide sedation or anesthesia or other therapies for patient management. In yet another preferred embodiment, the IMIS is used in the peri-operative environment to provide sedation or anesthesia or other patient management therapies to the patient. Finally, in yet other embodiments, the IMIS can be used in Intensive Care Units (ICUs), to provide sedation or other patient management therapies to the patient and help through his or her recovery process.

The brain function monitor, IMIS, the combination thereof, and the methods for using these systems are preferably designed to be applicable for in-the-field uses. In-the-field is meant to be any application, setting, location or circumstance where the subject is injured and does not have immediate, ready access to sophisticated, formal medical care settings. By way of example, and not meant to limit the applications of the present invention, the device and methods described herein can be used in battlefield, professional/recreational/amateur sports, or other entertainment (such as concert) venues, or may be utilized by first responders, medical transport and/or evacuation, security, police, or the like in emergency or other injury situations. In other words, the present invention's device(s) and methods are contemplated to be used for many injuries even those with a sudden onset, in order to provide monitoring, assessment, diagnosis, anesthesia, sedation, and/or pain management until the injured subject can be transported to an end care location of upper echelon medical care with equipment that would supplant this portable, disposable device and the methods for its use. Yet, it should be noted that the device discussed in the present invention can also be designed and used in all clinical environments and echelons of care.

One embodiment of the present invention includes a method of detecting traumatic brain injury comprising steps of applying a wearable apparatus to a subject's forehead, the wearable apparatus comprising an electrode array affixed to, embedded in, or integrated into the wearable apparatus; a microprocessor, the microprocessor comprising an algorithm for real-time detection of abnormal EEG pattern signals, a display comprising an internal power source and internal memory, the display weighing less than 5 ounces, acquiring, with the electrode array, an EEG signal from the subject; and determining with the algorithm whether traumatic brain injury has occurred based at least in part on the EEG signal.

Another embodiment of the present invention includes a method of detecting traumatic brain injury comprising steps of applying a wearable apparatus to a subject's forehead, the wearable apparatus comprising at least three electrode leads affixed to, embedded in, or integrated into the wearable apparatus, at least one lead for monitoring fronto-temporal brain activity, at least one lead for monitoring parietal brain activity, and at least one lead for monitoring occipital brain activity, a microprocessor, the microprocessor comprising an algorithm for real-time detection of abnormal EEG pattern signals, a display comprising an internal power source and internal memory, the display weighing less than 5 ounces, acquiring, with the electrode leads, an EEG signal from the subject; and determining with the algorithm whether traumatic brain injury has occurred based at least in part on the EEG signal.

Yet another embodiment of the present invention includes a method of detecting traumatic brain injury comprising steps of applying a wearable apparatus to a subject's forehead, the wearable apparatus comprising an electrode array affixed to, embedded in, or integrated into the wearable apparatus, an amplifier, an analog-to-digital converter, a digital-signal-processor comprising an algorithm for real-time detection of abnormal EEG signal patterns, and a display comprising an internal power source and internal memory, the display weighing less than 5 ounces, acquiring, with the electrode array, an EEG signal from the subject, amplifying the obtained EEG signal, converting the amplified EEG signal from analog to digital, and determining with the algorithm whether traumatic brain injury has occurred based at least in part on the amplified digital EEG signal.

Still another embodiment is a method of detecting traumatic brain injury comprising steps of applying a wearable apparatus to a subject's forehead, the wearable apparatus comprising an electrode array affixed to, embedded in, or integrated into the wearable apparatus, a microprocessor, the microprocessor comprising an algorithm for real-time detection of abnormal EEG pattern signals, a display comprising an internal power source and internal memory, the display weighing less than 5 ounces, acquiring, with the electrode lead, an EEG signal from the subject; determining with the algorithm whether traumatic brain injury has occurred based at least in part on the EEG signal, saving the acquired EEG signal and algorithm determination to the internal memory, and providing the display to a trained clinician to access the saved EEG signal and algorithm determination for further assessment of the subject.

Still another embodiment of the present invention includes a portable brain monitoring system comprising a disposable sensing system comprising an electrode array comprising at least two electroencephalogram (EEG) electrodes, the at least two electrodes each having a signal, and at least one electronic component attached to or integrated within the electrode array comprising an input channel for receiving the signals from the at least two electrodes, at least one filter for removing noise or artifacts from the signals, and an output channel for transmitting a filtered signal, and a monitoring system for receiving the transmitted filtered signal, the monitoring system comprising a display, wherein the disposable sensing system is disposed of after one use with a subject.

Another embodiment of the present invention includes a portable brain monitoring system comprising a disposable sensing system comprising an electrode array comprising at least two electroencephalogram (EEG) electrodes, the at least two electrodes each having a signal, and at least one electronic component attached to or integrated within the electrode array comprising an input channel for receiving the signals from the at least two electrodes, at least one filter for removing noise or artifacts from the signals, an analog to digital converter for converting the signals from analog to digital, and an output channel for transmitting a digital signal, and a monitoring system for receiving the transmitted filtered digital signal, the monitoring system comprising a display, wherein the disposable sensing system is disposed of after one use with a subject.

Still another embodiment of the present invention includes a portable brain monitoring system comprising a disposable sensing system comprising an electrode array comprising at least two electroencephalogram (EEG) electrodes, the at least two electrodes each having a signal, and at least one electronic component attached to or integrated within the electrode array comprising an input channel for receiving the signals from the at least two electrodes, at least one filter for removing noise or artifacts from the signals, an analog to digital converter for converting the signals from analog to digital, and a processor comprising an algorithm for quantifying at least a portion of the digital signal and an output channel for transmitting a digital signal and/or a quantified at least portion of the digital signal, a monitoring system for receiving the transmitted digital signal and/or quantified at least portion of the digital signal, the monitoring system comprising a display, wherein the disposable sensing system is disposed of after one use with a subject.

Yet another embodiment of the present invention includes a portable brain monitoring system comprising a disposable sensing system comprising an electrode array comprising at least two electroencephalogram (EEG) electrodes, the at least two electrodes each having a signal, and at least one electronic component attached to or integrated within the electrode array comprising an input channel for receiving the signals from the at least two electrodes, at least one filter for removing noise or artifacts from the signals, and an analog to digital converter for converting the signals from analog to digital, and a monitoring system comprising a display wherein the disposable sensing system is disposed of after one use with a subject, either the disposable sensing system or the monitoring system further comprises a processor comprising an algorithm for detecting traumatic brain injury (TBI) and outputting a quantified signal corresponding to a level of the injury, and the display depicts the level of injury.

Even another embodiment of the present invention includes an apparatus for automated drug delivery of anesthesia or sedation comprising at least two input channels for connecting with electroencephalogram (EEG) electrodes, having a signal, for application to a subject's head, an interface for entering the subject's weight, a processor comprising an algorithm for real-time monitoring of the subject's EEG signals, quantifying at least a portion of the EEG signal, and calculating an index based on at least the portion of the subject's quantified EEG signals, at least one infusion pump or valve for delivery of as anesthetic or sedative drug, wherein the at least one infusion pump or valve is operated automatically based at least on part on the calculated index and the subject's weight.

Still yet another embodiment of the present invention includes a portable apparatus for automated drug delivery of anesthesia or sedation comprising a portable enclosure or modular system either weighing in total less than about 75 pounds that can be hand carried by one individual when in a rugged terrain comprising at least two input channels for connecting with electroencephalogram (EEG) electrodes, having a signal, for application to a subject's head, an interface for entering the subject's weight, a processor comprising an algorithm for real-time monitoring of the subject's EEG signals, quantifying at least a portion of the EEG signal, and calculating an index based on at least the portion of the subject's quantified EEG signals, at least one infusion pump for delivery of an anesthetic or sedative drug, wherein the at least one infusion pump is operated automatically based at least on part on the calculated index and the subject's weight.

Even still another embodiment of the present invention includes n apparatus for automated drug delivery of sedation or anesthesia comprising at least two input channels for connecting with electroencephalogram (EEG) electrodes, each electrode having a signal, for application to a subject's head, an interface for entering the subject's weight, a processor comprising an algorithm for real-time monitoring of the subject's EEG signals, quantifying at least a portion of the EEG signal, and calculating an index based on at least the portion of the subject's quantified EEG signals, at least two infusions pumps for delivering at least two drugs, wherein the at least two infusion pumps are operated automatically based at least on part on the calculated index and the subject's weight.

An apparatus for automated drug delivery comprising at least one feedback signal which may not be available at all times, at least one infusion pump or valve for delivery of a drug, at least one processor comprising at least two control algorithms that calculate the input of the at least one infusion pump based on a last available said feedback signal, the first control algorithm having a first refresh rate and the second control algorithm having a second refresh rate that is slower than the first control algorithm, wherein the at least one infusion pump or valve is operated automatically based on the calculated input of said first control algorithm when the feedback signal is available, and based on the calculated input of the said second control algorithm when the at least one feedback signal is not available.

Other embodiments similar to those listed above have one or more of the following features: a display weight of less than 4 ounces; the display showing either or both of raw EEG data and processed data about patient brain state; manual enablement/disablement of automated drug administration; measurement of fronto-temporal cortical activity solely to determine whether drugs are needed; built-in infusion and monitoring control algorithms (as discussed later in this application); adaptive monitoring features that provide for use to reduce the risk of sedative overdose in patients with high blood loss; the monitoring system being disposable in its entirety; a paper battery suitable for providing adequate power for the application over adequate measurement/analysis times of at least 2, and preferably 3, and more preferably 4 hours; a display the size of a credit card; a memory to store the signal(s) for analysis later; the capability to automatically detect seizure, suppression, or unconsciousness; the display being capable of displaying indices, warnings, or other messages for the user; portable and ruggedized construction permitting use on the battlefield, at a sporting even, by emergency first responders, and at schools and workplaces; a battery integrated into display such that the display can be traded off and used for later data analysis, while permitting continued monitoring by swapping out with a new display; and an internal memory and USB interface built into the display permitting the display to be plugged into a computer for easy and fast data transfer, reprogramming, software or firmware updates, etc.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

Various embodiments of the present invention may gain the benefit of many existing systems, methods and devices, whose patent applications are hereby incorporated by reference, including: systems and methods for the detection of seizures and other ictal activity (U.S. patent application Ser. No. 12/259,852; U.S. patent application Ser. No. 13/731, 315); various varieties of electrodes and sensors (e.g., U.S. patent application Ser. No. 13/110,533 U.S. patent application Ser. No. 13/899,632); systems and methods for acquiring biosignals in the presence of high-frequency interference (U.S. patent application Ser. No. 11/827,906; U.S. patent application Ser. No. 13/335,256); and systems and methods for denoising large-amplitude artifacts in electrograms using time frequency transforms (U.S. patent application Ser. No. 10/968,348), as well as issued patents, which are also hereby incorporated by reference, including U.S. Pat. No. 7,603,168 disclosing closed loop systems and processes, U.S. Pat. No. 7,672,717 disclosing artifact detection, and U.S. Pat. No. 7,373,198 disclosing quantification indexes for cortical activity.

It is to be understood that both the foregoing general description and the following detailed description are merely exemplary of the invention, and are intended to provide an overview or framework for understanding the nature and character of the invention as it is claimed. It is understood that many other embodiments of the invention are not directly set forth in this application but are none the less understood to be incorporated by this application. The accompanying drawings are included to provide a further understanding of the invention, and are incorporated in and constitute a part of this specification. The drawings illustrate various embodiments of the invention and together with the description serve to explain the principles and operation of the many embodiments of this invention.

BRIEF DESCRIPTION OF THE DRAWINGS

FIGS. 9A-J. Various views of one embodiment of the IMIS including A) front-left perspective view; B) front-right perspective view; C) back perspective view; D) front isometric view; (E) back isometric view; F) left isometric view; G) right isometric view; H) top isometric view; I) bottom isometric view; and J) isometric view.

FIGS. 10A-H. Various screenshots of one embodiment of the present invention including: A) a screenshot of an "Effect" screen; B) a screenshot of a "Pumps" screen; C) another screenshot of a "Pumps" screen; D) a screenshot of a "PCLC" screen; E) another screenshot of a "PCLC" screen; F) another screenshot of a "Pumps" screen; G) a screenshot of a "patient information screen; and H) another screenshot of a "Patient information" screen.

DETAILED DESCRIPTION OF THE PREFERRED EMBODIMENTS

Figure 1A:
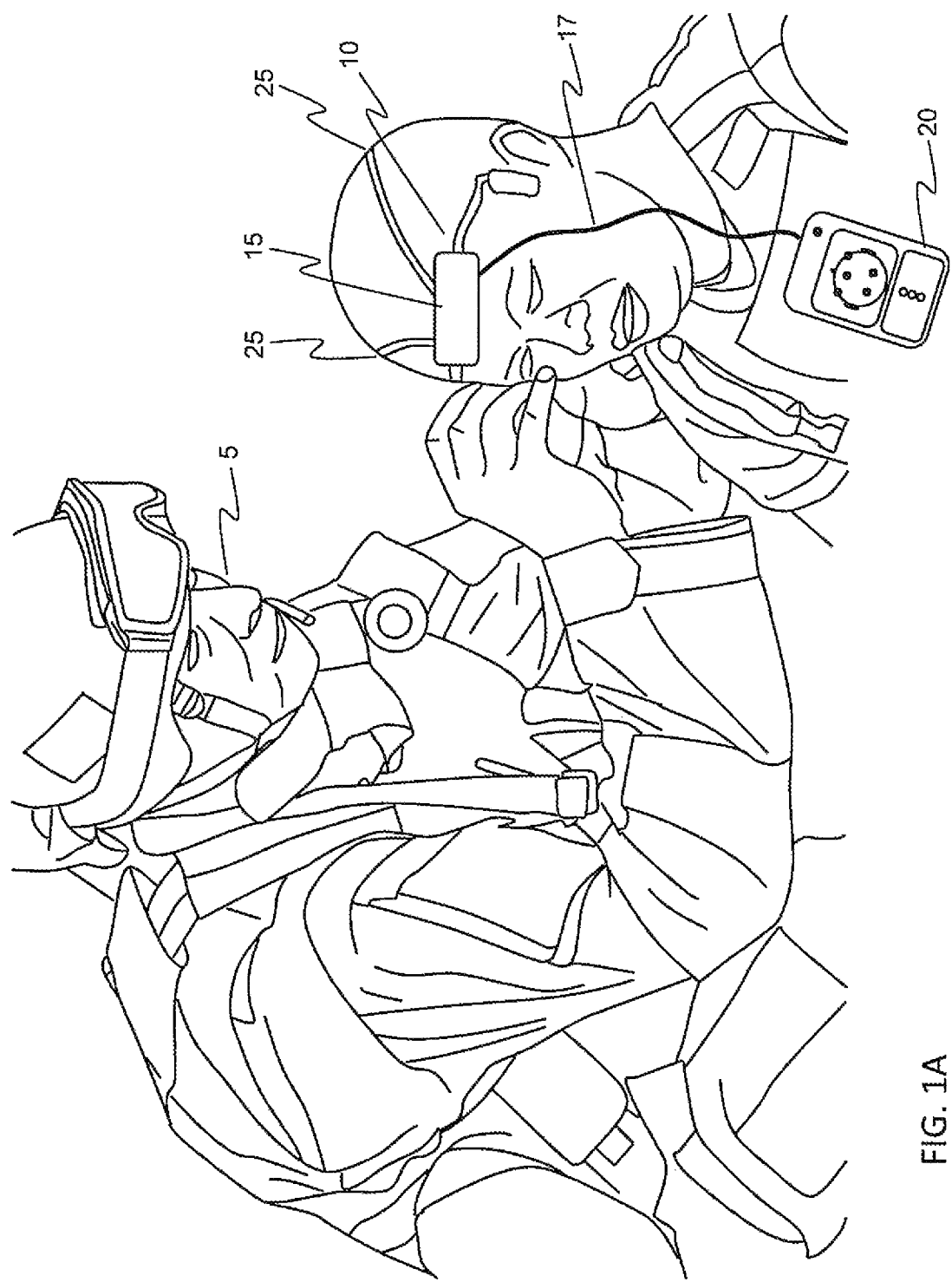
FIG. 1A. Depiction of a soldier applying the device having a separate monitor to an injured subject in the field.

The present invention relates to the acquisition, monitoring and processing of signals, and particularly to the acquisition, monitoring and processing of electrophysiological signals. More particularly, the present invention relates to the processing of electroencephalographic (EEG) signals to monitor brain function in order to detect the occurrence of traumatic brain injury (TBI). Even more particularly, the present invention relates to a system and method for screening, assessing, and providing mitigating treatment to improve the short and long term adverse outcomes of mild TBI (mTBI) and TBI. Further, the present invention relates to a system and method for providing a readily available tool to assist in the accurate and objective assessment of subjects with TBI, immediately at the point of injury (POI), during transportation, or upon arrival at a care facility, that is applicable without advanced training or expertise. Further still, the present invention relates to a system for providing closed-loop automated sedation delivery for transportation or evacuation of the injured, or closed-loop intravenous anesthesia for forward or clinical surgical care.

For the present invention, the subject whose EEG signal is being measured can be any type of animal, preferably a mammal, most preferably a human. Also, caregiver and clinician is understood to include not only those skilled in the use of EEG equipment and methodologies, such as doctors, physicians, anesthesiologists, EEG technologists, emergency response personnel, nurses, and the like. The device and methods are designed to be used and performed, respectively, largely by untrained or minimally trained personnel, until the injured subject may be transported to a clinician as described above for more acute and skilled care in proper facilities or locations.

The various embodiments of the present invention are preferably one or more of portable, ruggedized, disposable, and capable of rapid application and use. By "portable" it is meant that a single embodiment is light enough in weight and compact enough in size to be carried in a small handheld and hand-carried case that may be carried easily by a single person and applied to a subject or patient without impeding the subject's easy and safe transport. Preferably, this means that the subject is completely untethered, except, in some embodiments, to a small monitor and/or therapy device which can be attached to the subject, the subject's clothing or gear, or the subject's gurney, stretcher, or bed and easily moved along with the subject. Preferably, the entire system weighs less than 75 lbs. More preferably, the entire system weighs less than 60 lbs. Still more preferably, the entire system weighs less than 50 lbs. Yet more preferably, the entire system weighs less than 40 lbs. Even more preferably, the entire system weighs less than 25 lbs. Still more preferably, the entire system weighs less than 20 lbs. Yet more preferably, the entire system weighs less than 15 lbs. Even more preferably, the entire system weighs less than 10 lbs. By "ruggedized" it is meant that the embodiment has features that harden it to mechanical and electrical shocks and dust/fluid ingress, etc., as described elsewhere in this application which permit the embodiment to be transported and used in emergency settings. "Disposable" is defined by a number of factors as discussed elsewhere in this application. "Rapid application and use" means that the system or apparatus embodiment can be taken from a storage or transportation configuration, applied to a subject or patient, and used for measurement, monitoring, analysis and/or therapy in less than ten minutes. More preferably, application can be performed in less than one minute. More preferably, application can be performed in less than thirty seconds. Still more preferably, application can be performed in less than ten seconds. More preferably still, application can be performed in less than five seconds. Such rapid applications can be realized by providing a monitor embodiment as a simple adhesive patch that is peeled from a backing and applied to a patient or subject's forehead, whereupon the monitor embodiment automatically activates, self-calibrates, and begins measurement, monitoring, analysis, and/or therapy.

Various embodiments of the methods of the present invention include one or more of the following steps, and variations thereof. These steps include, but are not limited to, monitoring a subject with a brain having a left hemisphere and a right hemisphere, by connecting the subject to a brain function monitoring device with at least one electrode lead comprising at least one measurement electrode and at least one reference electrode, the at least one electrode lead comprising at least one EEG electrode, having a signal associated therewith, positioned on a subject's head to monitor activity of the subject's brain, the reference electrode comprising at least one EEG electrode, each electrode providing an EEG signal. Alternatively, monitoring of the subject's brain function can be performed with at least one electrode array comprising a plurality of measurement EEG electrodes and at least one reference electrode, each of the plurality of EEG measurement electrodes having a signal associated therewith.

Similarly, various embodiments of the device of the present invention include one or more of the following components, and variations thereof. These elements include, but are not limited to, an electrode array(s), a display device, an anesthetic or sedation infusion and monitoring system, a processor, which may embed signal processing algorithms, and/or a control algorithm(s) for controlling drug infusion, and drug infusion device(s).

All embodiments of the present invention involve acquiring an electroencephalographic (EEG) or functionally equivalent signals from a subject or a patient. In acquiring EEG signals, electrodes can be placed at various locations on the subject's scalp in order to acquire EEG or brain wave signals. Common locations for the electrodes include frontal (F), temporal (T), parietal (P), anterior (A), central (C) and occipital (O). If the particular embodiment utilizes an array of electrodes, the array may contain electrodes positioned at one or several of these or other locations. Preferably for the present invention, at least one electrode is placed at or near the fronto-temporal region of the subject's brain, on the subject's scalp. Additionally, preferably at least two electrodes are used, one signal electrode and one reference electrode; if further EEG or brain wave signal channels are desired, the number of electrodes required will depend on whether separate reference electrodes are used or, instead, a single reference electrode is used for multiple channels. The step of monitoring brain function includes using at least one sensor to measure a subject's brain wave signals over a period of time. The brain wave or EEG signals can be obtained by any method known in the art, or subsequently developed by those skilled in the art to detect these types of signals. Sensors include but are not limited to electrodes or magnetic sensors. Since brain wave signals are, in general, electrical currents which produce associated magnetic fields, the present invention further anticipates methods of sensing those magnetic fields to acquire brain wave signals similar to those which can be obtained through for example an electrode applied to the subject's scalp.

The electrodes may be affixed to or preferably embedded into a flexible, wearable apparatus which can be applied directly to the injured subject's head, preferably the forehead. Preferably, the wearable apparatus is designed to be flexible, easy to don and doff, and disposable yet still resilient and capable of withstanding forces common in emergency settings. As used in this application, an "emergency setting" is limited to places and events outside of hospitals, clinics, and other places where trained medical professionals are close at hand. Exemplary emergency settings include battlefields; settings of vehicle or construction accidents; sites of mass casualty, terrorist attack, or natural or industrial disaster; schools; sports fields and arenas; shopping areas, pedestrian areas, and other places generally open to the public; workplaces, homes, and residences, and the like. A staffed and equipped emergency room is not an "emergency setting." Forces common in emergency settings include those previously mentioned as well as those associated with roughly ported or dropped—accelerations and shocks uncommon in hospital and emergency room settings and which would damage or destroy equipment designed for use in a hospital. However, it is to be noted that the current invention is not limited to use in emergency settings only. The apparatus may be secured about the subject's head by means commonly known to those in the art, including, but not limited to, a cap or other garment completely encompassing the subject's head, a strap that is secured by compression or elastic means, or may utilize common fastening methods such as hook-and-loop, belt-type, snap connectors, or the like. Additionally, or in conjunction with one of the above means, an adhesive layer may be used in conjunction with a wearable apparatus to further ensure a stable, secure placement of the electrode lead or array. In a preferred embodiment, the flexible apparatus is a small patch-type garment comprising an adhesive layer which, when applied to the injured subject's forehead, is capable of maintaining a secure placement with minimal shifting, drift, or other movement of the apparatus, for the entire length of time necessary for monitoring. The adhesive layer is also preferably capable of providing a secure, stable attachment to the subject in the presence of dirt, sweat, and other detritus which may be covering the subject's skin during application, without the need for washing, cleaning or otherwise preparing the area of application. Preferably, in preferred embodiments where the electrode array or sensing system is affixed to or embedded in a patch-type garment, the patch is small and easily applied. Preferably, the surface area of the sensing system and/or patch, including electrode array(s) is less than 10 square inches. More preferably, the surface area of the sensing system and/or patch is less than 8 square inches. Even more preferably, the surface area of the sensing system and/or patch is less than 6 square inches. Still more preferably, the surface area of the sensing system and/or patch is less than 4 square inches. Yet more preferably, the surface area of the sensing system and/or patch is less than 2 square inches. Other similar methods of acquiring physiological signals may be used in the present invention which are known to those skilled in the art for acquiring signals such as electrocardiography (ECG), electrical impedance tomography (EIT), electromyography (EMG) and electro-oculography (EOG).

In order to obtain a good EEG or brain wave signal it is desirable to have low impedances for the electrodes. Typical EEG electrodes connections may have impedance in the range of from 5 to 10 kiloohms. It is, in general, desirable to reduce such impedance levels to below 2 kiloohms. Therefore a conductive paste or gel may be applied to the electrode to create a connection with impedance below 2 kiloohms. Alternatively, the subject's skin may be mechanically abraded, the electrode may be amplified using active circuitry, or a micro-penetrating dry electrode may be used. Dry physiological recording electrodes of the type described in U.S. Pat. No. 6,785,569 can be used. U.S. Pat. No. 6,785,569 is incorporated by reference. Dry electrodes provide the advantage that there is no gel to dry out, no skin to abrade or clean, and that the electrode can be applied in hairy, sweaty, and/or dirty areas such as the scalp, particularly for in-the-field applications.

It is also contemplated that the electrodes may be nothing more than electrode pads consisting of a thin conductive coating (e.g., a coating of silver or other metal) printed onto the underside of a flexible substrate. In such an embodiment, the flexible substrate preferably has flexible printed circuit board (PCB) traces embedded in it to carry signals acquired by the electrodes or electrode pads to processing electronics. Although "dry" in the sense that these simple electrodes have no electrode gel, such electrodes are to be distinguished from the dry electrodes mentioned above, and are not referred to herein as dry electrodes.

In one preferred embodiment, the electrode array is integrated in a flexible substrate that also connects to the EEG acquisition electronics, in particular a filtering, and/or amplification and digitization electronics. The amplification circuitry preferably comprises a single micro-electronic IC or chipset, e.g., an application-specific integrated circuit (ASIC), connected to at least two electrodes, and having an input channel or other component for receiving signals from the electrodes. The IC or chipset amplifies the voltage between the two electrodes. Preferably, the IC or chipset integrates filters to filter out DC bias (when required), as well as high frequency (e.g., for anti-aliasing). The filtering circuitry may also integrate a modified Sallen-Key filter to minimize the effect of high frequency interferences from electro-surgical units (ESUs) or radio frequency (RF) interference. In addition, the IC or chipset can also integrate an analog-to-digital (AD) converter (e.g., successive approximation or sigma-delta conversion) to digitize the amplified waveform. Finally, the IC or chipset may be limited to a single channel acquisition, or may be capable of multiple channel acquisition. In some embodiments each "channel" of EEG data uses its own dedicated ASIC or other suitable chip to perform the required amplification, filtering, A/D conversion, etc., to minimize noise and crosstalk. A custom ASIC suitable for use preferably has a common-mode rejection ratio (CMRR) of better than −110 dB. More preferably, it has a CMRR of better than −120 dB. Even more preferably, it has a CMRR of better than −140 dB. Further preferably, a custom ASIC suitable for use preferably has a signal-to-noise ratio (SNR) of no greater than 3 microvolts peak-to-peak. More preferably, it has an SNR of no greater than 2 microvolts peak-to-peak. Even more preferably, it has an SNR of no greater than 1 microvolt peak-to-peak. Until recently, the non-availability of a suitable commercially-available IC, and the expense of producing a suitable custom ASIC, has been a major impediment to the development of a cost-effective disposable EEG acquisition apparatus. The Texas Instruments ADS1299 is a low-noise, 8-channel, simultaneous-sampling, 24-bit, delta-sigma (Δs) analog-to-digital converter (ADC) front-end for biopotential measurements with a built-in programmable gain amplifier (PGA), internal reference, and an onboard oscillator. It has a CMRR of −110 dB and a noise floor of about 1 microvolt peak-to-peak. Such an IC as the ADS1299 may be used instead of a custom ASIC, although a custom ASIC would still bring advantages, including the potential for reduced power consumption and thus longer battery life, and thus should preferably be used if implementation of such an ASIC is economically pragmatic.

The flexible substrate may also integrate a micro-connector to allow its connection to a display device, or to the Integrated Monitoring and Infusion System (IMIS) discussed below. The flexible substrate and/or the electronic components attached to or integrated within the flexible substrate or electrode array thus also comprises an output channel or other component for transmitting the digital signal. The flexible substrate may also integrate a battery (lithium-ion, thin film battery or button cell battery) to supply power to the electronics; if no battery is so integrated, the electronics may be powered by a battery or other power source contained in or associated with the display (as discussed below), the electrodes, or other components of the device or system of the present invention. Optionally, one or more light-emitting diodes (LEDs) may be integrated to the substrate to inform the user when the system is turned on, or whether the electrodes are properly placed, or whether the signals are of good enough quality. Further optionally, the electronics may also integrate a signal processor to process the acquire EEG signals. Optionally, a memory bank may be added to store the acquired and processed variables for later use. In most embodiments, the electrode array and its flexible substrate are for single use only and should be discarded after use. If a memory bank is present, users may optionally download the stored data before discarding the substrate.

Preferably, the battery used in any disposable portion of the present invention is a so-called "primary cell," i.e., one designed to be used once and discarded, rather than a "secondary cell," i.e., a rechargeable battery. The battery used in any non-disposable portion of the present invention—e.g., the display, in embodiments that use a separate reusable display—may be a primary cell or a secondary cell, and in some embodiments is a secondary cell that can be easily recharged, for example by plugging the display or other non-disposable portion of the device into a USB port via a USB connector for recharging. Among primary cells, most batteries small and thin enough to be used on the flexible substrate contemplated above are coin-cell or button-cell types which provide only a few milliamp-hours (mAh), but such batteries generally do not hold enough energy for the present application. Any battery used for the disposable portion of the present invention should preferably be able to sustain two to three hours of EEG acquisition at minimum. Therefore, some embodiments will preferably use a paper battery, i.e., a battery which uses a paper dialectric. Such batteries provide moderate power, but are still small and flat. An ultra-thin lithium/manganese dioxide primary battery, such as the GMBPOW/CP225040 from Guangzhou Markyn Battery Co., Ltd., which has a nominal capacity of 750 mAh, is one such battery. Various printed battery and flexible battery designs known to those skilled in the art, such as mesh batteries, may also be implemented if cost-effective.

Figure 1B:
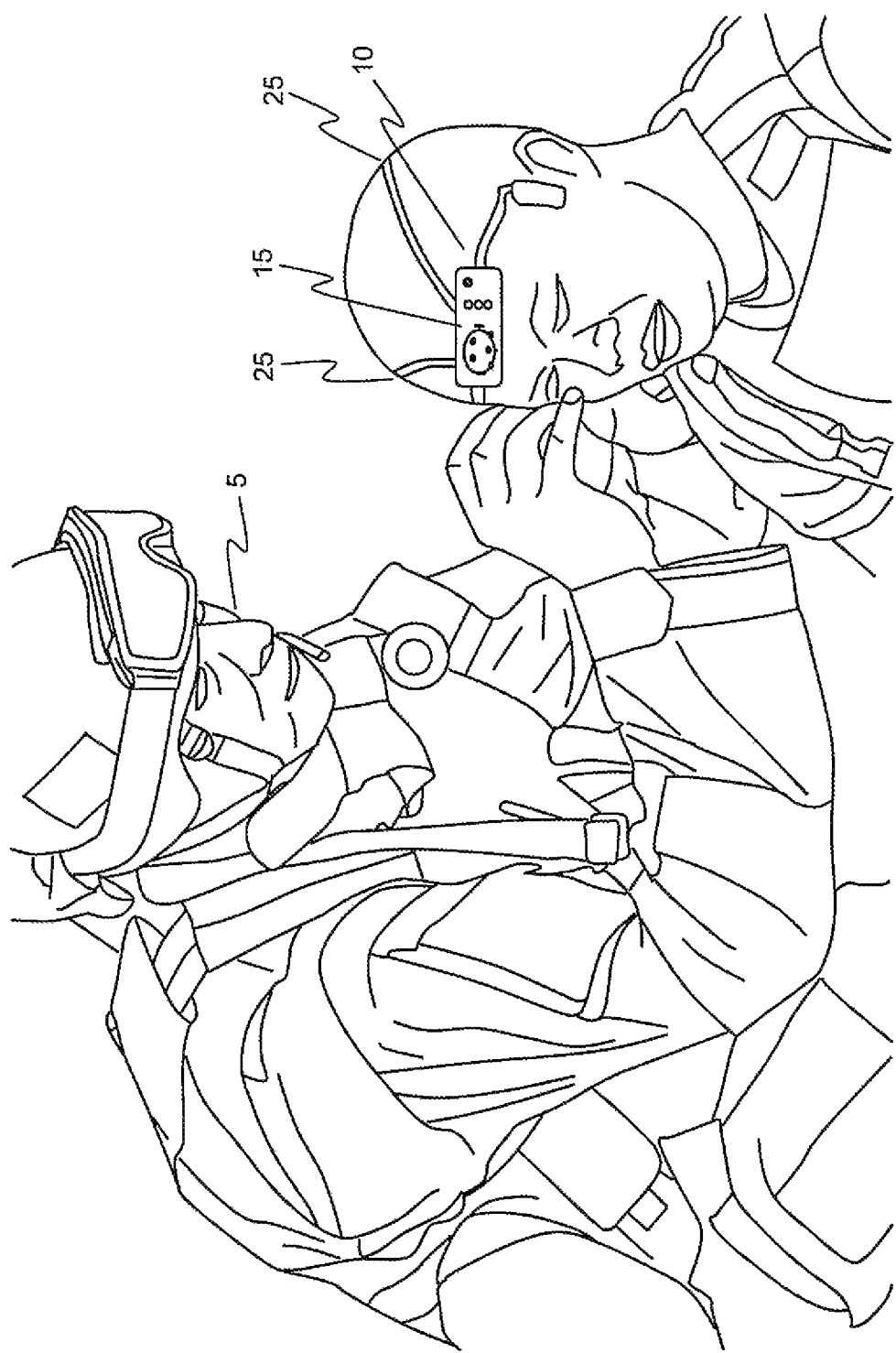
FIG. 1B. Depiction of a soldier applying the device having an integrated monitor to an injured subject in the field.
Figure 2A:
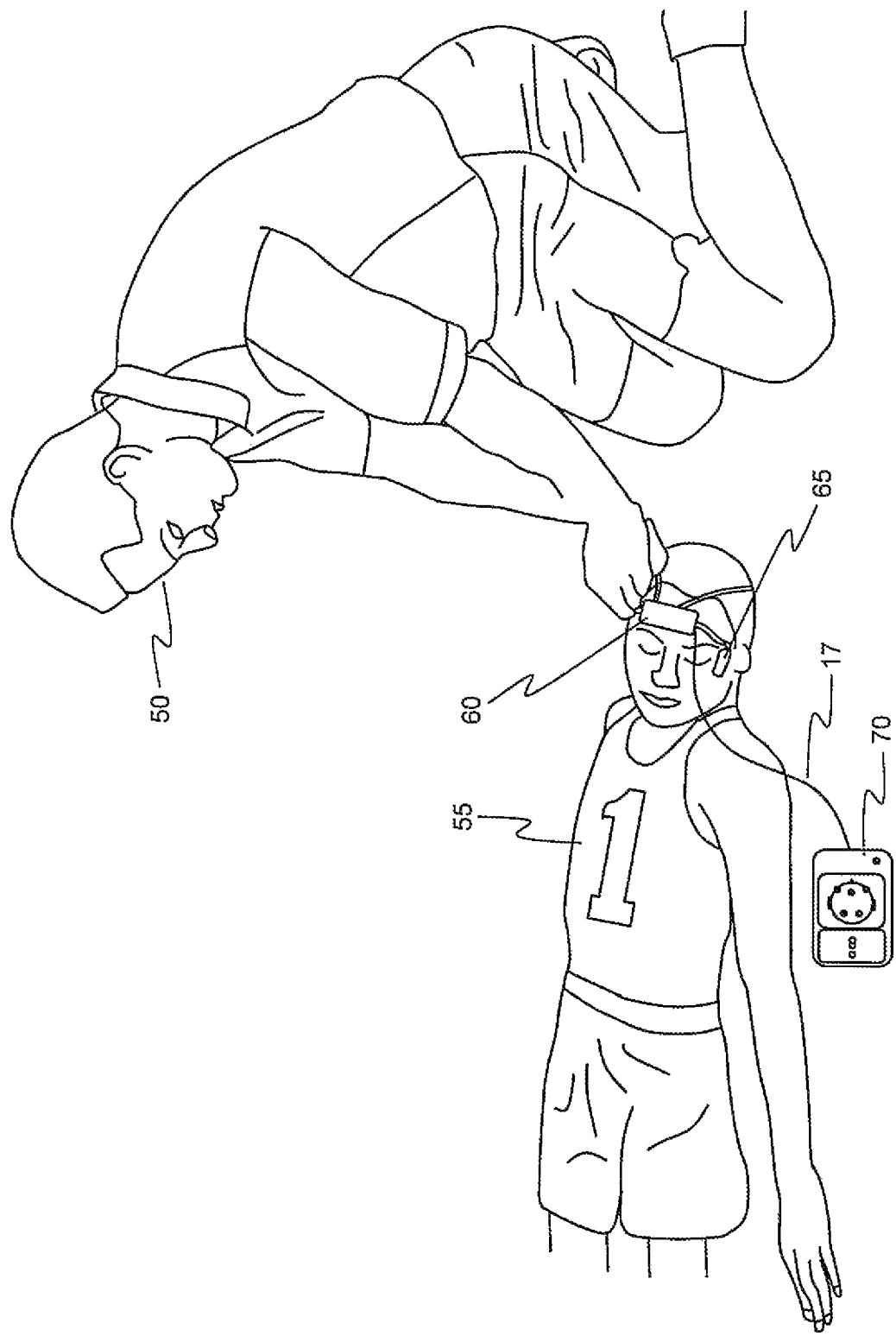
FIG. 2A. Depiction of a responder applying the device having a separate monitor to an injured subject in a sports setting.
Figure 2B:
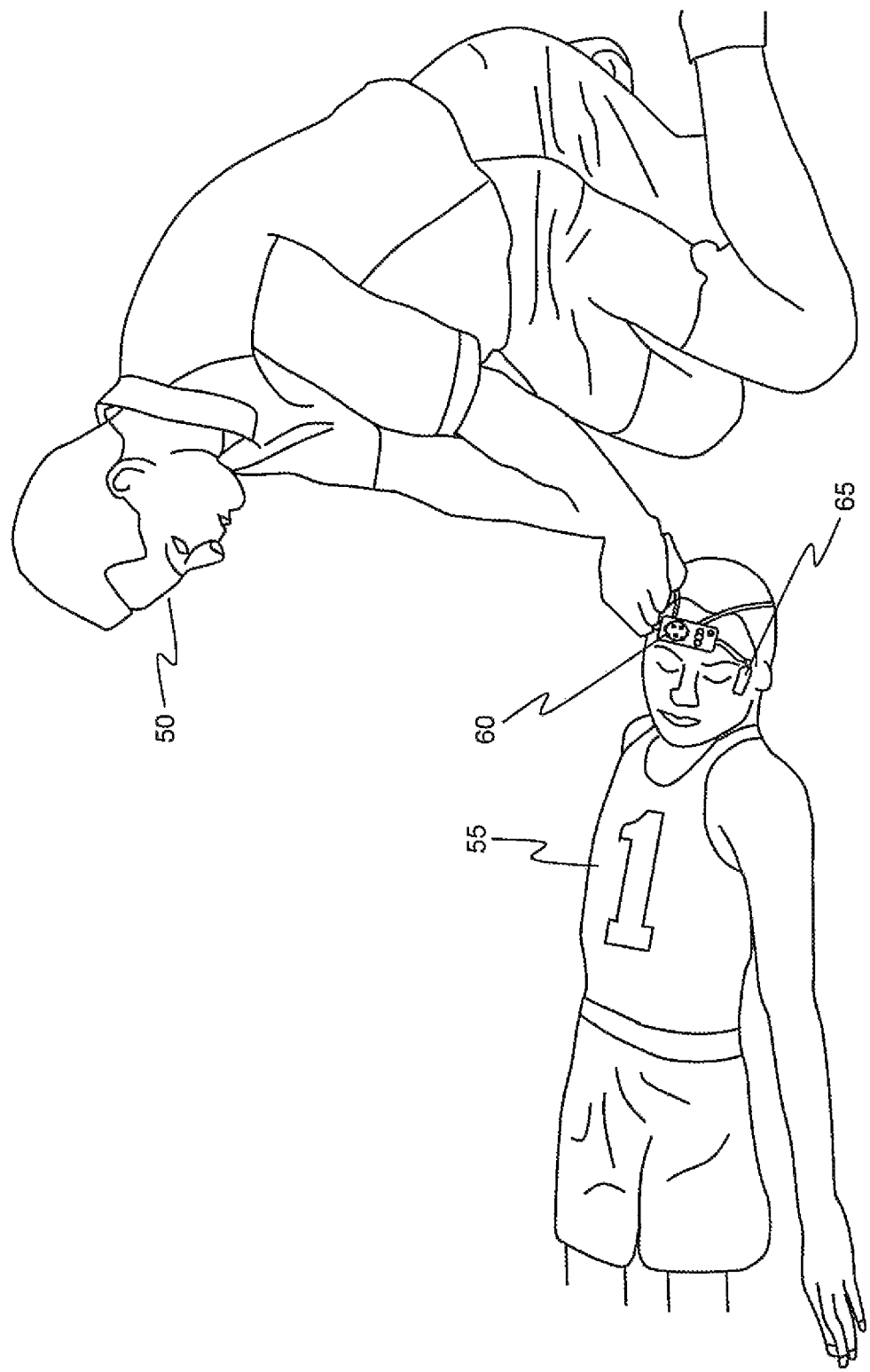
FIG. 2B. Depiction of a responder applying the device having an integrated monitor to an injured subject in a sports setting.
Figure 3A:
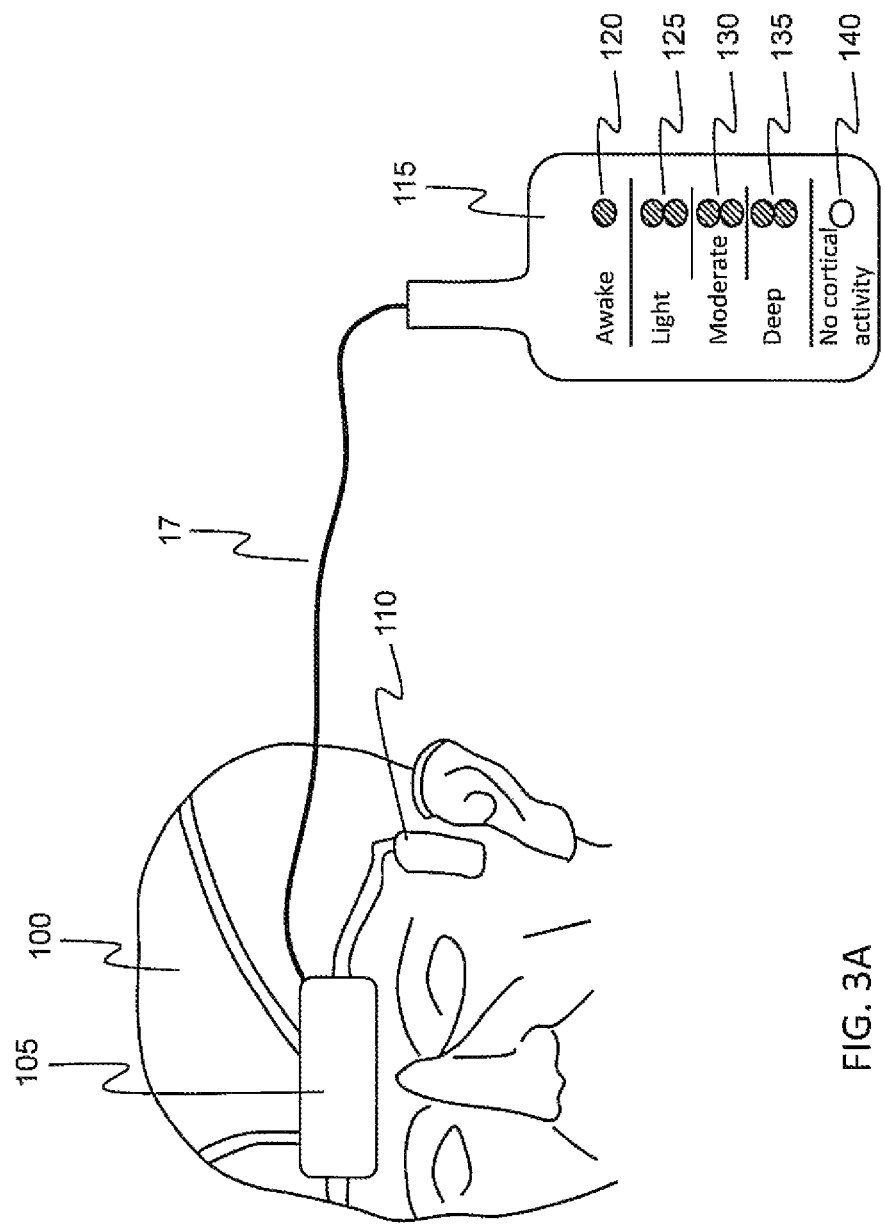
FIG. 3A. Close-up depiction of the device as applied to an injured subject's head with monitoring indicators on a separate monitor.
Figure 3B:
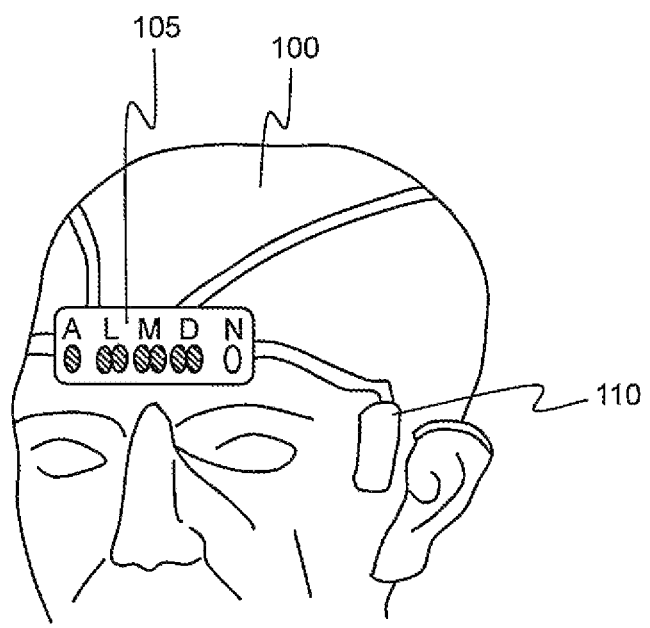
FIG. 3B. Close-up depiction of the device as applied to an injured subject's head with monitoring indicators on an integrated monitor.

Almost all embodiments of the present invention include a display, which may or may not be disposable. The display is designed to be small, rugged, and easily stored and transported until deployed. Once deployed, the display is preferably easily attached to the subject, his or her clothing or gear, carried in the subject's or a caregiver's gear, carried by an accompanying caregiver, or attached to a pole or other permanent or semi-permanent location where the system is integrated into a medical transport or evacuation vehicle. In some embodiments, the display may be integrated as part of the flexible substrate, as shown in FIGS. 1B, 2B, and 3B, rather than being a separate device as shown in FIGS. 1A, 2A, and 3A.

Preferably, the display provides a touch-screen interface for the caregiver to interact with the system, although other control means such as analog buttons, or a combination of screen output and analog or digital controls may be used. By small, it is intended that the surface area of the display is preferably less than 100 square inches. More preferably, the surface area of the display is less than 75 square inches. Still more preferably, the surface area of the display is less than 50 square inches. Even more preferably, the surface area of the display is less than 30 square inches. Even still more preferably, the surface area of the display is less than 20 square inches. More preferably still, the surface area of the display is less than 15 square inches. Still yet more preferably, the surface area of the display is less than 10 square inches.

By way of non-limiting example, in a preferred embodiment, the surface area of the display is about the size of a credit card. The display is preferably constructed of a material that is capable of withstanding harsh environments (e.g., extreme temperatures), strong forces (e.g., concussive explosions), and should be air and water tight (e.g., completely sealed against air, sand, water, and the like). Further, the screen of the display should be scratch and shatter resistant, or more preferably, scratch and shatter proof.

In some embodiments, the display may simply integrate light-emitting diodes (LEDs) as a means of displaying visual information to the user. In other embodiments, the display may be more complicated, such as a touch screen, which also provides a direct user interface. Also, a processor may be integrated in the display unit to process the EEG signals. This processor can be based on a reduced instruction set computing (RISC) microprocessor, or a digital signal processor (DSP). Preferably, the processor is a microprocessor sufficiently miniaturized to fit into the small device or display and provides little or no bulk or weight to the device. Further, particularly for TBI determination, the processor embeds algorithm(s) for making particular determinations, e.g., presence of seizure activity, EEG slowing, low cortical activity level, presence of EEG amplitude loss or cortical suppression. In a particular context-of-use, such as a far forward deployment, a trigger in any of these endpoints may point to the presence of TBI. In particular, the determinations are made based on at least one of several algorithms coinciding with the above described methods and steps, including, but not limited to, seizure detection, cortical suppression detection, EEG slowing detection, cortical activity level measurement, and the like. The algorithms can be used on a single EEG channel, two channels, or more, as needed. Processed information from two or more channels may be combined to improve the determination of the presence or absence of TBI. Other algorithms may be provided, including, but not limited to, those for providing measures such as spectral edge frequency (SEF) or the median edge frequency (MEF), or other methods based on entropy and/or bispectral analysis.

In many embodiments, the display also contains internal memory for storage of acquired and/or processed EEG signals, calculated data (e.g., EEG events such as seizure or suppression, indices, alerts, and the like), and/or logistical data (e.g., time, location, GPS coordinates, and the like). The internal memory may consist of a removable flash memory card such as an SD, miniSD, microSD, MMC, Compact-Flash, or the like. Alternatively, or in addition, the display may contain an internal, non-removable memory for such storage. In such embodiments, the non-removable memory may be read by connecting the display to another device by means of a cable, or by virtue of an incorporated USB-type attachment that may fold out of the display to be inserted directly into another device. Some embodiments may provide both non-removable and removable memory to provide redundancy in the data storage in the even that one of the memory components is destroyed, damaged or lost. Data from the memory may in some embodiments be transmitted by wired or wireless transfer using any of the protocols described in this application or known to those skilled in the art.

The display further preferably comprises an internal power source. Such internal power source furthers the ease and simplicity of use of the device by removing the need for power cables or cords, as well as the external power source. This also increases the portability of the device. Such internal power source may be a battery of any type known to those in the art that is suitable for the type of applications envisioned for the device, and that contain sufficient life to power the device from deployment until the subject is delivered to a location of higher echelon care and can be monitored by more permanent, robust equipment and caregivers. In addition to a battery, the display may incorporate a source of renewable or regenerative power, such as solar power to maintain the life of the display.

The combination of the flexible disposable substrate, which integrates the electrode array(s) and the acquisition electronics, and a disposable display such as the one represented in FIGS. 1B, 2B, 3B, and 6, constitutes a Disposable Brain Monitor (DBM). Disposability provides the advantages that it eliminates the need for cleaning, sanitizing, refurbishing (including re-gelling any gelled electrodes and recharging and/or replacing batteries), restocking, etc., and the costs associated therewith. Another major reason for disposability in medical device products that make contact with a subject or patient is infection control. If the DBM is used only once, it cannot transmit infectious agents to subsequent subjects or patients.

As used in this application, "disposable" does not merely mean "capable of being thrown away" or any such broad definition that would include most durable equipment or equipment having indefinite life. As disposability can be defined by several factors—cost, use, size, disposal safety—this application refers to the terms "cost-disposable," "use-disposable," "size-disposable," and "safety-disposable." A disposable device is preferably at least one of these, more preferably at least two of these, even more preferably at least three of these, and most preferably at least four of these.

"Use-disposable" refers solely to instruments intended for single use followed by proper disposal and thus designed or designated as "do not re-use," "single use," or "use only once."

"Cost-disposable" systems must be sufficiently low-cost in their manufacture (even if not comparatively low-cost in their ultimate sales price as an assembled system) to justify eventual disposability of the individual components. Preferably, all of the individual components of the DBM together cost less than $200. More preferably, they cost less than $100. Still more preferably, they cost less than $50.

Even more preferably, they cost less than $10. More preferably still, all of the individual components of the DBM together cost less than $5. All dollar amounts are in 2013 dollars as calculated by the Consumer Price Index (CPI) Inflation Calculator provided by the United States Department of Labor, Bureau of Labor Statistics, or as computed according to another reliable inflation index. Any system with an aggregate component cost of greater than $200 (adjusted for inflation from 2013 dollars) is excluded from being considered cost-disposable.

"Size-disposable" means being sufficiently small and lightweight as to make disposable easy, convenient, and practical. Any item or system heavier than 2 lbs. or larger than one foot in any dimension when configured for disposal is excluded from being considered disposable for the purposes of this application. Being "configured for disposal" includes being folded or crumpled or otherwise reduced in size as practicable without any special machinery (e.g., without a mechanical compactor, saw, etc.).

"Safety-disposable" means that disposal of the device or system as regular solid waste or as medical waste can be easily done in compliance with environmental and/or health laws and regulations in the jurisdiction where the device or system is disposed of in accordance with standard practices for disposal of solid waste or medical waste.

Preferably, disposable components of the present invention, including the DBM in any embodiments that include a DBM, are labeled or identified as disposable in accordance with ISO 15223 and/or EN 980 standards (e.g., with the numeral 2, within a circle with a 45° line through it). Further preferably, the methods or devices of the present invention include steps or functional and/or structural features which enforce disposability and prevent reconditioning or re-use of a DBM or other disposable components. Such steps could include a step of performing data acquisition and/or analysis for only one continuous finite period of time, and/or a step of disposal following a single use. Such functional and/or structural features could include a non-rechargeable, non-replaceable battery which possesses only enough charge for a single continuous use; electronic components and/or circuitry and/or software instructions embedded in such electronic components and/or circuitry which prevent and/or inhibit re-starting of data acquisition and/or processing for a second period of use following a first period of use which has been interrupted, in particular when one or more factors indicating attempted re-use are present, such as a detected removal of all electrodes from the skin, a detected stopping and restarting of the acquisition/processing system, a detected peeling of a previously applied DBM from a subject's skin, a detected replacement or attempted replacement or recharge or attempted recharge of a battery, a detected re-entering of certain subject or patient parameters (e.g., weight, age, etc.) that tend to indicate that a wholly new subject or patient is wearing or using the DBM, and so forth. Single-use could also be enforced by features such as making the DBM's flexible substrate such that it can be applied intact but cannot be removed intact. In such an embodiment, forces involved in removing the DBM by peeling or pulling work to break critical connections, such as between embedded electrode leads or in embedded traces between electronic components, rendering the DBM useless for any use subsequent to the first use. Another feature that would help to enforce non-reuse would be the lack of any connectors on the DBM or indeed any means of connecting the DBM to an external system, including an external electrode system and/or an external monitor or data transmission or storage system. That is to say, the only paths between the electrodes and the acquisition and processing electronics are self-contained in the DBM and inaccessible. This inaccessibility can be achieved by the appropriate embedding, covering and/or sealing of electrical paths and connections within the DBM, and can be enforced through some of the same means discussed above, e.g., with features that disintegrate the system upon tampering or attempted tampering, where the purpose of such tampering would be to gain access to embedded, covered, and/or sealed electrical paths or connections in order to achieve partial or total re-use of the DBM. Additional software features used in an computer system external to the disposable portion of the invention (including the display in embodiments that use a reusable display) that could be used to enforce disposability of the disposable portions include checking for a unique serial number or code associated with the disposable portion and refusing to connect to a disposable monitor, or process data from a disposable monitor, established as having been previously used, for example, by checking with a database which may be locally stored on the display or other computer system or may be remotely stored and accessed via the Internet or other network.

Features of DBM embodiments of the present invention that embed low-cost signal processing electronics directly within the disposable signal acquisition apparatus provide advantages not found in prior disposable or partially disposable devices. In some DBM embodiments of the present invention, the disposable embedded processing electronics processing acquired EEG signals to produce a reliable, easily-read, rapidly understood "go/no-go" type output: seizing/not seizing; normal/abnormal brain activity; conscious/unconscious; suppression/no suppression; level of alertness and/or sedation (such as awake/light sedation/moderate sedation/deep sedation/no cortical activity), etc. Unlike raw signal data, such as an EEG trace, this type of output is useful even to an untrained, unskilled first responder in assessing the presence or absence of brain injury, seizure, abnormal brain activity, level of consciousness or sedation, level of brain injury, etc. By thus making the entire DBM system so easy to apply and use, such embodiments of the present thus bring TBI, seizure, and sedation assessment into the realm of performance "anytime, anywhere, by anyone," in much the same way the invention of the automated external defibrillator (AED) made treatment of potentially life threatening cardiac arrhythmias performable by the layman. Embodiments that make the entire system disposable maximally reduce the complexity and increase the speed of use of such systems by eliminating the need to connect or mate (or disconnect or un-mate) disposable and non-disposable portions of the system. By eliminating these complexities, the discussed embodiments of the present invention cross a major chasm in required expertise and/or training in usage of the system by helping to make the system almost totally foolproof in its usage and operation.

In some embodiments of the present invention, the DBM may include an automatic, continuous electrode impedance checking ability. Traditional impedance checking techniques require the monitoring system to halt biosignal acquisition and monitoring in order to check and measure the impedance of a given electrode. However, continuous impedance checking, in the context of the present invention, means that impedance can be measured simultaneously with continued, uninterrupted monitoring and acquisition of the desired biosignal. In other words, the acquisition function of an electrode does not need to be halted in order to check the impedance of any given electrode. In order to continuously check electrode impedance, such embodiments require an alternating current source generator that is capable of progressively increasing and decreasing electrical current into the individual measurement electrodes. Preferably, the current supplied to the measurement electrodes is supplied at a known amplitude and frequency. Also preferably, the frequency of the supplied current is outside of the biological frequency of the physiological signal being monitored (herein referred to as the bio-band). Supplying the current outside the biological frequency for the signal from the electrode being measured prevents interference with the diagnostic signal—preventing perturbation of the measured physiological signal. For example, the typical biological frequency (bio-band) of EEG signals is from about 0.5 Hz to about 70 Hz, but can expand to between 0.125 Hz to about 120 Hz. Meanwhile, the typical bio-band for EMG signals ranges from about 30 Hz up into the kilohertz range. The maximum level of the impedance measurement current supplied further depends on the electrical instrumentation utilized as well as legal limits set with regard to patient care, depending on the application. The supplied current must be within the limits of the instrumentation so as not to overload the amplifiers and cause the system to fail. Also, regulations limit currents supplied to the human body to levels below 10 microamps.

Some embodiments of the present invention may preferably include an "automatic on" feature wherein the system automatically turns itself on and begins to perform signal acquisition, processing and analysis either upon the start of usage or application of the device or upon determining that the device's electrodes have been connected to the skin of a patient or subject. This "automatic on" could be enabled in any way known to a person skilled in the art using various mechanical or electronic techniques; one simple way is to include as part of a peelable sanitary electrode backing a battery connection interrupter, i.e., a thin insulating portion of the sanitary backing which inhibits the flow of battery power to the system until the sanitary backing is peeled off just prior to application of the electrode array to the skin of the patient or subject. Removal of the sanitary backing also displaces that portion of the backing which interrupts the flow of current from the battery to the rest of the system, thus activating the system and eliminating the need for any other type of activation button, mechanism or signal, which concomitantly reduces cost of the system and simplifies its use. This backing would also serve to protect the adhesive layer of the electrode array in adhesive patch embodiments of the present invention. Another way of providing an "automatic on" would be for the system to operate continuously, even when not in use, in a very low power impedance checking mode, but to switch to regular power consumption "on" mode once the system determines that all electrode connections are of sufficiently low impedance for use, indicating that the electrode array has been applied to the skin of a patient or subject. In embodiments of the system that employ an external, connectable monitor, the system may become activated by connecting the monitor to the disposable electrode array portion of the system. In such embodiments, the disposable electrode array may have no power supply of its own but may source all of its power from the external, connectable monitor, which in such cases is preferably reusable.

Once the electrical current being supplied to the first measurement electrode has reached the predetermined maximum stabilized current, the voltage resulting from the supplied current is measured across the system. The voltage and current values are known to the system and are used to calculate an electrical impedance of the first measurement electrode. Preferably, this voltage measurement and impedance calculation is carried out over a period of time of one cycle depending on the frequency. The resultant impedance value calculated for the first measurement electrode is compared against a threshold value to determine whether the electrode is providing as clear a signal as possible for accurate EEG or other physiological signal display. This threshold value is determined by the application as to the sensitivity necessary to provide a good physiological signal. If the electrical impedance calculated in the first measurement electrode is too high, then a technician or operator is notified and he or she decides what type of action is required to renew the quality of the signal. This process is described in greater detail in U.S. Patent Application Publication No. 2011/0295096 A1, which is incorporated by reference.

Additionally, in many embodiments, the DBM should have an artifact detection and/or removal system which differentiates between a normal (or abnormal) physiological brain activity and artifacts or noise caused by various sources of interference. The process of artifact detection is described in greater detail in U.S. Patent Publication No. 2011/0295142 A1, which is incorporated by reference.

Further, many embodiments of the present invention provide a cortical suppression detection function to monitor and notify the user when a subject's brain function is suppressed below a threshold level, or when the EEG signal amplitude drops below a certain level. Suppression may be indicative of severe brain trauma such as traumatic brain injury (TBI), oversedation or anesthesia over-dosing, or the like. In order to provide the suppression detection function, such embodiments may involve computing the first derivative of the physiological or sensor signal. Most embodiments utilize the first derivative, though some embodiments may use a higher derivative. Utilizing the first derivative rather than the raw (or filtered) EEG signals has been shown to remove baseline wandering and thus renders the analysis more accurate and reliable. The step of computing the first or higher derivative of the signal is performed on a processor, in real time, and substantially at the same time as the signal is being acquired. Substantially at the same time means that immediately as the signal is acquired by the circuitry and apparatus described above, the processor computes the appropriate derivative of that signal. Once the desired level of derivative has been computed, an epoch of predetermined size of the derivative of the EEG signal is analyzed using at least one suppression detection parameter, the at least one suppression detection parameter being used to detect suppression in the EEG signal. The suppression detection measure can be virtually any type of operator or algorithm which is capable of detecting the drastic changes in the EEG signal which may be representative of burst and/or suppression periods. Such suppression detection measures may include, but are not limited to the median absolute value, the peak-to-peak time measurement, root mean square (RMS), spectral measures, entropy measures, energy operators, and the like. Preferably, at least one suppression detection measure used is the median absolute value of the first derivative of the EEG signal. The median absolute value is a robust measure of the rate of change of EEG, is less sensitive to outliers, and corresponds with the visual recognition rules of suppression detection. Thus, as the EEG, or other physiological signal, is acquired, the processor first calculates the desired derivative of that signal, and essentially simultaneously computes at least the median absolute value of that first derivative signal. Next, such embodiments utilize the above calculated suppression detection measure(s) (e.g., median absolute value) for the detection of suppression periods in the EEG signal. If the above calculated suppression detection measure is below a predetermined threshold for a predetermined amount of time, then that particular epoch is determined to be suppression. Some embodiments include a step in which artifacts are detected and identified, and are not counted as periods of burst activity. These artifacts may be those that were not detected by the front-end filtering, or new additional artifacts that corrupt the signal after initial filtering. In this optional step, the present invention differentiates between such artifacts and burst activity. This means that the system does not count an aberrant artifact as burst activity and thus effect the detection of burst and suppression periods and their durations. This is another step to increase the accuracy of the invention in environments that create artifacts in the EEG signal. Some embodiments of the present invention further include a step by which the thresholds used for detecting a burst or suppression period are automatically relaxed or tightened based on environmental factors. For example, if the signal contains a particularly strong or high amplitude period of burst activity, the threshold may be relaxed so the results of the detection methods are not artificially skewed or misidentified. This process is described in greater detail in U.S. patent application Ser. No. 13/216,755, which is incorporated by reference.

Some embodiments may utilize a bilateral monitoring method to measure EEG signals from the two hemispheres (left and right) of a subject's brain independently and simultaneously. In such embodiments, at least three electrodes (or sensors) are utilized, one measurement EEG electrode to measure EEG signals of the left hemisphere, one measurement EEG electrode to measure the EEG signals of the right hemisphere, and one reference electrode. Such embodiments, preferably, the physiological electrodes or other sensors are placed on the subject's head with at least one measurement electrode on each side of the subject's head (i.e. left and right sides as divided by the sagittal physiological plane). Also preferably, at least one reference electrode needs to be placed in order to obtain and measure the differential EEG signals from each of the measurement electrodes. In order to be able to compare the signals from the left and right hemispheres of the subject's brain, the reference electrode is preferably placed as close as possible to the center of the subject's head. This placement should coincide with the location of the longitudinal fissure. When placed as close to the longitudinal fissure as possible, the reference electrode will receive EEG signals from both hemispheres of the subject's brain, and therefore produces a common signal that can be used to create accurate and comparable differential calculations between the EEG signals measured from each individual brain hemisphere. This process is described in greater detail in U.S. Patent Application Publication No. 2011/0130675 A1, which is incorporated by reference.

Many embodiments of the present invention include brain function monitoring algorithms. The brain function monitoring algorithms use the acquired EEG signals, and process them specifically to determine the subject's brain state, presence and/or level of injury (e.g., TBI) or other abnormal function (e.g., seizure). Examples of some algorithms that may be utilized for brain dysfunction detection are included in U.S. patent application Ser. No. 12/259,652, and U.S. patent application Ser. No. 13/731,315, which are herein incorporated by reference, though other similar algorithms known to those skilled in the art may be used as well. In many embodiments, the same or other algorithms may include the means to determine the level of cortical activity of the subject in order to automatically adjust and control the delivery of drugs to maintain a desired level of sedation, or a desired depth of anesthesia.

In many embodiments of the present invention, the display device may be substituted for an Integrated Monitoring and Infusion System (IMIS). The IMIS comprises many of the above components in order to perform signal acquisition, pre-processing, analysis, make status determinations, monitor a subject's brain function, and to display various signals and/or indicators. In other words, the IMIS essentially comprises all of the display device functions and features, but also incorporates several additional components, features, and capabilities to perform additional functions of determining a desired level of cortical activity, monitoring the subject's cortical activity level, and automatically adjusting the delivery of sedative, anesthetic, and/or analgesic drugs to maintain that desired level of cortical activity. Such system can also be used to drive a patient to a new cortical activity target that is more adequate for the clinical situation.

The IMIS embeds one or more control algorithms into a control module, which allows for closed-loop operation; however, in case of adverse conditions, partial or total system failures, or other system errors, the closed-loop function may be overridden and the system controlled manually by the caregiver. By closed-loop, it is intended that the system operate automatically, continuously, and without human interaction once the system has been applied to a subject and set into motion. The control module is designed to regulate the infusion rates of an intravenous hypnotic (sedation or anesthetic) and optionally also an opioid (analgesic) drug. In a preferred embodiment, both a hypnotic and an analgesic drug are administered by individual infusion pumps (described below). The administration of both drugs is typically required to provide a state of balanced anesthesia to the subject, where the subject neither perceives nor recalls noxious stimulation. The controller uses a measurement of the cortical activity of the subject. This measurement can be based on spectral or bispectral analyses, or preferably using wavelet analysis, or any of the other measurements described above, either individually, or in combinations thereof. Ideally, an index of cortical activity used in a closed-loop application should introduce no delay and be linear and time-invariant (LTI) across its whole operating range.

One such EEG index that complies with these requirements is the $WAV_{CNS}$ index, developed by some of the applicants. The $WAV_{CNS}$ index quantifies the effects of anesthesia drugs on the brain using wavelet analysis of frontal EEG signals. It is expressed in a 100-0 scale where "100" represents the awake conscious state and "0" represents the total suppression of cortical activity. A suitable state for performing surgical procedures (i.e., general anesthesia) is between 40 and 60, while a sedated subject is between 60 and 80. A conscious subject produces a value well above 80, while subjects induced into deep coma (e.g., for stroke surgery or refractory seizure control) would have $WAV_{CNS}$ values below 10. Wavelet analysis is a powerful signal processing technique particularly well suited for non-stationary EEG signals. The wavelets are able to simultaneously and rapidly characterize changes in both time and frequency, which more traditional spectral analyses are typically unable to track timely. The $WAV_{CNS}$ rapidly captures fast changes in cortical activity. Another particularly important advantage of the $WAV_{CNS}$ quantifier lies in its consistent and well-defined transient behavior during patient state changes. The only dynamic difference between the physiological effect and its quantification through the WAV$_{CNS}$ algorithm is due to the post-analysis trending filter, which is well-defined, linear and time-invariant. Preferably, feedback quantities used for regulation (i.e., in closed-loop systems) should be LTI to ensure that their input-versus-output relationship can be accounted for by the controller, and that they do not add uncertainty. An ideal sensor for control should not introduce non-linearities (especially discontinuities) and should not introduce (unknown and variable) additional delay. From a control perspective, cortical activity sensors that are LTI represent the best-case scenario. Non-LTI sensors, on the other hand, introduce uncertainty in the system, which leads to instability if not properly accounted for, and/or a reduction in the controller performance. A non-LTI brain function monitor used in a closed-loop application could result in an inaccurate and/or delayed EEG interpretation during sudden changes in cortical activity (due to, e.g., a sudden change in drug administration or change in surgical stimulation). Consequently, in embodiments performing automated sedation control, the overall regulation of anesthetic delivery would be more prone to instability and therefore less safe. The existence of a reliable mathematical function relating a physiological change in drug effect and its corresponding quantification by the WAV$_{CNS}$ means that the effect of the monitoring technology can be fully accounted for in the controller. In addition, it is important that the cortical activity sensing technology does not introduce additional uncertainty in the system, which will ultimately provide better closed-loop performances. Though the WAV$_{CNS}$ index is preferred, other indexes or indices describing a subject's brain or cortical activity can be envisioned and used in conjunction with the present invention, for example the BIS index.

While a single measure can be used, it may be preferable to use a bilateral measure of the cortical activity in order to provide redundancy in the system. In healthy individuals, the left and right hemisphere measures should be equivalent, e.g., in terms of WAV$_{CNS}$, to within a defined degree or threshold. The caregiver could then set the system to operate based on the right hemisphere measure, or the left hemisphere measure, individually. Preferably, the system uses both measures, and outputs a warning to the caregiver and/or automatically adjusts the infusion of hypnotic and/or sedation drugs (in some embodiments) when both measures are significantly different. Preferably, such warnings and/or automatic control are triggered when the difference between the left and right hemisphere measures is greater than 5 percent. More preferably, the warning and/or controls are triggered when the difference is greater than 10 percent. Still more preferably, the warning and/or controls are triggered when the difference is greater than 12 percent. Even more preferably, the warning and/or controls are triggered when the difference is greater than 15 percent. Even still more preferably, the warning and/or controls are triggered when the difference is greater than 20 percent. Such significant difference could be the result of heavy artifact activity in one channel, or an existing or developing neuro-pathology. Alternatively, the control module may continuously assess the quality of the EEG signals from both channels, and automatically use the best channel for its feedback measure. Alternatively, in other embodiments, the system may average both measures in order to further limit the measurement noise.

The control module then calculates the difference between a predetermined setpoint defined by the caregiver or preprogrammed into the system, and the feedback measure. A control algorithm will then calculate an adequate modification of the infusion rates of either one or both drugs, either using a standard proportional-integrative-derivative (PID) control structure, or a more complex control structure based on robust control methods to guarantee stability in view of subject variability. A standard PID is a control loop feedback system that calculates an "error" value as the difference between a measured variable and a desired (predetermined) setpoint using at least three constant parameters: proportional error value, integral error value, and derivative error value. These three parameters are then weighted and summed and that sum is used to automatically adjust the infusion rates to minimize the error value.

In a preferred embodiment, a robust controller is specifically tuned to remain stable in view of a certain degree of variability. In some instances, the expected amount of subject variability for which the controller needs to account can be reduced by providing or inputting some subject-specific information to the system, such as the subject's age, weight, height, gender, ethnicity, etc. via an input or interface device or component. Based on this information, the robust controller can be more aggressive.

In some instance, a robust PID controller can be designed to effectively account for patient variability in such a way that a unique controller can be used for a wide population of patients. Patient variability is probably the most challenging aspect in "closing the loop." Quantifying this variability and expressing it as a system uncertainty is a first step in order to prove the stability of the controller when closing the loop. Once a robust design is achieved, performance can be assessed to verify that it meets clinical expectations.

Quantifying Patient Variability

To quantify the patient variability, it is useful to have carried out the identification of pharmacokinetic (PK) and pharmacodynamic (PD) drug models covering the patient population of interest. Such models can be found in the literature. For example, some of the inventors have published a paper (S. Bibian, G. A. Dumont, M. Huzmezan, et al., "Patient variability and uncertainty quantification in Anesthesia: Part I—PKPD Modeling and Identification", Proceedings of the 6$^{th}$ IFAC Symposium on Modeling in Biomedical Systems, September 2006), which is incorporated by reference, and which provides 44 Propofol patient models.

Figure 14A:
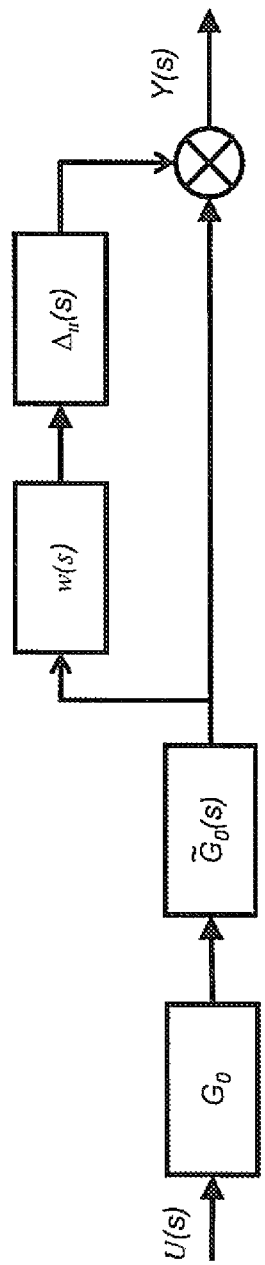
FIGS. 14A-P. Various graphs, charts and data representing test results and models for the system, including: A) unstructured uncertainty expressed in a multiplicative framework; B) representation of frequency domain uncertainty in the Nyquist map; C) optimization of the uncertainty radius; D) cases for uncertainty radius optimization; E) difference between unstructured uncertainty bounds and model constrained uncertainty bounds; F) Nyquist representation of some of the Propofol Models; G) optimal nominal model Nyquist path for different models; H) relative uncertainty for normo-volemic patients (blue line) and for both normo- and hypo-volemic patients (red line); I) robust stability condition check; J) robust Stability condition check for model set including hypovolemic models; K) patient model #10 with additional 20% increase in drug sensitivity—nominal controller; L) patient model #8 with additional 20% increase in drug sensitivity—nominal controller; M) patient model #10 with severe hypovolemia—conservative controller; N) patient model #10 with severe hypovolemia—nominal controller; O) patient model #10 with additional 20% increase in drug sensitivity—nominal controller with Smith Predictor; and P) patient model #10 with severe hypo-volemia—conservative controller with Smith Predictor.

Based on the Propofol models identified in Bibian et al., an unstructured uncertainty framework, where only the overall uncertainty in terms of the gain and phase of the system is defined, can be used to mathematically capture the uncertainty. The unstructured framework is usually selected when the model structure itself is poorly defined, or when the uncertainty cannot be expressed as parametric uncertainty. Consider a system G(s) for which some uncertainty bounds exist. A common approach is to model the uncertainty using a structure as depicted in FIG. 14A, which can be expressed as:

$$G(j\omega)=G_0 \cdot \tilde{G}(j\omega) \cdot (1+w(j\omega) \cdot \Delta_u(j\omega)) \quad (1)$$

where $\|\Delta_u(j\omega)\|<1$, $\tilde{G}_0(j\omega)$ is the normalized nominal model for the system, and $G_0=\|\tilde{G}_0(j\omega=0)\|$ is the steady state gain of the system. The weight function $w(j\omega)$ quantifies the magnitude of the unstructured uncertainty, while $\Delta_u(j\omega)$ expressed the uncertainty as a unity disk in the Nyquist plot. The multiplicative uncertainty gain $w(j\omega)$ is also referred to as relative uncertainty.

Figure 14B:
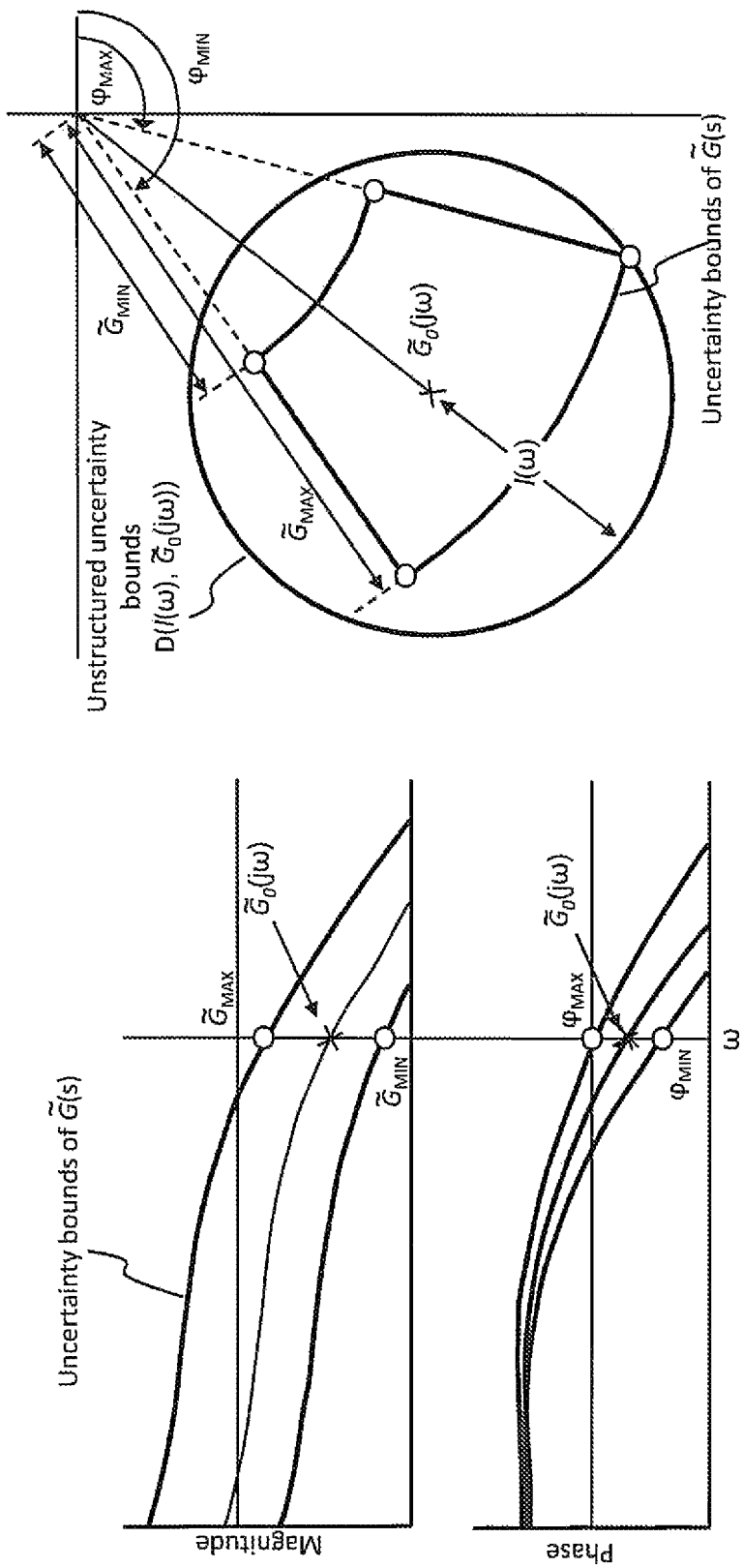

To better understand this concept, an example is presented in FIG. 14B. Assuming that the uncertainty bounds of $G(j\omega)$ are defined in the frequency domain and that a nominal model $G_0(j\omega)$ exists, and by mapping the frequency domain information into the complex Nyquist plane, the uncertainty at each frequency ω can be represented as the section of a ring centered at the origin. The outer and inner radii of the ring are defined by the uncertainty magnitudes $\tilde{G}_{MIN}=G_{MIN}/G_0$ and $\tilde{G}_{MAX}=G_{MAX}/G_0$, while the section is defined by the uncertainty angles $\varphi_{MIN}$ and $\varphi_{MAX}$.

To quantify the uncertainty according to the multiplicative uncertainty framework, the disk $\mathcal{D}$ is further defined as centered on $\tilde{G}_0(jw)$ and of radius $l(\omega)$. This circle is the smallest circle centered on $\tilde{G}_0(j\omega)$ and which contains all of the original uncertainty surface. The multiplicative weighting function is thus defined as:

$$\|w(j\omega)\| = \frac{l(\omega)}{\|\tilde{G}_0(j\omega)\|} \quad (2)$$

It is important to note that the uncertainty quantified by (1) considers a larger uncertainty surface than the one originally defined from the frequency domain. A limitation of the method is therefore that its representation of the frequency domain uncertainty can be very conservative, mostly if the center of the disk $\tilde{G}_0(j\omega)$ is located close to the edges of the ring section. A control design based on the uncertainty defined by the disk $\mathcal{D}(l(\omega), \tilde{G}_0(j\omega))$ may thus be unnecessarily conservative.

Figure 14C:
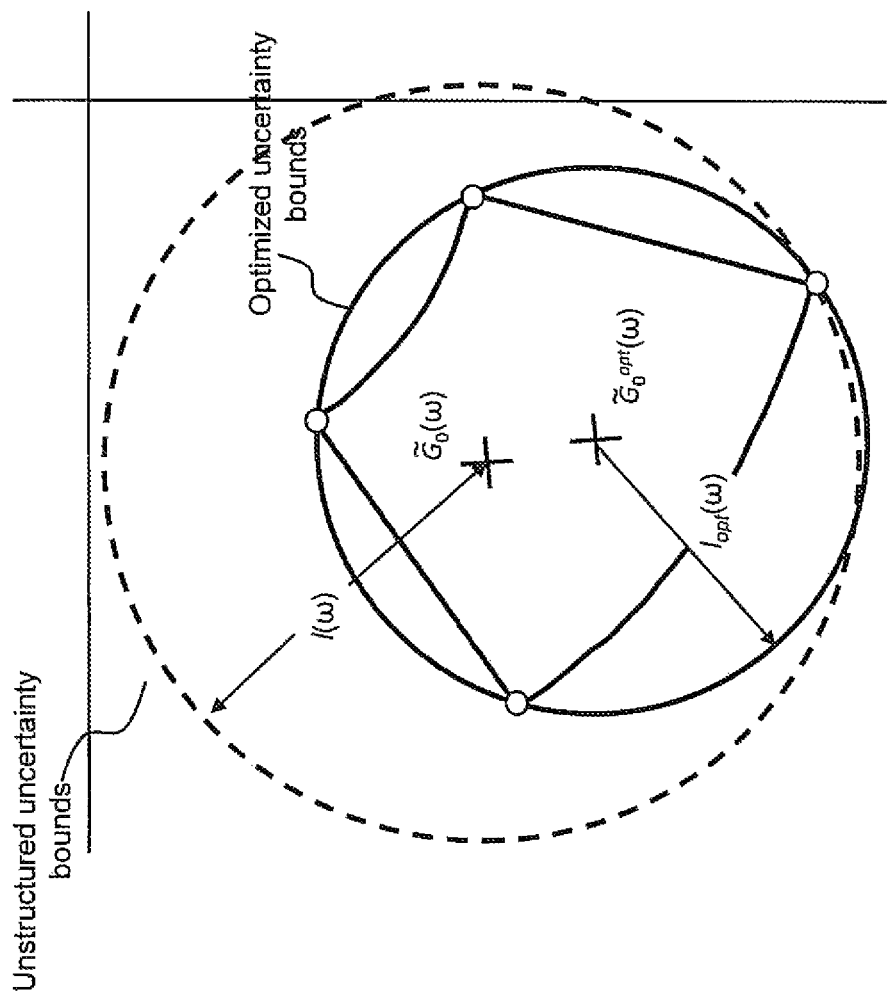

A simple way to reducing the uncertainty is then to minimize $l(\omega)$ by selecting the best location for the center of the uncertainty disk. In other words, this leads to the optimization of the nominal model $\tilde{G}_0$; see FIG. 14C. Note that this would still be a conservative characterization of the frequency domain uncertainty.

A first step towards the optimization of the nominal model is to determine the optimal Nyquist path for $\tilde{G}_0^{opt}(j\omega)$. The 4 following relevant coordinates are defined:

$$C_1 = \begin{bmatrix} x_1 = \tilde{G}_{MAX} \cdot \cos(\varphi_{MIN}) \\ y_1 = \tilde{G}_{MAX} \cdot \sin(\varphi_{MIN}) \end{bmatrix} \quad (3)$$

$$C_2 = \begin{bmatrix} x_2 = \tilde{G}_{MAX} \cdot \cos(\varphi_{MAX}) \\ y_2 = \tilde{G}_{MAX} \cdot \sin(\varphi_{MAX}) \end{bmatrix}$$

$$C_3 = \begin{bmatrix} x_3 = \tilde{G}_{MIN} \cdot \cos(\varphi_{MAX}) \\ y_3 = \tilde{G}_{MIN} \cdot \sin(\varphi_{MAX}) \end{bmatrix}$$

$$C_4 = \begin{bmatrix} x_4 = \tilde{G}_{MIN} \cdot \cos(\varphi_{MIN}) \\ y_4 = \tilde{G}_{MIN} \cdot \sin(\varphi_{MIN}) \end{bmatrix}$$

These coordinates mark the four corners of the ring. Depending on the phase uncertainty, the three cases depicted in FIG. 14D can be distinguished.

CASE 1 ($\varphi_{MAX}-\varphi_{MIN}<\pi$): in this case, it is possible to find a circle $\mathcal{C}$ that circumscribes the ring section. The origin $C_{cir}$ of $\mathcal{C}$ is located at the intersection of the perpendicular bisectors of the line segments $\{C_1, C_2\}$ and $\{C_2, C_3\}$ (or $\{C_1, C_4\}$). This can be analytically expressed as:

$$C_{cir} = \begin{bmatrix} x_{cir} = \frac{b''-b'}{a'-a''} \\ y_{cir} = a' \cdot \frac{b''-b'}{a'-a''} + b' \end{bmatrix} \quad \text{where:} \quad (4)$$

$$\begin{bmatrix} a' \\ b' \end{bmatrix} = \begin{bmatrix} \frac{x_2-x_1}{y_1-y_2} \\ \frac{1}{2} \cdot \frac{y_1^2-y_2^2-x_2^2+x_1^2}{y_1-y_2} \end{bmatrix}, \text{ and} \quad (5)$$

$$\begin{bmatrix} a'' \\ b'' \end{bmatrix} = \begin{bmatrix} \frac{x_2-x_3}{y_3-y_2} \\ \frac{1}{2} \cdot \frac{y_3^2-y_2^2-x_2^2+x_3^2}{y_3-y_2} \end{bmatrix}$$

In most cases, the circumscribing circle minimizes the uncertainty radius. However, if the phase uncertainty covers a larger span than the gain uncertainty (a "thin" ring), the center point of the line segment $\{C_1, C_2\}$ may yield a smaller uncertainty circle (see the second case in FIG. 14D). In general, the optimal center is defined as:

$$\begin{cases} C_{opt} = \begin{bmatrix} x_{cir} \\ y_{cir} \end{bmatrix} & \text{if: } \frac{\sqrt{x_{cir}^2+y_{cir}^2}}{\sqrt{(x_1+x_2)^2+(y_1+y_2)^2}} \leq \frac{1}{2} \cdot \\ C_{opt} = \begin{bmatrix} \frac{x_1+x_2}{2} \\ \frac{y_1+y_2}{2} \end{bmatrix} & \text{if: } \frac{\sqrt{x_{cir}^2+y_{cir}^2}}{\sqrt{(x_1+x_2)^2+(y_1+y_2)^2}} > \frac{1}{2} \cdot \end{cases} \quad (6)$$

Figure 14D:
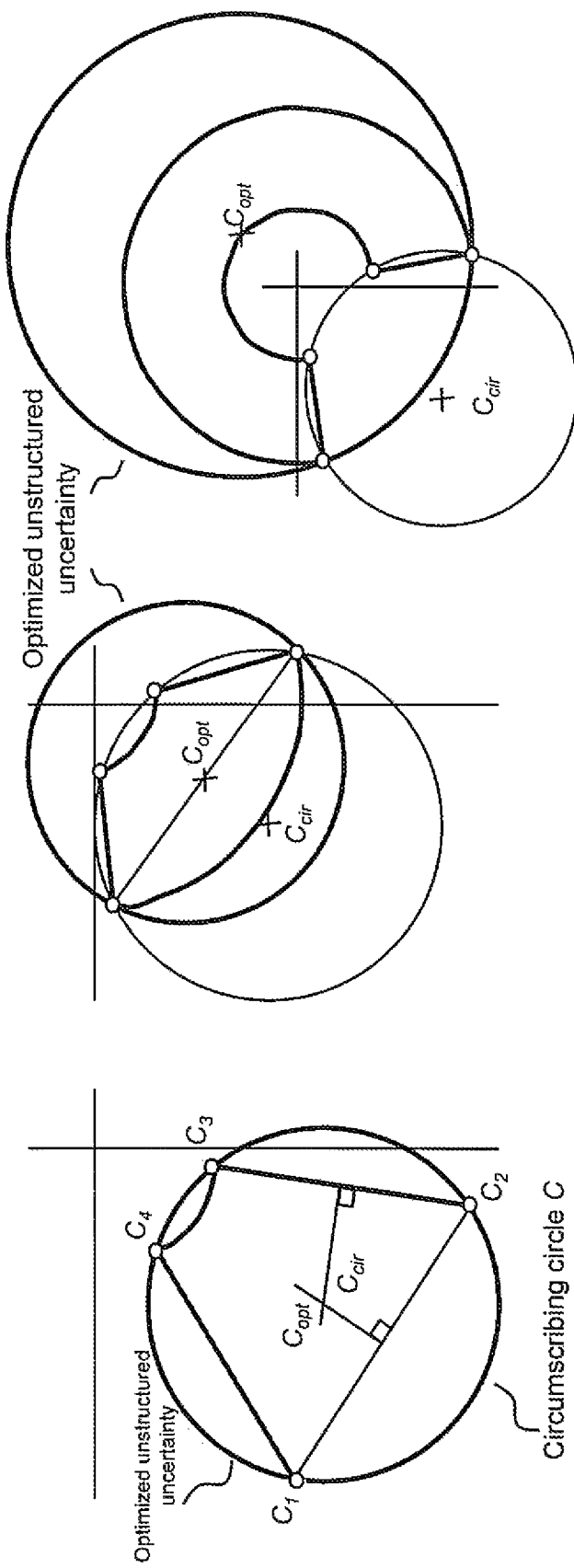

CASE 2 ($\pi<\varphi_{MAX}-\varphi_{MIN}<2\cdot\pi$): when the phase uncertainty reaches 180 degrees, (4) yields the center of the circle that circumscribes the complimentary ring section (third case in FIG. 14D). The center of the minimizing circle is opposite to $C_{cir}$ and located on the inner radius of the ring:

$$C_{opt} = \begin{bmatrix} -\frac{\tilde{G}_{MIN}}{\sqrt{x_{cir}^2+y_{cir}^2}} \cdot x_{cir} \\ -\frac{\tilde{G}_{MIN}}{\sqrt{x_{cir}^2+y_{cir}^2}} \cdot y_{cir} \end{bmatrix} \quad (7)$$

CASE 3 ($\varphi_{MAX}-\varphi_{MIN}\geq 2\cdot\pi$): in this trivial case, the ring section becomes a complete ring. As such, the center of the circle can be located anywhere on the inner edge of the ring, in particular:

$$C_{opt} = \begin{bmatrix} \tilde{G}_{MIN} \cdot \cos\left(\frac{\varphi_{MIN}+\varphi_{Max}}{2}\right) \\ \tilde{G}_{MIN} \cdot \sin\left(\frac{\varphi_{MIN}+\varphi_{Max}}{2}\right) \end{bmatrix} \quad (8)$$

Note: this analysis must be carried out for each frequency ω of interest. This results in the definition of an optimal Nyquist path $C_{opt}(j\omega)$.

Figure 14E:
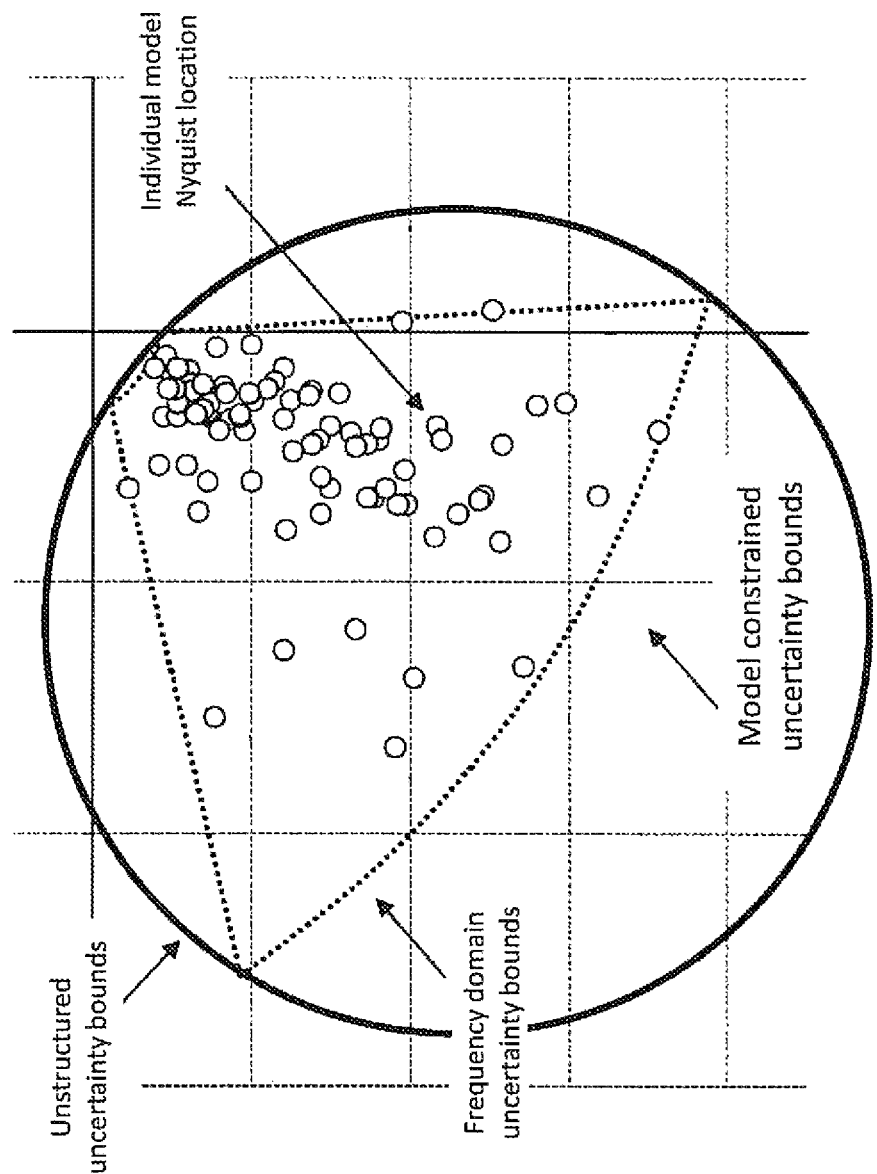

Using a practical example can show that the circle $\mathcal{C}$, as defined above, is in fact still fairly conservative, even if its origin (i.e., nominal model) is optimized as described above, as represented in FIG. 14E. In this example, the circle $\mathcal{C}$ was optimized to fit the frequency domain uncertainty bounds using the optimization method discussed above. However, there exists another circle $\mathcal{C}'$ that contains all the individual models, and of much smaller radius than e. Clearly, this new circle is sufficient to capture all of the uncertainty in the models. Similarly than in the previous discussion, the goal is to find the center of the circle that contains all of the individual models. It is sufficient to find the two models that are the most apart, ie., which distance from one another is larger than to any other model. These two models define the diameter of the circumscribing circle $\mathscr{C}$'. The center of the circle is the center of the segment defined by these two points, and the uncertainty radius equals half of the distance between the two points. An iterative process is required to find the two extremes.

Figure 14F:
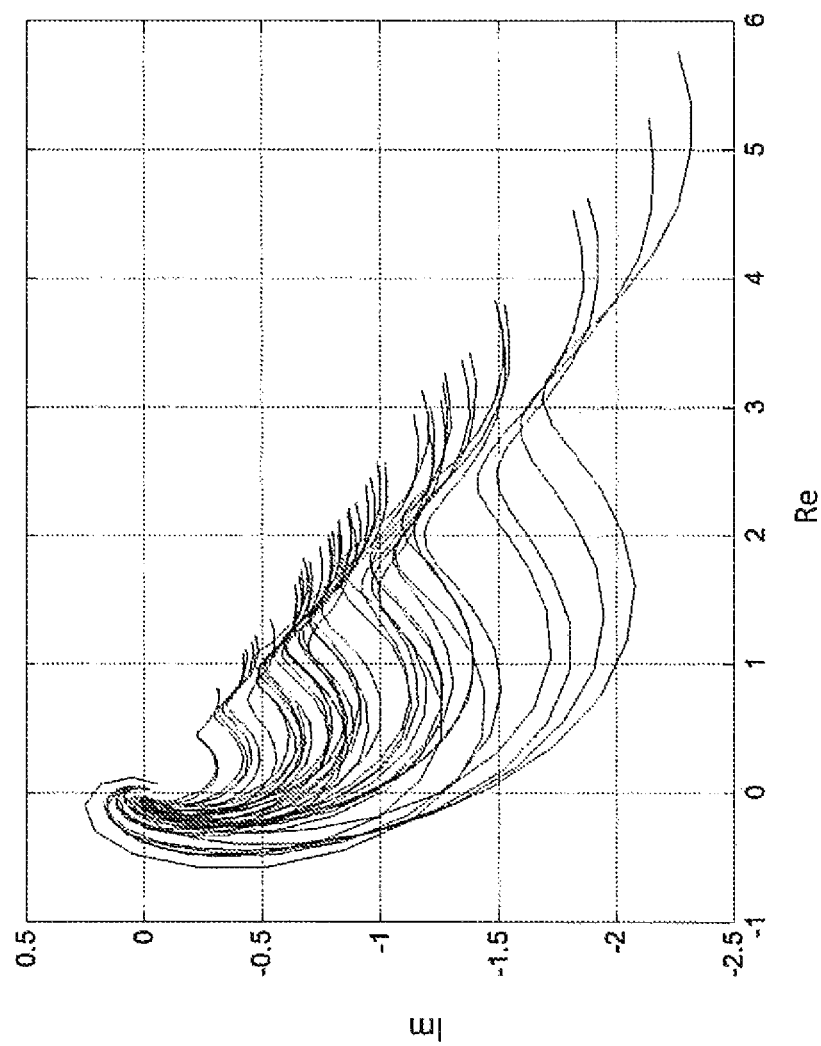
Figure 14G:
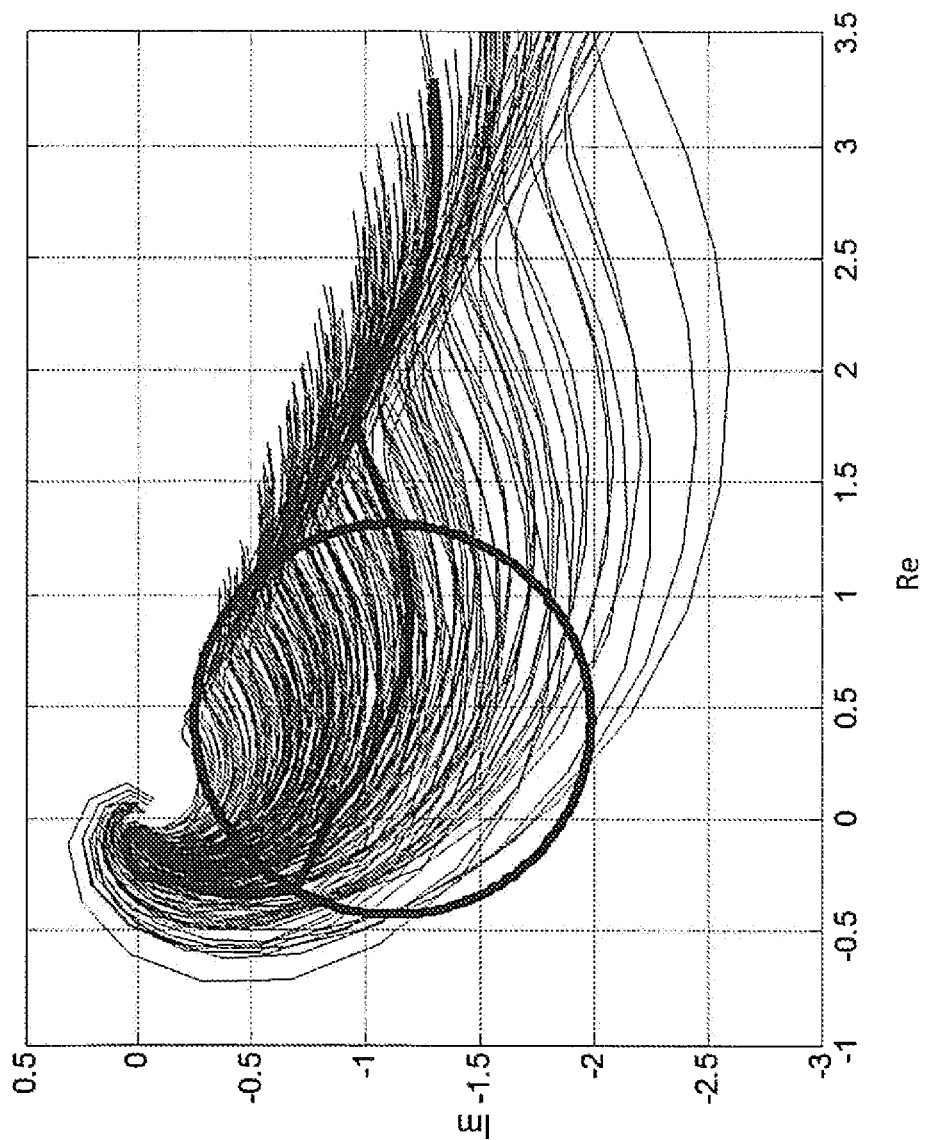

By way of example, the uncertainty optimization method discussed above was applied to the 44 Propofol models published in Bibian et al. FIG. 14F shows a representation of the Nyquist paths of the some patients' models. This graph shows the large amount of gain uncertainty in the effect of Propofol on a patient cortical activity. Using the uncertainty optimization method, an optimal Nyquist path can be defined for the nominal model; see FIG. 14G. The optimum unstructured uncertainty circle can then be calculated for each frequency along the nominal model, as shown below for ω=0.01 rad/sec. This circle is the smallest circle encompassing the whole uncertainty. The norm of the relative uncertainty weight $\|w(j\omega)\|$ can be calculated as the ratio between the uncertainty circle radius and the norm of the optimized nominal model. In this particular case, the obtained results are displayed in FIG. 14H. This is actually an important result. Any system presenting a relative uncertainty gain above 1 cannot be tightly controlled since the uncertainty disk contains the Nyquist origin, i.e., here exist models for which the open loop gain is 0, meaning that no control action can have any effect on the output. Based on this result, the controller bandwidth cannot extend much beyond 0.02 rad/sec, where the relative uncertainty abruptly increases after a small dip. The same analysis has been added when considering models of severe hemorrhagic shock. If one were to design a single controller capable of handling the full uncertainty spectrum, adding hypo-volemia adds significant limitations on the controller performance as the relative uncertainty margin is strongly reduced.

The second important information brought by the norm of the relative uncertainty weight is about robust stability which is the ultimate goal of this design work. In fact, robust stability implies that the complementary sensitivity function T(jω) defined as:

$$T = \frac{C \cdot G_0^{opt}}{1 + C \cdot G_0^{opt} \cdot H}, \quad (12)$$

and where H(jω) is the sensor dynamics, complies with the RS condition:

$$\|T\| < \frac{1}{\|w\|} \quad (13)$$

Complying with the RS condition ensures the stability of the system, but not its performance. In fact, there exist one or more patient models which would remain marginally stable if the norm of the complementary sensitivity function equals the inverse of the norm of the relative uncertainty. A number of other patient models would exhibit strong decaying oscillation for setpoint changes, or when compensating for disturbance. It is therefore preferably to keep the norm of T(jω) at least just below the inverse of $\|w(j\omega)\|$. A margin of 1% should be adequate and may represent a good starting point.

Controller Design

Once the uncertainty is well characterized, the controller parameters can be tuned to guarantee that the RS condition is respected. For simplicity, controller PID controller is considered, such as:

$$C = K \cdot \left(1 + \frac{1}{\tau_i \cdot s} + \tau_d \cdot s\right) \quad (14)$$

This structure provides error-free regulation in steady state through the integral action, as well as additional stabilization through the derivative action. This type of controller is easy to implement and tune, and well adapted to stable high order processes with long time delays, which is the case here.

Figure 14H:
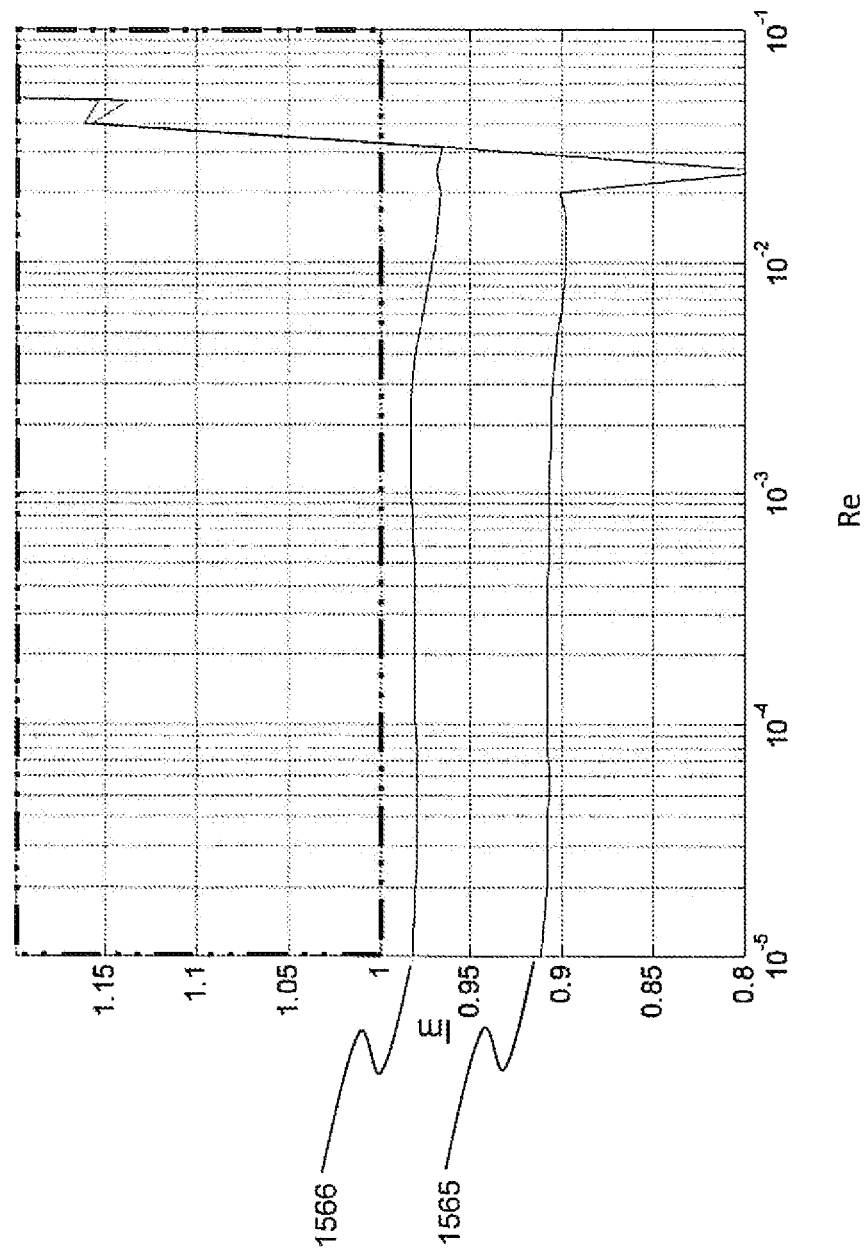

Not considering hypovolemia, the relative uncertainty $\|w(j\omega)\|$ is as shown in line 1565 in FIG. 14H. The PID controller has 3 parameters which need to be tuned. One method of parameter tuning consists in plotting the open loop transfer function in the frequency domain and setting the PID gain and time constant to provide a good enough gain (at least 6 dB) and phase margin (at least 45 deg) to properly control the nominal model defined above. Once the parameters are tuned, the RS condition of Eq. (13) can be verified.

Another more direct method consists in calculating the area between $\|T\|$ and $1/\|w(j\omega)\|$ and the product $\|T\| \cdot \|w(j\omega)\|$, and finding the parameter set $\{K, \tau_i, \tau_d\}$ that (1) minimizes the area and (2) that results in a product that is less than 0.99 for all frequencies. Using this method, it was found:

$$\begin{cases} K = 0.0076 \\ \tau_i = 118 \text{(optimized)} \\ \tau_d = 20 \end{cases} \quad (15)$$

A slightly different result was found using the traditional loop shaping method:

$$\begin{cases} K = 0.0075 \\ \tau_i = 100 \text{ (loop shaping)} \\ \tau_d = 5 \end{cases} \quad (16)$$

Due to the stronger derivative action, the optimized coefficient set may emphasize more the measurement noise on the $WAV_{CNS}$ index. Yet, the derivative action tends to stabilize the overall system.

Figure 14I:
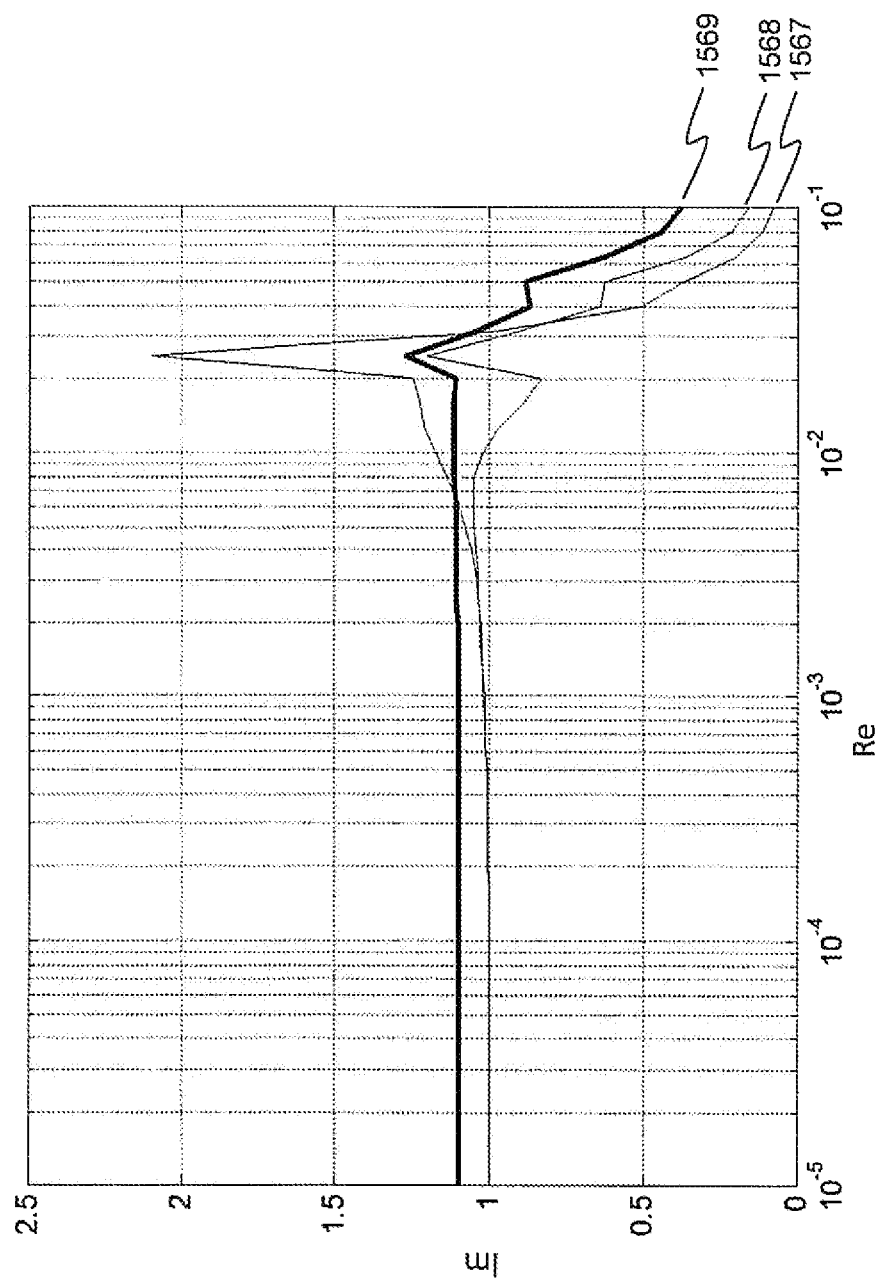

Plotting the norm of the complementary sensitivity function and the inverse of the relative uncertainty, see FIG. 14I, shows that the controller will remain stable for the uncertainty under consideration (line 1568). In contrast, the controller obtained through the loop shaping method violates the RS condition (line 1569). Despite a slightly lower gain, the controller will be unstable in some cases. Using the optimized coefficients, the phase margin is 65 deg, the gain margin is 7.6 dB and the cutoff frequency is 0.016 rad/s based on the nominal model.

Considering the addition of hypo-volemic models, and using the same method described above, the following parameter set was found:

$$\begin{cases} K = 0.0025 \\ \tau_i = 360 \text{ (optimized)} \\ \tau_d = 22 \end{cases} \quad (17)$$

Figure 14J:
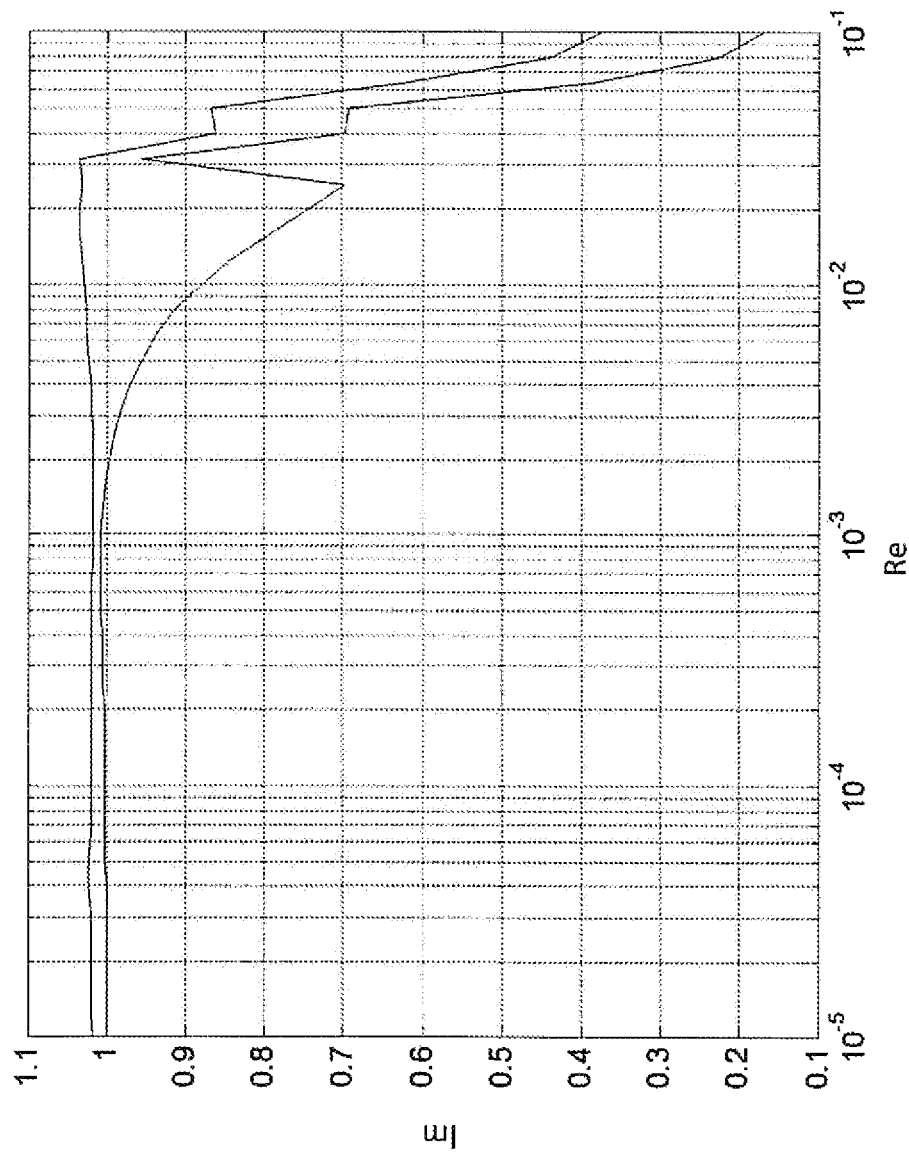

The corresponding phase margin is 75 deg, gain margin is 8.3 dB and cutoff frequency is 0.015 rad/s. While these are very similar open loop characteristics, note that the nominal model is different in this case since it was optimized for the additional hypovolemia models. In fact, both the proportional and integral action is divided by 3, which will slow down significantly the settling time of the system in non-hypovolemic cases, resulting in longer settling time and more settling error during the first 15 minutes of the any change in setpoint of disturbance compensation. The RS condition is verified; see FIG. 14J.

In the above, the PID parameters have been derived to adequately account for large patient variability, spanning the entire adult population, and a control range from light sedation (WAV=70) to deep anesthesia (WAV$_{CNS}$=30). The controller was designed to only administer a Propofol infusion. Due to the faster kinetics, the co-administration of Remifentanil (analgesic drug) should not adversely affect the stability of the close-loop system as long as Remifentanil control actions are located in the high frequencies (e.g., short boluses).

The second "hypovolemic" controller is universal, and will provide stable results even in case of severe hypovolemia, which is particularly important in trauma patients. However, the limited proportional and integral actions will limit the performance of the system in normo-volemic patients, which represent by far the largest target population.

In another embodiment, instead of using a sluggish universal controller, two controllers can be used depending on the patient ASA status. ASA I and II will benefit from the rapidity of the first controller, while patient ASA III and above will automatically be controlled through the second more conservative controller. The user should have the ability to override this decision (most ASA III patients will not be hypovolemic, and may be perfectly well controlled using the first controller).

Representative Examples

Figure 14K:
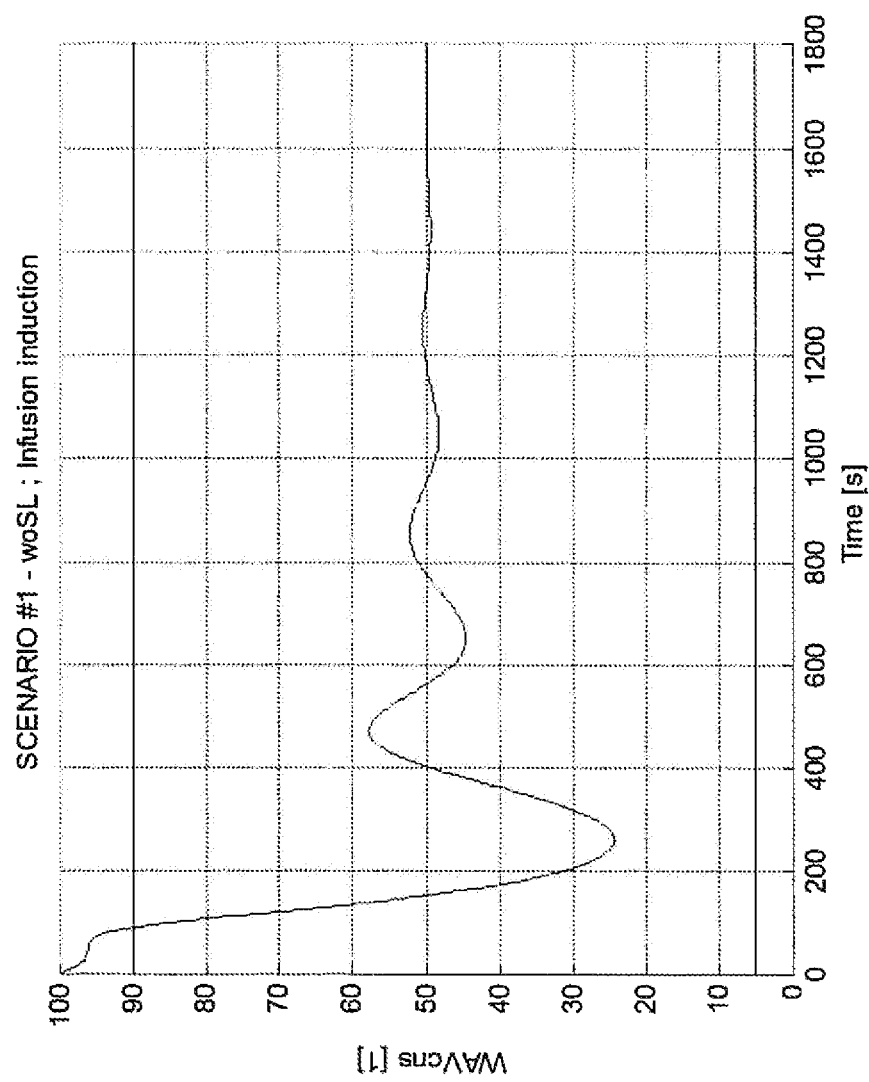
Figure 14L:
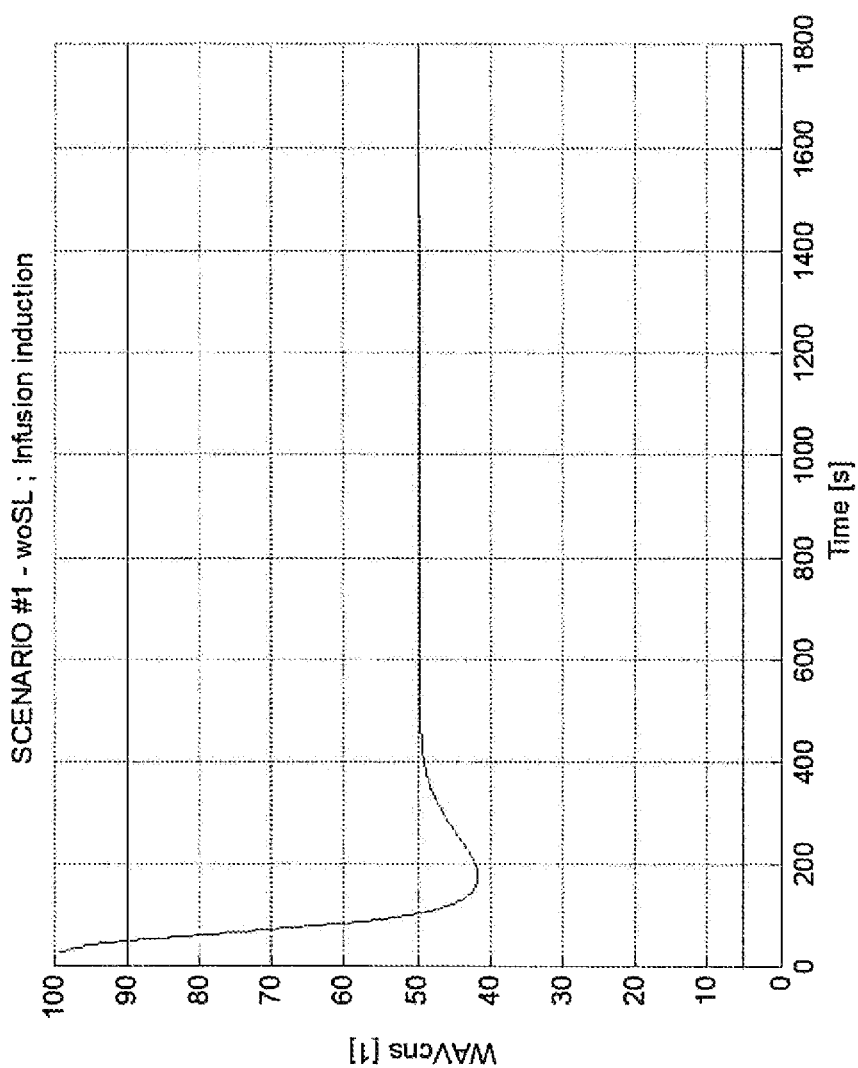

As way of example, to verify the adequacy of the two controllers designed above, an induction was simulated to a target depth of 50 using the patient model exhibiting the strongest oscillatory behavior (model #10), with an additional increase in drug sensitivity of 20%. This corresponds to a worst case scenario in terms of stability margin. The result is as shown in FIG. 14K. The controller remains stable, even thought it exhibits some decaying oscillation. The undershoot is quite large (25 units) but does not result in cortical suppression. In most cases (e.g., model #8), a better behaved result is obtained; see FIG. 14L.

Figure 14M:
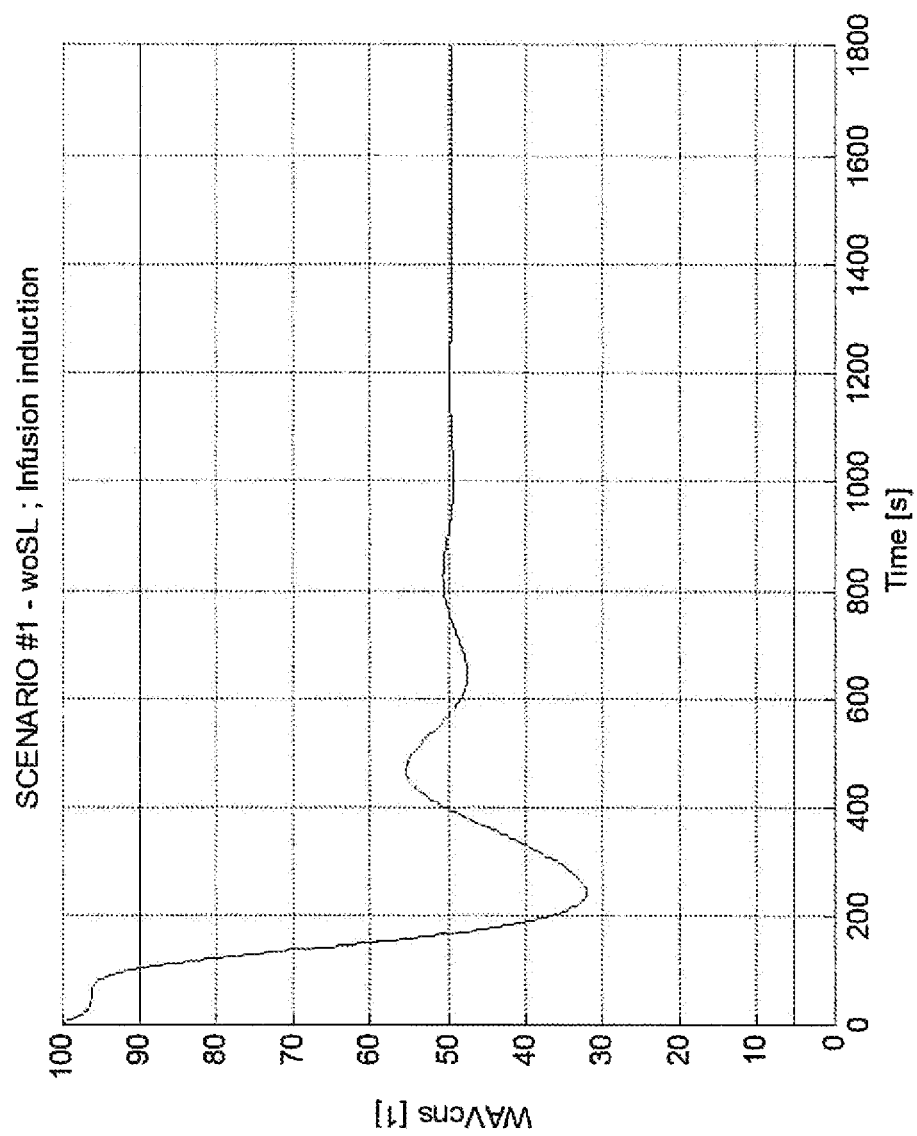
Figure 14N:
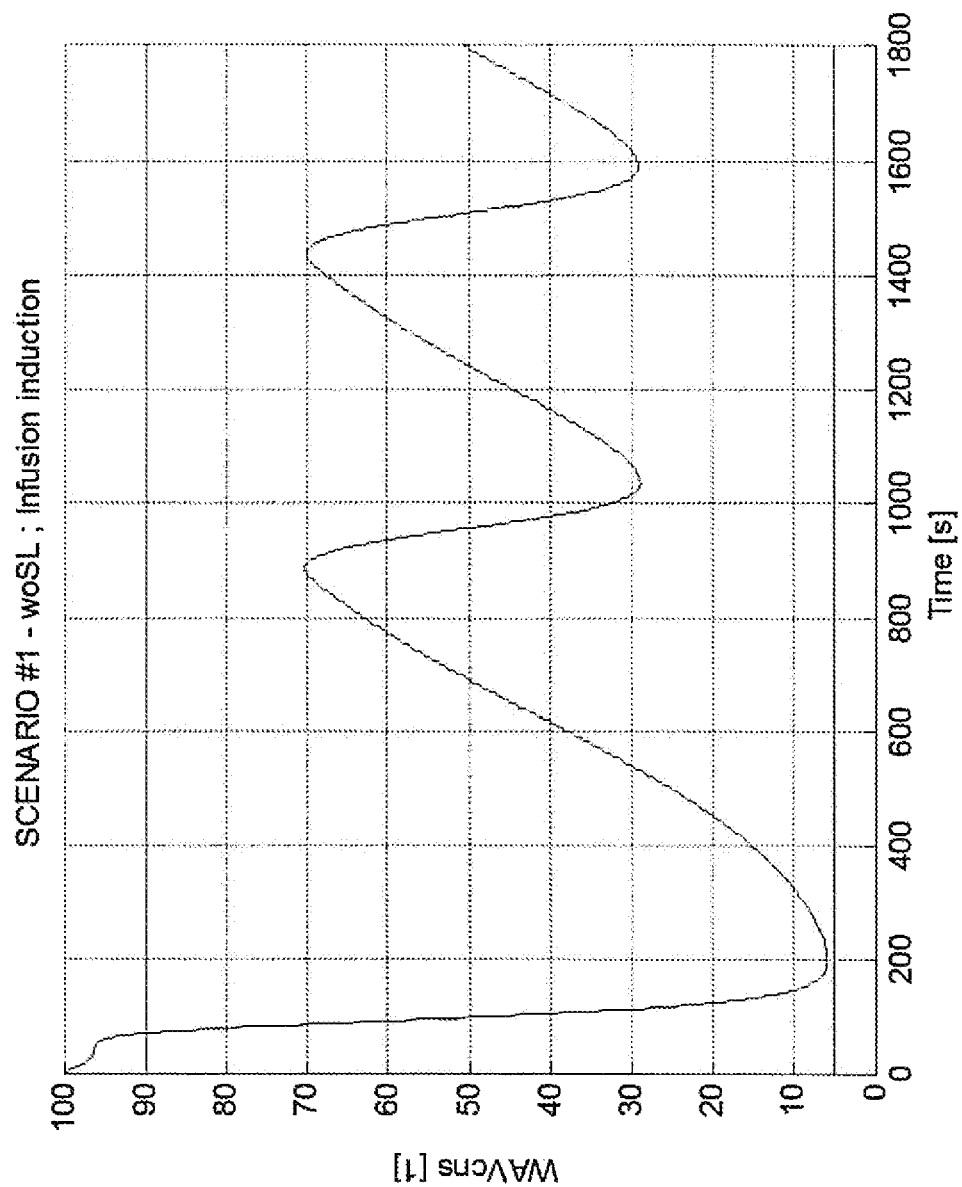
Figure 140:
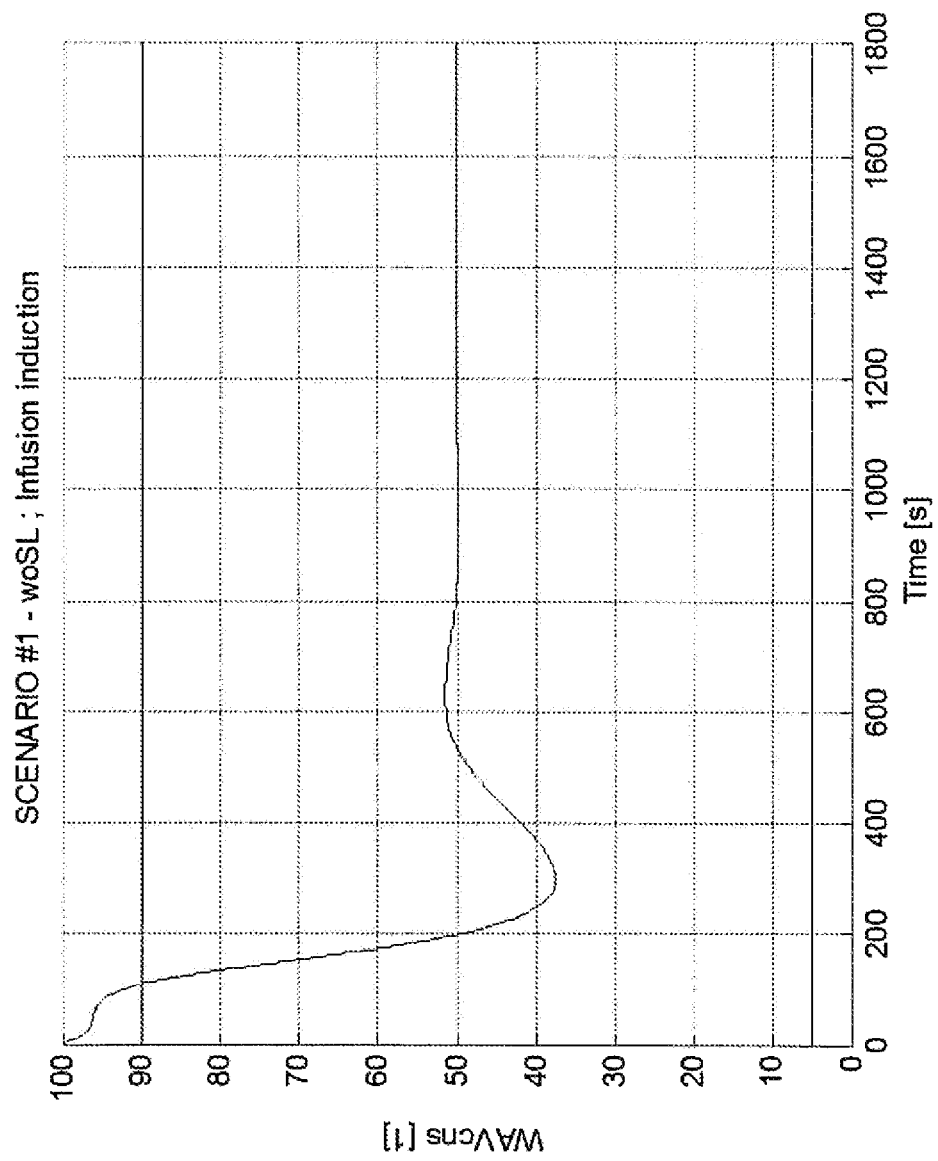

Considering the same patient #10 after a severe hemorrhagic shock, the response in FIG. 14M using the conservative controller is found. Using the more conservative controller ensures stability in hypovolemic cases. The nominal controller would have resulted in strong oscillatory behavior, and deep enough overshoot to result in cortical suppression; see FIG. 14N.

Since this example focused on the worst case scenario in the model list, it is reasonably assured that the two controllers will remain stable and well behaved for all patients considered. These controllers represent a very good starting point. Yet, the decaying oscillations observed in the FIG. 14K prompts consideration of stability enhancing methods, such as a predictive structure that can minimize the effect of the system time delay.

Predictive Control

Most of the instability of the close loop system is related to the large time delay corresponding to the arm-to-brain travel time of the drug. In some models, like model #10, this time delay can be large. Hence, any control action taken by the controller will only be reflected much later. This puts a limitation on the controller cutoff frequency. One idea often used in process control is to add a Smith Predictor. The Smith Predictor (SP) makes use of the nominal model of the system in order to compensate for the delay. The zero-delay nominal model is simulated based on the same infusion rate that is input to the system. As such, the model output represents the predicted delay-free response of the system. This response is then compared to the response with delay. The result of this comparison is a signal that represents the future system response to the control action. This signal is then added to the feedback signal:

$$e = Tgt - WAV_{cns} - (g_o^0 - g_o^{Td}) \quad (18)$$

Where e is the controller input, Tgt is the desired target depth, $g_o^0$ is the delay free nominal model, and $g_o^{Td}$ is the nominal model with the arm-to-brain travel time $T_d$. In steady state, the SP structure is equal to 0. In fact, the SP structure gives a prediction of the effect of the controller on the plant that cannot be sensed by the feedback sensor due to the delay. As a result, the controller can be designed based on a delay-free model, which results in added stability in the control loop that can be further used to increase the controller bandwidth. While the inherent limitation of a delayed system is still present, the increased control bandwidth usually results in increased performances.

Usually, the use of a Smith Predictor (SP) allows the controller engineer to design a controller while considering that the process is delay-free. This works when the system uncertainty is minimum. In the present invention, however, the SP is preferably used to increase the phase margin of the open loop system, and thus make it less oscillatory.

Figure 14P:
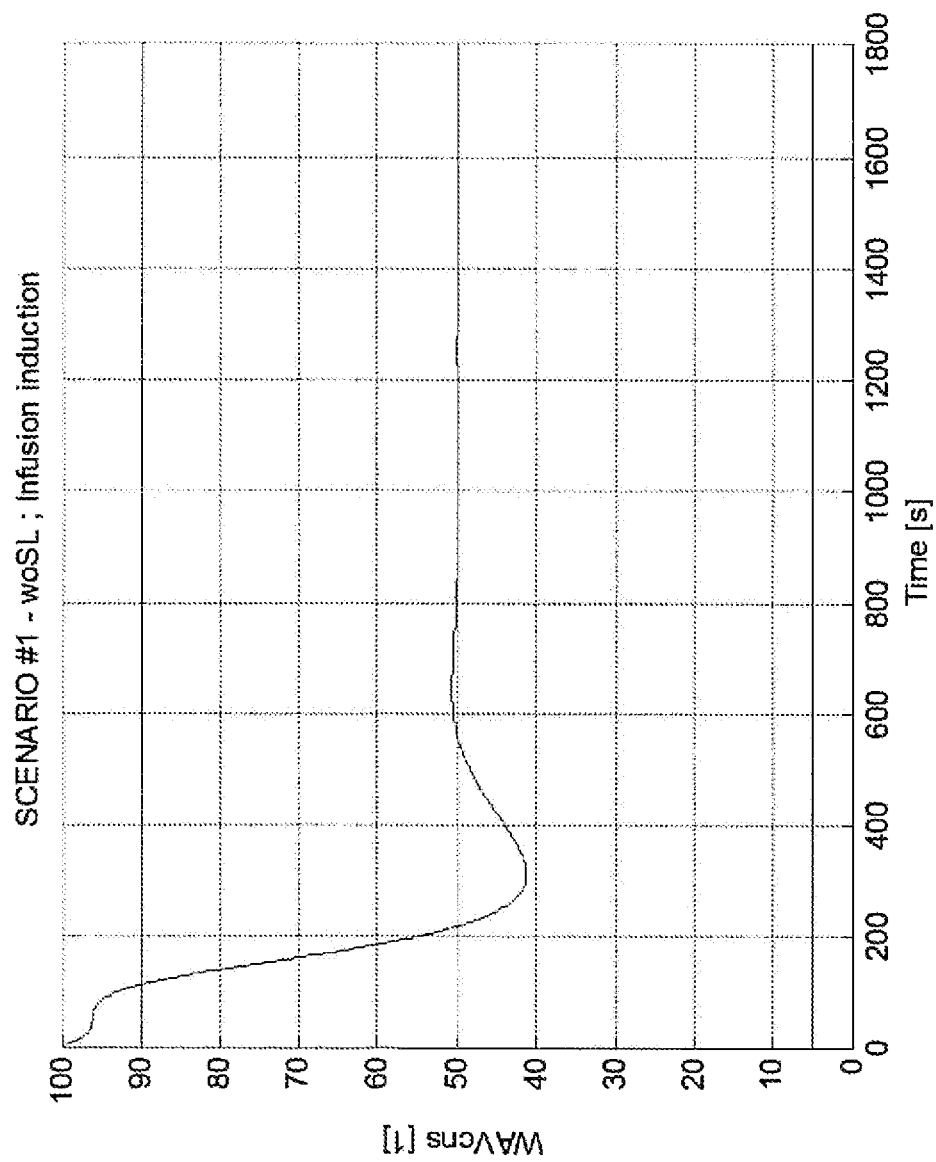

In the proposed embodiment, the internal model used by the Smith Predictor is the LTI part of the PKPD model of an ideal 30 yrs old, 80 kg adult. Using the Smith Predictor, the model #10 patient with high sensitivity exhibits a much better response to an induction to a depth of 50; see FIG. 14O. A similar result is obtained in the hypovolemia case; see FIG. 14P.

The SP will also provide compensation in cases where the infusion pump is stopped temporarily, e.g., to change the syringe. Without the predictive component of the SP, the PID controller may not immediately compensate for the lack of drug injected to the patient during the syringe change. The SP, however, will show a predicted change in the patient state, which will force the PID controller to take action and increase the infusion rate to catch up.

Accounting for patient variability allows various embodiments of the present invention to reasonably assure the users that the controller design will yield stable results, and will not result in a patient be driven in and out of cortical suppression by control actions that may be too aggressive. While the robust design method is not a validation of the controller per se, it allows regulatory bodies to gain the confidence necessary to approve its use.

The addition of a Smith Predictor further allows various embodiments of the present invention to further stabilize the controller, resulting in smoother operations. The predictor will also helps compensate for temporary actuator stalls, like during a syringe refill. Other predictive control structure can be used, e.g., like Model-Based Predictive controllers and the like.

Real-Time Adaptive Control Methods

In those embodiment described above, the design is for a single fixed robust predictive PID controller that remains stable and well behaved for all patients, including those in hemorrhagic chock (i.e., with severe blood loss) and who are more sensitive to Propofol. While this controller remains safe from a stability point of view, it is very conservative and may not provide the most preferable performance for the largest population of patients (non-trauma, normo-volemic, elective patients). A change in targeted depth, or a compensation for a sudden increase in cortical activity, may not be provided fast enough. As a result, a more aggressive control design is also proposed, which preferably is more desirable for healthier segments of the patient population.

While the user can choose which controller including combinations thereof to use at any time during the operation of the system, it may be more useful, user-friendly, and safer to have the system automatically switching between the two controllers based on the patient's reaction to the drug administration. Hence, hypo-volemic patients may be switched to a faster controller when fluids are administered to bring them back to a normo-volemic state. Similarly, patients suffering from a major blood loss during surgery may be switched from the nominal fast controller to the conservative slow controller. In addition, the switching between one controller to the next can be done progressively, e.g., by increasing the overall gain if the patient sensitivity to the drug decreases, or vice versa by decreasing progressively the controller gain if the patient becomes increasingly sensitive to the drug. This online adaptation can be achieved using an adaptive control technique, such as the one described below.

In the example given above, this embodiment derives two controllers:

$$\begin{cases} K = 0.0025 \\ \tau_i = 360 \text{ (optimized)} \\ \tau_d = 22 \end{cases} \quad \text{(CNTR. 1)}$$

$$\begin{cases} K = 0.0076 \\ \tau_i = 118 \text{ (optimized)} \\ \tau_d = 20 \end{cases} \quad \text{(CNTR. 2)}$$

(CNTR.1) provides both stability and good performance in hypovolemic patients, but is less desirable when used with patients having a normal physiology.

(CNTR.2) provides stability and a good level of performance in healthy patients, but becomes unstable in some hypovolemic patient models.

Figure 15A:
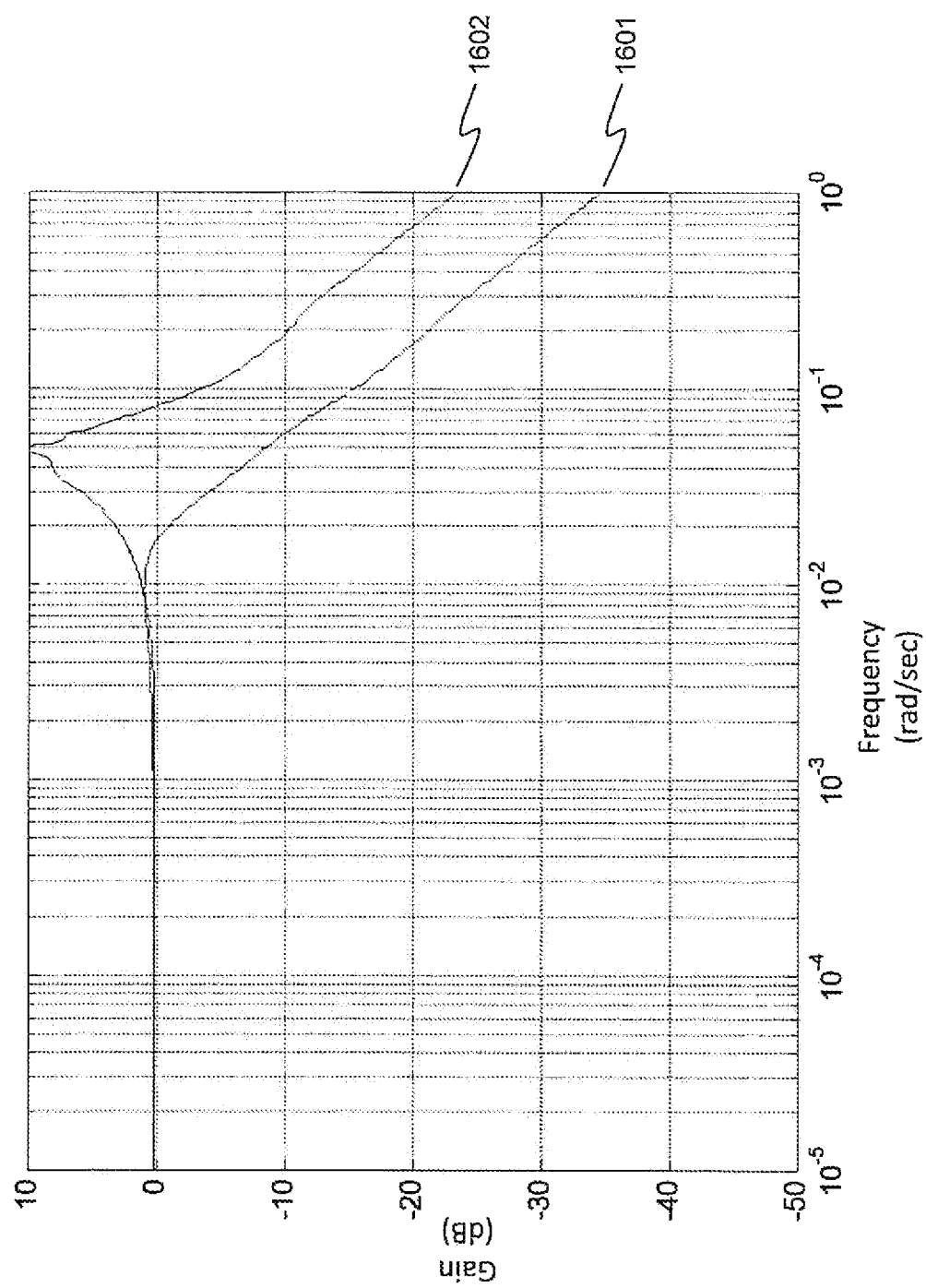
FIGS. 15A-G. Various graphs depicting results of using different controllers for providing anesthetic or sedative drugs including: A) average closed-loop transfer function of normo-volemic patients (blue line) and hyper-volemic patients (red line) when using the nominal controller (CNTR.2); B) average closed-loop transfer function of normo-volemic patients (blue line) and hyper-volemic patients (red line) when using the conservative controller (CNTR.1); C) patient model #16 with the nominal controller (CNTR.2); D) patient model #16 with the conservative controller (CNTR.1); E) patient model #29 with the conservative controller (CNTR.1); F) patient model #16 with the adaptive controller; G) patient model #29 with adaptive controller.
Figure 15B:
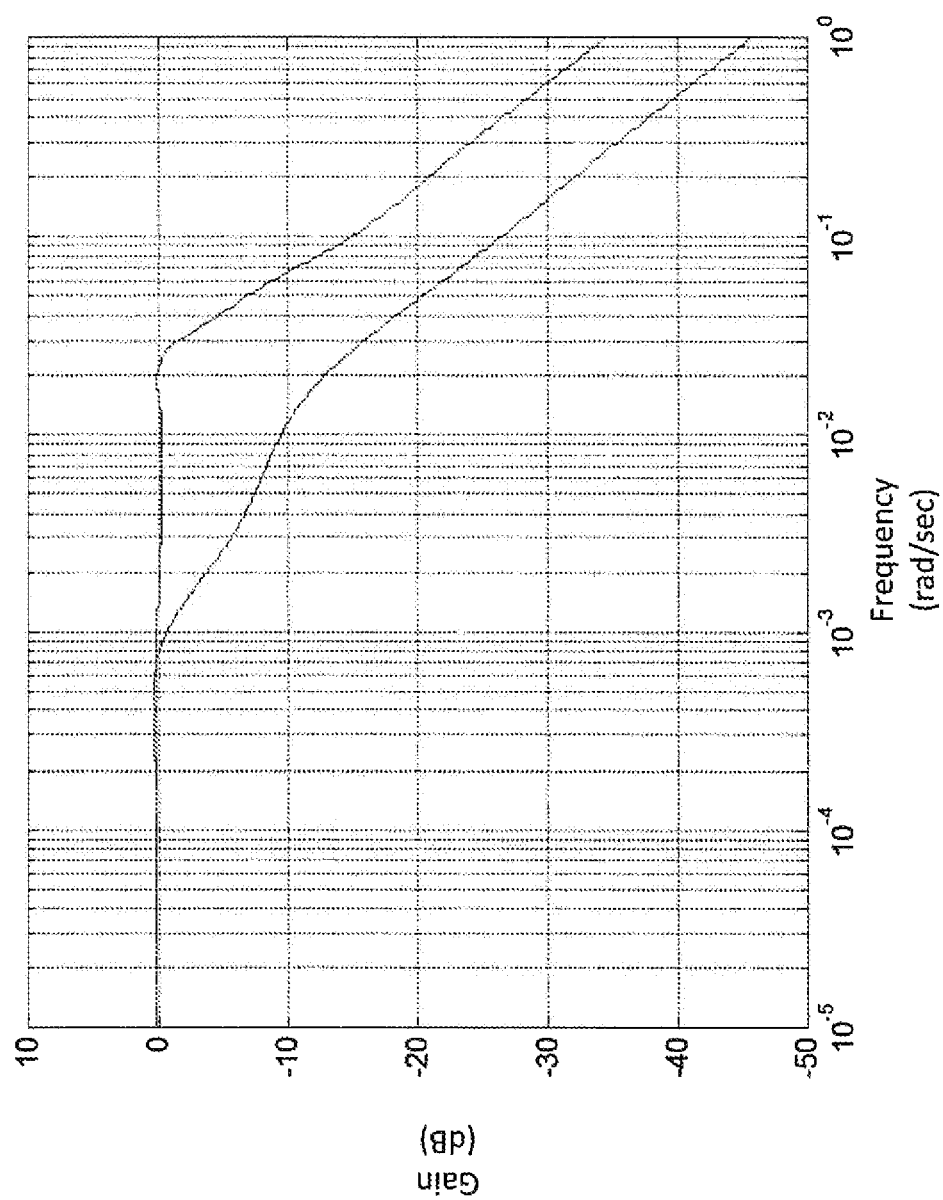

In order to automatically adapt the control algorithm parameter to the patient, continuous on-line identification of the patient drug-sensitivity is required. Looking at the closed-loop transfer function shows that using the high performance nominal (CNTR.2) controller gives a good closed-loop characteristic in normo-volemic patients (line 1601), but results in a large increase in frequencies around 0.05 rad/sec in hypo-volemic patients (line 1602); see FIG. 15A. Conversely, using the conservative controller, hypo-volemic patients are well controlled by the close-loop controller, but normo-volemic patients exhibit a loss of close-loop gain in frequencies ranging from 0.001 to 0.01 rad/sec; see FIG. 15B. This loss of close-loop gain results in low performance (resulting in taking a longer while to reach the target, and where the system does not correct quickly for disturbances).

Since one of the goals of the closed-loop sedation/anesthesia system of certain embodiments of the present invention is to keep the patient within a given range of cortical activity level, it is acceptable to generate small fluctuations in the output WAV$_{CNS}$ index, as long as these fluctuations do not push the cortical activity level outside the targeted range. In one embodiment, the adaptive control strategy relies on adding a small sine-wave identification signal on top of the target signal, in the frequency range that typically generate the closed-loop gain increase in hypovolemic patients (e.g., at 0.05 ra/sec, or 120 seconds period).

The identification signal is fairly slow (120-sec period). To measure its amplitude, at least one full cycle needs to be acquired, which represents a minimum of 120 seconds. Part of the 120-sec signal component amplitude comes from the measurement noise. This measurement noise is for the most part a white noise. It is expected that the measurement noise will be different between patients, and at different WAV$_{CNS}$ depth. It is unlikely that a theoretical value can be calculated and be applicable to all cases and at all times. A better method consists in measuring the background measurement noise close to the 120-sec frequency range and subtracting that measure from the measure at 120-sec. Different signal processing methods can be used. The one giving good results is based on redundant wavelet decomposition, denoising, and their inverse transform. Digital filters can also be used.

If the WAV$_{CNS}$ exhibits similar oscillations as the identification signal, the patient can be considered sensitive to the drug, and the controller gain can be reduced to account for this sensitivity. Conversely, if the output oscillations are negligible, controller gain and integral time constant can be increased.

By way of example, various embodiments of the present invention can be better understood by considering the following example: a patient is undergoing surgery during which the closed-loop system is used to maintain a cortical activity level of 60 at all times. The patient is normo-volemic, but at t=2 hours, the patient becomes suddenly severely hypovolemic due to undetected internal bleeding. At t=40 minutes, a strong stimulation increases the cortical activity level. This stimulation stops at t=1 hour. The same stimulation occurs at t=12000 seconds (3 hours and 20 minutes).

Figure 15C:
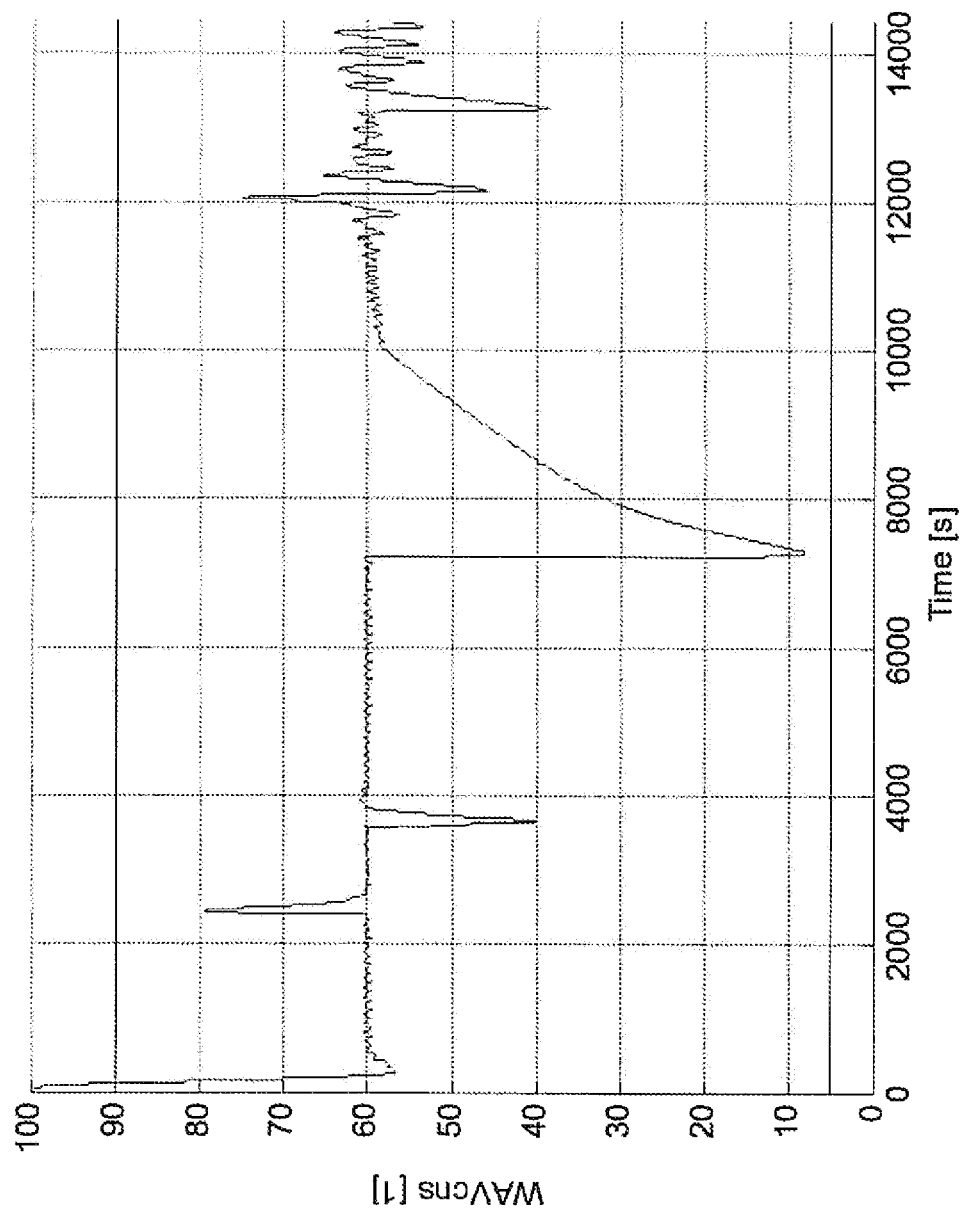

Using the high performance controller (CNTR.2), the WAV$_{CNS}$ index is as shown in FIG. 15C. It can be seen that the close loop controller was able to induce the patient rapidly, and reject the disturbance accordingly. However, after the patient became hypovolemic (i.e., much increased drug-sensitivity, hence the large WAV$_{CNS}$ drop), the output shows marked oscillations with increasing amplitude, a sign of instability.

Figure 15D:
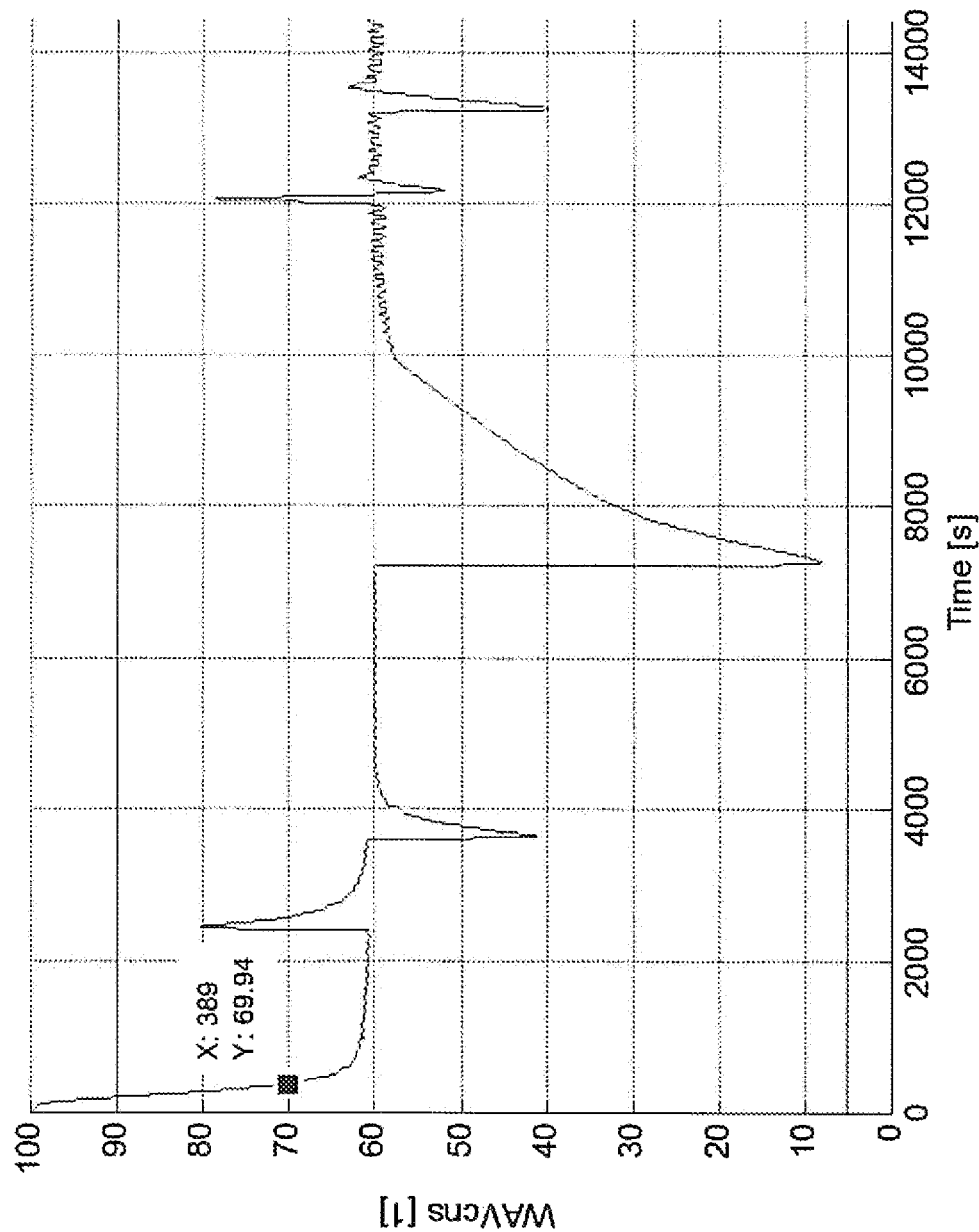
Figure 15E:
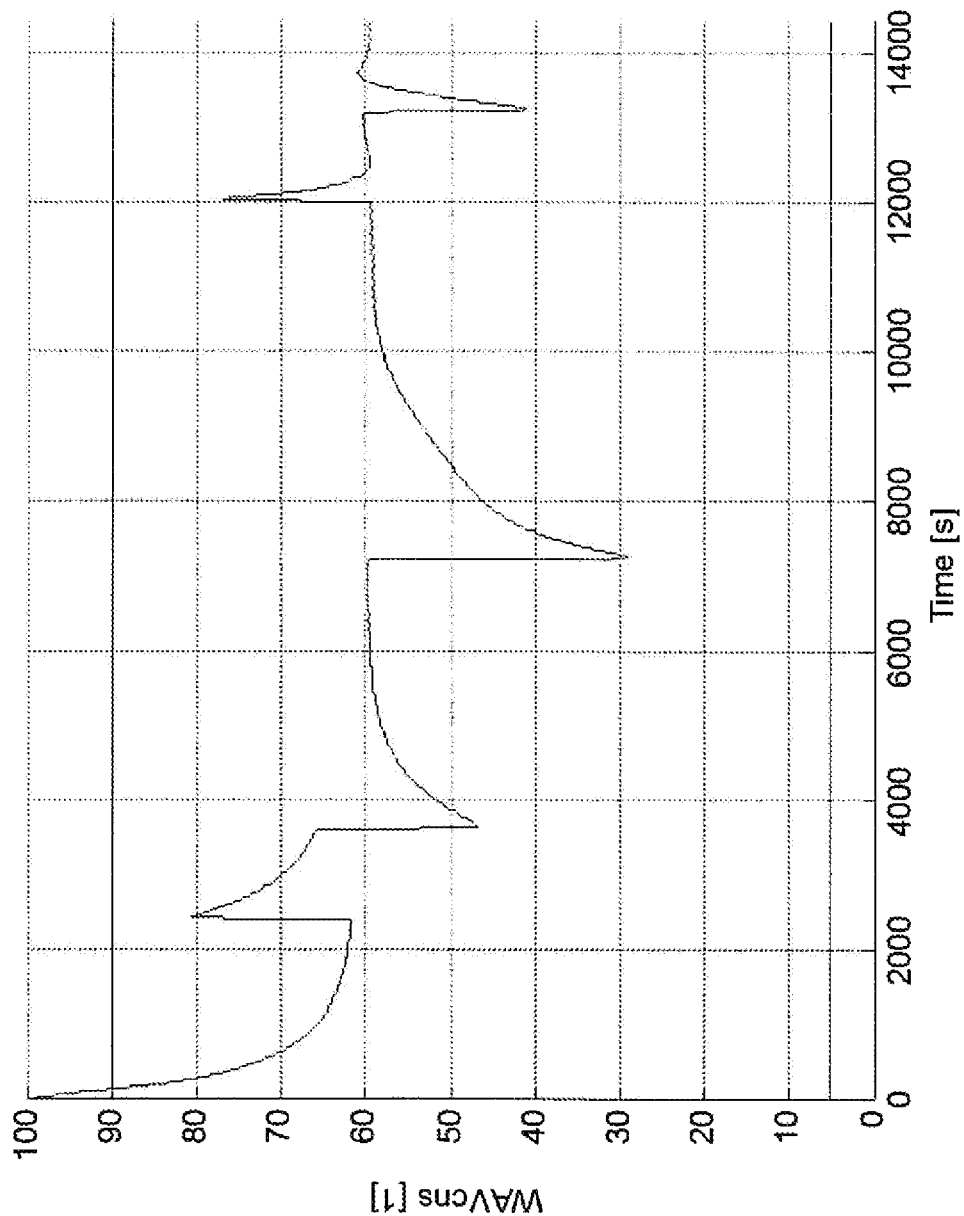

If, on the contrary, a more conservative controller is used, the oscillations would be well dampened. However, it would take twice as long to induce the patient and reject the first disturbance during the normo-volemic state; see FIG. 15D. The induction is 6.5 minutes, and the disturbance rejection 3 min. While this result may be clinically acceptable for this patient, the conservative controller leads to particularly bad results for other patient models, like the one depicted in FIG. 15E. For patient model #29, the induction and the rejection of the initial disturbance take more than 10 minutes to achieve.

Figure 15F:
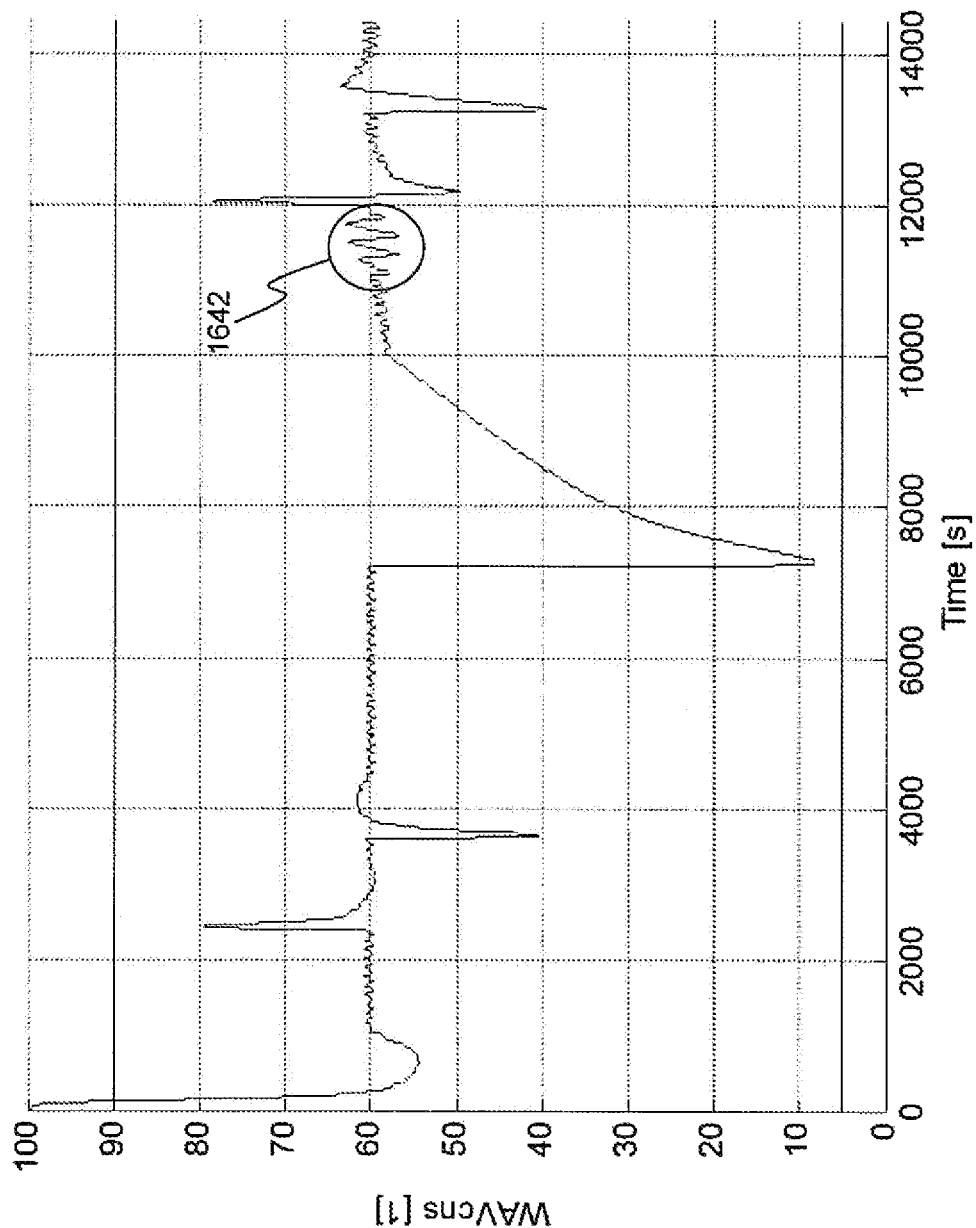
Figure 15G:
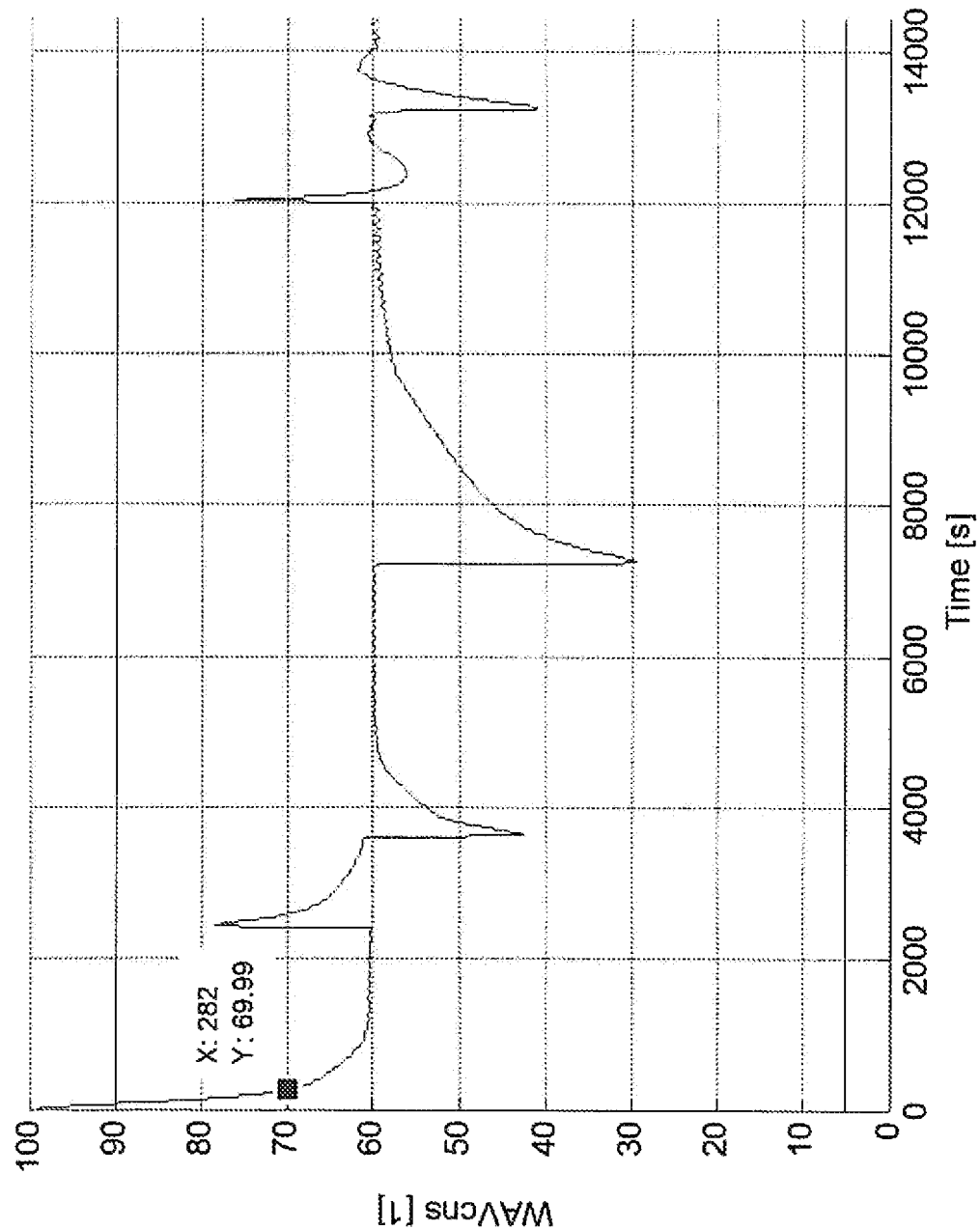

Using the adaptive control scheme, the controller parameters are automatically adjusted based on the perceived close-loop sensitivity of the patient. For patient #16, the induction was achieved in 3 min and 20 sec, and the rejection of the disturbance was achieved in less than 2 minutes; see FIG. 15F. The small oscillations observed on the $WAV_{CNS}$ output are the 120-sec identification signal. At one point, the identification oscillations started to get larger, as the adaptive algorithm tried a more aggressive control parameter set (circled in the graph at 1642). However, the controller quickly recognizes the heightened drug sensitivity of the patient, and reduces the controller gain and integral time constant afterwards. The induction for patient #29 using the adaptive controller is achieved in less than 5 minutes, while the initial disturbance rejection is achieved in just over 3 minutes; see FIG. 15G.

These examples show how the adaptive control scheme helps ensure that the controller remains stable, with adequate performance, even in patients whose drug sensitivity cannot be initially assessed by the anesthesiologist, or in patients whose drug sensitivity changes during the course of the surgery. It should be noted that because the identification signal is relatively slow, it does take some time to zero-in on the right control parameters. In addition, the extraction of the output identification signal in a noisy $WAV_{CNS}$ signal is difficult, and requires sophisticated signal processing techniques (wavelet-based denoising).

It should be noted that, in the above embodiment, the controller adaptation is done automatically. The adaptation can also be done manually, by warning the user when the controller used by the system is no longer effective or safe for the patient. In this embodiment, the user would manually switch from one controller to the next, or modify the control parameters manually.

Alternatively, other adaptive control techniques may be used, where the controller characteristics are automatically modified based on the identification of the subject's dynamic response to drug administration. The adaptation can be as simple as a gain scheduling, which utilizes a series of individual linear controllers to measure and control individual measurable variables. Instead of gain scheduling, the adaptation can be based on continuous identification of the subject's behavior, or can simply be based on induction data, i.e., measurements of how the subject responds to the initial drug boluses. In particular, the identification of the time delay between the injection of the drug and the onset of effect may significantly help in optimizing the controller algorithm. For instance, predictive control techniques can be employed to limit the effect of this delay, like the Smith Predictor structure discussed above.

Other Design Considerations

While a variety of control structure and algorithms can be contemplated, the control algorithm can further be supplemented with algorithmic means to detect instability. For instance, if the measured feedback quantity starts to oscillate in opposition of phase with the infusion rates of the drugs, this can be a sign of instability, and as such the controller algorithm needs to be set on a more conservative mode. Typically this would involve a reduction of the controller's gain. This instability detector can also be used to optimize the control performance. In some embodiments, the controller gain may be increased until signs of instability are detected. This would result in much faster control action in subjects responding slowly to drug administration.

The control module preferably also integrates the means to continue to operate when sudden loss of feedback measure occurs. For instance, if the electrodes become loose, or if a period of heavy artifact activity occurs, it is possible that the feedback measure may be lost and that the controller needs to operate in open loop. Likewise, if the two bilateral measures strongly differ, and the system is unable to choose between either measure, the controller cannot reliably use the feedback measure provided by the brain monitor. If this were to occur, a number of solutions may be implemented. First, the controller may just hold the last infusion rate values. Preferably, the controller may set the pumps to a default rate of infusion, as specified by the caregiver or preprogrammed into the system. Also preferably, the controller may use past data to derive a near-future infusion profile and implement this profile automatically. Another method involves calculating the infusion profile to maintain a certain targeted estimated effect-site or plasma concentration based on pharmacokinetics/pharmacodynamics models of the subject. The targeted concentration may be defined by the caregiver, preprogrammed into the system, or preferably automatically derived based on past data. In all cases, the loss of the feedback measure is preferably accompanied by an audible and visual alert to the caregiver.

In one embodiment, a novel controller-related mechanism can be implemented to handle sparse feedback, i.e., situations where the feedback variable may disappear from time to time. For instance, a review of 139 clinical cases obtained over a course of 12 months shows that the $WAV_{CNS}$ index may become unavailable due to the presence of artifacts. On average, about 2% of the EEG signal during a case contains artifacts that cannot be removed (e.g., electro-surgical artifacts). While 2% is excellent when considering the very low signal-to-noise ratio of EEG signals, the artifact periods tend to be grouped together, and not distributed over the entirety of the case. This creates gaps in $WAV_{CNS}$ data during the surgical intervention. It has been shown that:

50% of the gaps were less than 7 seconds
80% of the gaps were less than 15 seconds
~99% of the gaps were less than 60 seconds
About 10% of the cases had at least one gap longer than 60 seconds The "traditional" way to handle the fallback situation when the feedback variable becomes unavailable is to revert to an open-loop Target Controlled Infusion (TCI) mode, where the system operates in open-loop mode and targets a desired plasma or effect-site concentration using a population-based model (instead of the actual measured effect). While this method is possible in many different countries, this fallback plan is not an option in the U.S. since open-loop TCI is not an FDA-cleared technology. A different method needs to be implemented.

By way of non-limiting example, 5 separate robust predictive PID controllers designed to operate at different refresh rates can be envisioned:

The first controller is the one described herein (e.g., CNTR.1 or CNTR.2), and is designed to operate on a per-second base. Each time a new $WAV_{CNS}$ index is available, the controller is updated, and its control action is implemented. This controller is robust and incorporates a predictive element in the form of a Smith Predictor to provide a better stability profile while not degrading its performance.

The second controller operates at a refresh rate of, for example, 7 seconds. It uses the exact same structure as the first controller (PID with Smith Predictor) and is designed the exact same way to guarantee its stability (robust design). Because of the lower refresh rate, this controller gain is slightly slower as compared to the first controller, resulting in slightly degraded performance. The advantage is that this controller does not "care" about what happens to the patient in-between its refresh samples. In other words, the $WAV_{CNS}$ may become unavailable between samples 2 and 6 without affecting its operation, and performance.

The third controller has the exact same structure and is designed the exact same way, but with a refresh rate of, for example, 15 seconds.

The fourth controller has the exact same structure and is designed the exact same way, but with a refresh rate of, for example, 30 seconds.

The fifth controller has the exact same structure and is designed the exact same way, but with a refresh rate of, for example, 60 seconds.

Every second, the output of all these controllers is calculated, and a control action time course spanning the next 60 seconds is derived. The first control action is implemented. If at the next second a valid $WAV_{CNS}$ index is calculated, the 5 controllers are refreshed and a new 60-sec control action time course is calculated. On the contrary, if the $WAV_{CNS}$ index is unavailable, the controllers are not updated, and the system simply continues implementing the last valid control action time course.

This scheme takes care of 99% of all the feedback variable gaps. Gaps longer than 60 seconds trigger the default infusion rate set by the user at the start of the case (the default rate the user selected in case closed-loop operation must be discontinued).

Figure 16:
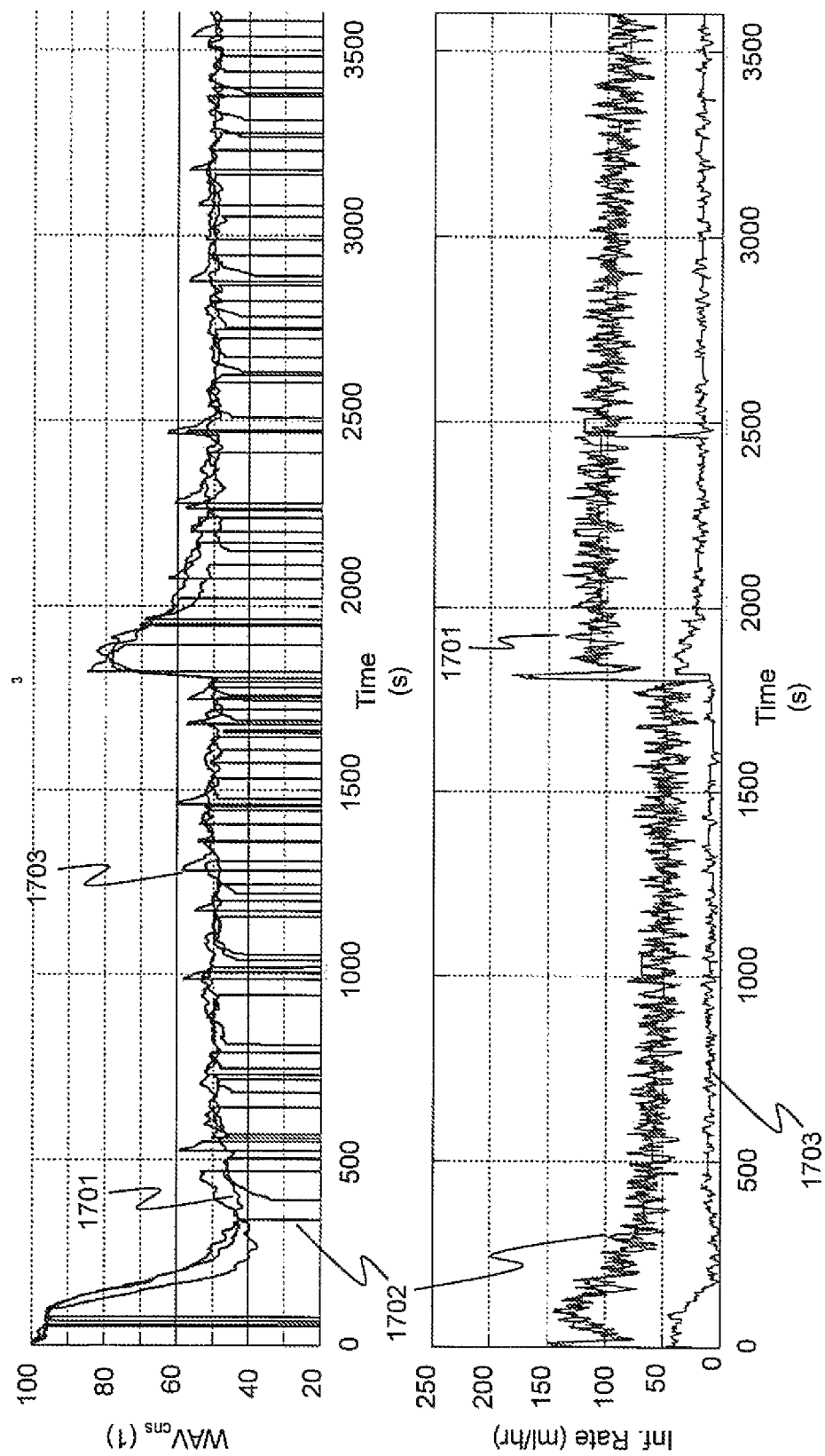
FIG. 16. Robust Predictive and Sparse controller: during gaps in the feedback variable, different robust predictive PID controllers with longer refreshing rates are used. In this example, WAVCNS data gaps are represented with vertical lines.

The results of this method are actually very impressive. Data gaps of less than 60 seconds do not affect the performance of the closed-loop operation in any significant way. The following is an example of a simulated case where a target of 50 was set, and the system was set to induce the patient. At t=1800 seconds, a large+30 unit disturbance is simulated, corresponding to a surgical stimulation. The results of this example are depicted in FIG. 16. Line 1701 corresponds to the ideal situation where there is no data gap. Line 1702 simulates the effect of data gaps of random duration and randomly distributed in the case. As can be seen in this example, the sparse robust predictive PID controller succeeds in maintaining a high level of performance despite the feedback signal loss. FIG. 16 also shows the simulated result for the same patient while in severe hypovolemic shock (line 1703—note how the overall Propofol infusion rate is much lower).

(Note: the data gaps being random, the simulation line 1702 and the simulation line 1703 do not have the gaps at the same location.)

Other Safety Aspects

An important safety aspect is also to limit the control action of the controller. For instance, the caregiver can define upper and lower infusion rates that the controller cannot exceed without the caregiver's acknowledgement. Preferably, the caregiver could define upper and lower effect-site or plasma concentrations beyond which the controller should not operate. In this case, the controller would not be able to derive an infusion profile which would lead to a violation of these upper and lower concentration bounds. The effect-site or plasma concentration may be either estimated using pharmacokinetic and/or pharmacodynamic models, or directly measured through blood analysis or other biomarkers. Alternatively, these limits may be predetermined and preprogrammed into the system.

In a preferred embodiment, the safety limits are directly calculated based on the drug manufacturer's recommendation. These recommendations are typically based on the patient's weight, age, height, gender and overall health status. By entering this information in the system, the user will be proposed a de facto minimum and/or maximum infusion rate, or drug dosage that the system will not exceed. These pre-calculated safety limits may be overridden by the user at any time.

The control module should preferably take as input the effective infusion rate delivered by the infusion pump(s), and not the rate determined by the controller. The effective rate is either measured by the pump, using appropriate sensors, or is simply the rate at which the pump currently operates. The effective rate may be different than the rate the controller outputs. Preferably, the closed-loop system should not assume the rate it has sent the infusion pump is equal to the effective rate. In case a syringe is empty, or if the caregiver may stop the pump manually, the controller may compensate for the lack of drug injected to the subject by catching up once the pump is operational again. This is typically done through the predictive part of the control algorithm. For safety reasons, any issue with the infusion pump(s), such as an empty syringe, a line occlusion, loss of communication/power, etc., should be systematically delivered to the caregiver. Such delivery can take place via audio signal, visual signal on the display, wireless communication, or the like. Another safety issue is to validate that each pump is delivering the right drug. This can be done by prompting the caregiver to validate the drug and drug concentration prior to starting the case.

Another useful feature of the control module is its ability to detect out-of-the-ordinary subjects, e.g., subjects which may require much higher or much lower drug administration. Such subjects may be suffering from an underlying pathology, for example. The control module could automatically and continuously measure the difference between the amount of drug effectively administered, and the amount of drug that would have been administered in open-loop, i.e., based on a pharmacokinetic and pharmacodynamic model of the subject. If there is a large difference between the two, the subject differs significantly from the norm. This information may be useful to the caregiver, as it may denote an abnormal volemia, or metabolism.

As noted above, many embodiments of the present invention further comprise at least one drug infusion device. The drug infusion devices envisioned for use with these embodiments may be of a typical syringe infusion pump presently known to those of skill in the art. Such infusion pumps will be particularly suited for embodiments wherein the IMIS is integrated into a medical transport or evacuation vehicle, and thus wherein the IMIS may be a larger system that is mounted in a stationary manner within said vehicle. However, many other embodiments will utilize a miniaturized, portable infusion pump(s) in order to provide sedation control and/or pain control in the field until such medical transport can arrive, or the subject can be delivered to a higher echelon of medical care.

In the envisioned syringe infusion pumps, a piston applies pressure on a disposable syringe filled with the drug to be delivered, either a hypnotic (sedative or anesthetic), or analgesic drug. Infusion pumps can allow for very small rates of delivery (i.e., less than 0.1 milliliters per hour) or larger rates of delivery (i.e., more than 1,000 milliliters per hour), which makes them ideal for delivering either rapid boluses or much slower and longer infusions. The infusion pump mechanism itself is preferably very simple and is constructed of a light frame of metal (e.g., aluminum) or plastic, where a cursor moves up and down along a screw whose angular position and rotational speed is controlled through a gear connected to a brushless stepper motor. The cursor is attached to the syringe plunger such that pressure on the plunger can be exerted when the stepper motor rotates. When such pressure is placed on the syringe plunger, it slowly forces the plunger through the syringe, thus dispensing the particular drug out of the needle end of the syringe.

Although syringe pumps are envisioned for most embodiments, in some embodiments other types of pumps may be used. Peristaltic pumps provide the advantage of permitting a very large reservoir, and may be used when it is anticipated that a large quantity of drug may need to be delivered over an extended period of time. Volumetric pumps, gravity-based pumps, or any other type of pump known to those skilled in the art might also be used. Drug delivery may also be performed by providing a vaporized, atomized or gaseous drug which is inhaled by the patient or subject to induce anesthesia or sedation. In such case, the delivery of the drug may be made by means of an oral or oral-nasal mask, a nasal cannula, or other suitable means, and the IMIS would include, as appropriate, a pressurized canister for the gaseous drug, or a vaporizer or atomizer. The closed-loop delivery system would then control a pressure valve or other flow control apparatus, instead of (or in addition to) a syringe pump or similar pump, in order to regulate the delivery of the drug to the patient or subject. In such oral or oral-nasal delivery embodiments, the entire system may be integrated as a face mask that secures to the head with an elastic band or strap, or other suitable attachment methodology or apparatus that simultaneously ensures the appropriate EEG sensor connections on the forehead and/or temples and securely seals the delivery system around the airway entrance(s). Preferably, in such embodiments, the entire system is integrated into the face mask, providing for ease of application and use in a battlefield or other emergency scenario to provide fast and easy administration of closed-loop sedation or anesthesia.

In many embodiments, the particular type or variety of drug delivery pump(s) chosen may be directly influenced by the type of drug being administered. Thus, it may be preferable for the system to be modular in nature such that several types of drug infusion pumps may be used simply by attaching the different pump to a base unit. Also preferably, the system is designed to work with and administer a large variety of types of drugs to a subject. One particular class of drugs the systems, devices and methods of the present invention are designed to administer includes vapour or inhaled sedatives and anesthetics, which includes drugs such as, for example, sevoflurane, isoflurene, desflurane, and other like drugs. Another class of drugs the systems, devices and methods of the present invention are designed to administer includes intravenous sedatives and anesthetics, which includes drugs such as, for example, barbiturates, benzodiazepines, phencyclidine, carboxylated imidazole, isopropylphenol, dexmedetomidine, and other like drugs. Still another class of drugs the systems, devices and methods of the present invention are designed to administer includes opioids, which includes drugs such as, for example, morphine, fentanyl, alfentanil, sufentanil, remifentanil, and other like drugs.

The main difficulty in using infusion pumps in a field-deployable closed-loop sedation system lies in the management of potential failures. In practice, infusion pumps for human use must be certified to have no single point of failure. That is, no single cause of failure should cause the pump to silently fail to operate correctly. The infusion pump should at least stop pumping and make at least an audible error indication. This is a minimum requirement on all human-rated infusion pumps. At a minimum, the angular velocity of the motor drive and the cursor position must be measured in real-time to verify that they both correspond to the expected infusion rate set by the IMIS. Any difference between the two measures automatically shuts down the power to the drive and outputs a visual and/or audible alarm.

The infusion pump(s) of the present invention further comprise additional sensors and features that are required for use of such infusion pumps on humans: (1) an anti-free-flow device to prevent blood from draining from the human subject, or prevent the drug from freely entering the human subject, when the infusion pump is being set up; (2) a pressure sensor to detect occlusion (e.g., vein blockage, or kink in the line); and (3) a syringe lock mechanism to verify that the syringe is properly placed and to check its outer diameter. In addition, the IMIS system may also be capable of battery operation so that drugs can be infused to patients during power failure. The IMIS will also keep a detailed log of the pump operation, including start and end time of infusion, infusion rates, total volume administered, etc. This detailed log will be stored along with other data, as described above, on the internal removable or non-removable memory. Alternatively, or in conjunction with the internal memory of the system, the IMIS will be capable of maintaining a very large database using a large capacity solid-state drive.

It should be noted that, while the IMIS depicted in FIGS. 10A-J integrates the infusion mechanism for ease-of-use and limit size and weight, other embodiments exist where the IMIS controls external infusion systems via, for example, a parallel or serial bus interface (e.g., USB, RS232, or the like), a network interface (TCP/IP protocol), or via a wireless interface (e.g., WiFi, Bluetooth, or the like).

Figure 11:
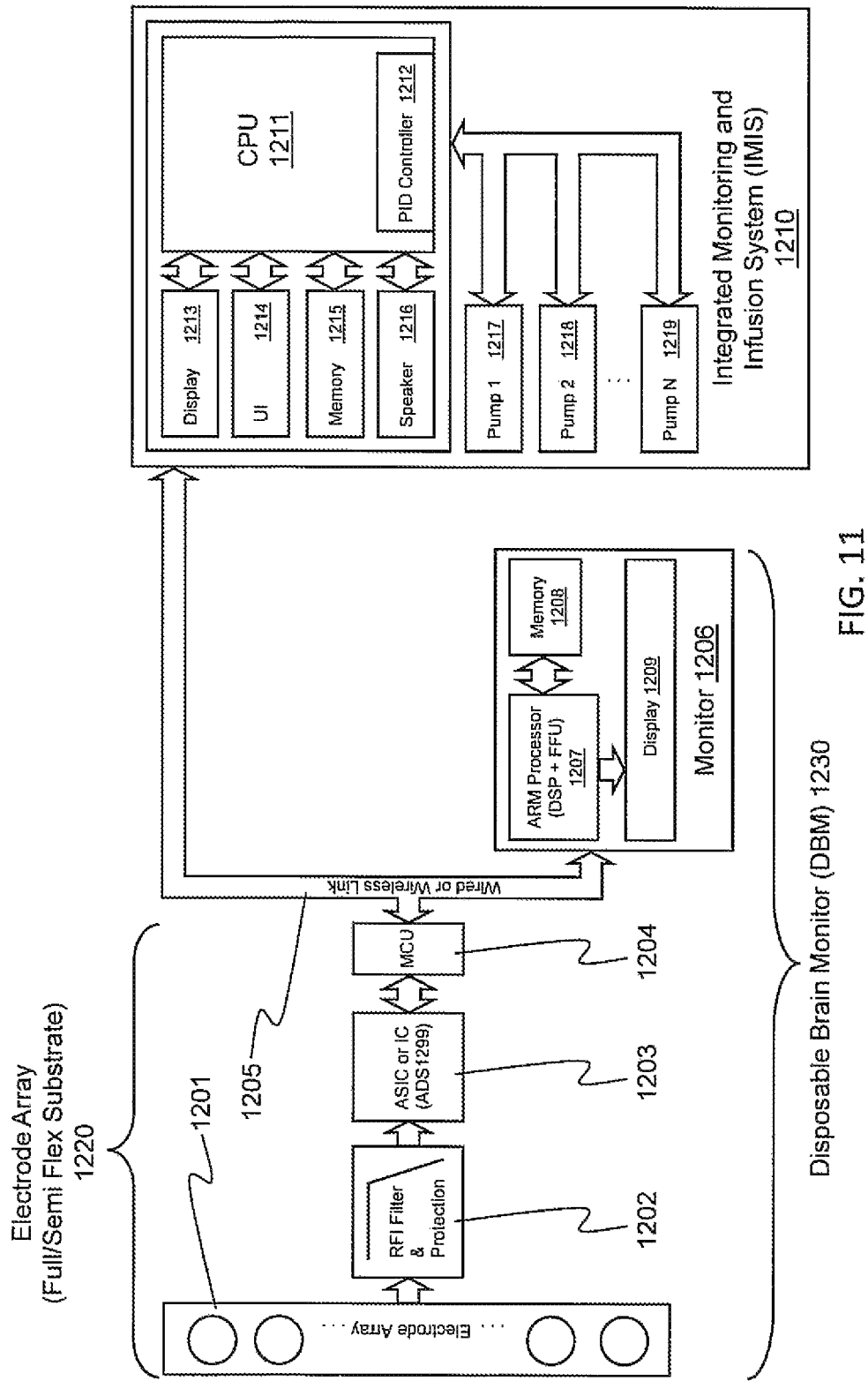
FIG. 11. Electrode/display integrated block diagram showing the arrangement of components in the DBM and IMIS.

In most embodiments, the IMIS embeds a graphical user interface (GUI), such as the one depicted in FIG. 11. The user interface, at a minimum, displays one or more EEG signals that are used to make the cortical activity level determination. The interface also displays the real-time cortical activity level, and its time course over time. A panel gives the user the ability of turning on or off the closed-loop feature, or to manually change the infusion rate. An emergency stop button allows the user to stop the infusion. Conversely, a bolus button allows the user to deliver a large amount of drugs in a short amount of time, e.g., to induce a patient into an anesthetic depth. An indicator on the cortical activity level time course shows the range of cortical activity level targeted by the system. Optionally, other graphs showing the estimated plasma and effect-site concentrations can be displayed to aid in the manual operation of the system. Also optionally, a future predicted time course of the plasma and effect-site concentrations, and/or effect can be displayed based on pre-programmed models. The future predicted time course can be useful to determine, for example, how long it will take to bring a patient into a lighter or deeper cortical activity level range, or to determine how long the closed-loop controller will take to bring the patient into the targeted zone. Another useful feature of the GUI is the creation of a data log. With each case, a data archive should be created containing at the very least the time course of the feedback variable (e.g., the $WAV_{CNS}$ index) as well as the controller outputs and the infusion pump rates. In some embodiments, the data log should also contain the user actions on the system, as well as a list of all the alarms and warnings during the case. The data log can be used for data audit purposes, or to serve as basis in future improvement of the system.

In a preferred embodiment, the GUI should be developed in such a way to minimize user confusion and user error while ensuring that the user verifies all the proper settings on the pump(s) and of the closed-loop system. A confirmation based GUI can be envisioned, where the user is asked to confirm his/her choices before being allowed to move to the next stage. Once all the confirmations have been obtained, the system allows the user to "close the loop."

The closed-loop feature of the IMIS is particularly useful in patients for whom the administration of total intravenous anesthesia (TIVA) is difficult or complicated by existing co-morbidities, in particular, for patients suffering from hepatic/renal failure, hemodynamic instability, or hypovolemia.

Although the illustrations (e.g., FIGS. 9-11) show a GUI integrated into the IMIS, the IMIS in some embodiments may be controlled by a separate display/interface device, such as a smartphone, tablet computer, portable computer, medical grade computer monitor, or other similar device, which is connected to the IMIS by wired or wireless connection.

Preferably, the IMIS calculates the drugs minimum and maximum dosage as recommended by the drug manufacturer, based on the weight of the patient or subject, and/or other parameters as discussed herein or as would be known to a person skilled in the art. These one or more parameters may be entered by the user or responder prior to the administration of drug to the patient or subject through the GUI. The GUI preferably asks the user or responder to confirm entered parameters prior to administration of drug to the patient or subject, and provides for sensible error-checking to prevent entry of unlikely parameter values or combinations of parameter values. For example, an entry of 2,000 pounds for human subject weight is likely to be the result of a mis-entry, such as one too many zeroes input for the weight value. The user of the system may override the minimum and maximum dosages at any time. Preferably, the device is configured so as to make it impossible to administer the drug outside of either the drug manufacturer recommended dosages or outside the dosing limits specified by the user. As such, the IMIS provides for safety and risk mitigation.

FIG. 1A is a depiction of one embodiment of the present invention in use. In this particular embodiment, a soldier 5 is applying the device 15 and 20 to an injured subject 10 in the field (not shown) or otherwise at the point of injury (POI). The device in the embodiment illustrated in FIG. 1A comprises an electrode array 15 and a display 20. The electrode array is embedded into a flexible substrate and applied to the forehead of the injured subject 10. The electrode array acquires EEG signals from the injured subject 10, and those signals, or processed signals derived therefrom, are transmitted to the display 20. The display then provides an indication as to the status of the subject. In some embodiments, the electrode array has channels 25 that extend back towards the back of the subject's head and are used for monitoring parietal channel connection. Although the connection 17 between the electrode array 15 and the display 20 is illustrated as being a wired connection, the connection may be wireless, using such protocols as Bluetooth, WiFi, cellular (3G, 4G, etc.), etc. In some embodiments, a smartphone, tablet computer, watch computer, portable computer, medical grade computer monitor, or other similar device may serve as the display 20 and may connect wirelessly or by wired connection to the electrode array 15.

The "flexible substrate" of the electrode array 15 of the device described above may be full-flexible, rigid-flexible, or semi-flexible. "Full-flexible" means all of substrate and embedded or otherwise affixed electronics are flexible. "Rigid-flexible" means that rigid electronic components, such as ICs, are embedded in a flexible substrate. "Semi-flexible" means that the substrate and embedded or otherwise affixed electronics, while somewhat pliant, have a limited, lower or lesser degree of flexibility than a substrate generally considered "flexible." In some embodiments, preferably, the substrate and embedded or otherwise affixed components are full-flexible. For reasons of cost, however, in some embodiments the substrate and embedded or otherwise affixed components are only rigid-flexible.

Importantly, the electrode array 15 as shown in FIGS. 1-4 is capable of a range of acquisition and processing steps before acquired and processed signals are transmitted on to the display 20 where they may optionally undergo further processing prior to display of an output. At the least, surface potentials are transduced into electrical signals by electrodes connected to or embedded in the electrode array. Preferably, those signals are also amplified by one or more electronic components embedded in or otherwise affixed to the electrode array. Further preferably, those signals are filtered before and/or after being amplified by one or more electronic components embedded in or otherwise affixed to the electrode array. Further preferably, those signals are digitized by one or more electronic components embedded in or otherwise affixed to the electrode array. Preferably, the digitized signals are further processed by one or more algorithms embedded in one or more electronic components embedded in or otherwise affixed to the electrode array. This digital processing may digitally filter artifacts from the acquired signals, may compute an index based on the acquired EEG signals (as described below), and/or may arrive at a simplified output for display (e.g., one or more of seizing/not seizing; normal/abnormal brain activity; conscious/unconscious; suppression/no suppression; and/or some indication of the level of alertness and/or sedation, such as awake/light sedation/moderate sedation/deep sedation/no cortical activity). Also preferably, one or more components embedded in or otherwise affixed to the electrode array further provide over-voltage protection. The ability for this processing to take place in close physical proximity to the electrodes minimizes noise and artifacts, since electrode leads can introduce motion artifacts and noise from external sources, e.g., electromagnetic interference from lighting systems such as common fluorescent light bulbs or RF communications systems such as common cellular telephones. The embodiments illustrated eliminate transmission of raw unprocessed analog signals through leads to the extent possible by providing amplification, filtering, digitization and processing in an apparatus as near as possible to the signal source. Preferably, all of the above steps are performed essentially directly on the subject's forehead, which is to say that components for performing all the above steps are preferably embedded in or otherwise affixed to the electrode array of the illustrated embodiments. Therefore, preferably, the only signals transmitted over the connection 17 between the electrode array 15 and the display 20 are digital signals. In these ways, the present invention greatly reduces artifacts and noise and produces a much more reliable and robust assessment of brain dysfunction, sedation, etc.

Since the electrode array 15 is preferably disposable in order to eliminate the need for cleaning, sanitizing, refurbishing (including re-gelling any gelled electrodes and recharging and/or replacing batteries), restocking, etc., and the costs associated therewith, it may be preferable in some instances for expensive and/or more reusable components to be provided in the display 20 rather than in the electrode array 15. One such component might be a touchscreen in the display by which a user or responder could operate the device of the present invention through a graphical user interface. Since the display may be a computing device unto itself and may be capable of processing of the acquired signals, some electronic processing components may be provided in the electrode array while others are provided in the display. However, as discussed above, it is an object of the present invention to perform as much of the processing as possible as near as possible to the point of signal acquisition, and to transmit only processed digital signals to the display. Furthermore, it is envisioned that in some embodiments, no touchscreen or other expensive components will be necessary to the operation of the device, and that even the cost of touchscreens may in the future become such that a touchscreen could be reasonably considered to be a disposable component. Thus, FIG. 1B envisions the same system as illustrated in FIG. 1A, but with all the components of the display integrated into the electrode array 15. The display in this (or any) instance may be as simple as one or more LEDs which light to indicate a condition or status, or may be as sophisticated as a touchscreen with a GUI. Eliminating the separate display and providing the display on the disposable portion of the device may increase the cost associated with disposability but simplifies operation of the device, since there is no need to connect to a separate display for operation.

FIG. 2A is a depiction of another field of use of the present invention. Rather than a warfighter or battlefield deployment, a sports application is depicted. Here, the injured subject 55 sustains an injury, and the first responder 50 (e.g., coach, trainer, EMT, etc.) applies the device 60, 65 and 70 to the injured subject 55. In this embodiment, the device comprises an electrode array 60, 65 and a display 70. Much like the embodiment described above, the electrode array is embedded into a flexible substrate and applied to the forehead of the injured subject 55, but also an electrode is applied to the subject's temple 65. Again, the electrode array acquires EEG signals from the injured subject 55, and those signals are processed and transmitted to the display 70. The display then provides an indication as to the status of the subject. FIG. 2B illustrates an embodiment identical to the one shown in FIG. 2A but with the display integrated into the electrode array 60, which is preferably disposable, obviating the need for separate display and connection thereto.

FIG. 3A is a close-up depiction of an injured subject 100 with an electrode array 105 and 110 attached to his or her head, and the display 115. The electrode array is again embedded into a flexible substrate which is applied to the injured subject's 100 head. The forehead electrode portion 105 contains two electrodes, and a single electrode 110 extends to the subject's temple. The display 115 in this embodiment gives an indication of the subject's 100 consciousness level, or level of sedation/anesthesia. A single light or indicator may be used to indicate that the subject is fully conscious or awake 120. Similarly, a single light or indicator may be used to indicate that the subject's brain activity is completely suppressed or ceased 140. In some embodiments, the indication of too high a level of consciousness might trigger a connected IMIS (not shown) to supply additional sedative, anesthetic, analgesic, etc. in order to counteract the brain status. Some embodiments may utilize a bilateral monitoring method whereby the two hemispheres of the subject's brain. In such embodiments, lights or indicators may be utilized to show the level of sedation or anesthesia of each of those hemispheres individually, and as such at least two lights or indicators may be used to indicate the respective level of sedation/anesthesia for each hemisphere 125, 130, 135. In the particular embodiment shown, the indicator is on for "No cortical activity" 140, thus the subject is completely suppressed. Similarly to the embodiments shown in FIGS. 1B and 2B, FIG. 3B shows an embodiment like that of FIG. 3A but with the display integrated into the electrode array 105. As discussed elsewhere in this application, the display may be as simple as one or several LED lights or may be as complex as a touchscreen with a GUI. Even if the display is eliminated, the electrode array may in some embodiments provide a connector for connection to transfer data or recharge power, or may provide for wireless connection over a suitable wireless protocol to transfer data, in some embodiments in real time to provide remote monitoring of the patient or subject.

In any of the above-described embodiments, the electrode array 15, 60, 105 may have an adhesive layer to facilitate secure application to the skin, which initially is protected by a sanitary backing (not shown) which the user or responder 5, 50 peels off prior to application to the patient or subject 10, 55, 100. In addition to or in substitution of the adhesive layer, the electrode array may be secured to the patient by means of an elastic headband (not shown), strap (not shown), or other means known to persons skilled in the art.

Figure 4A:
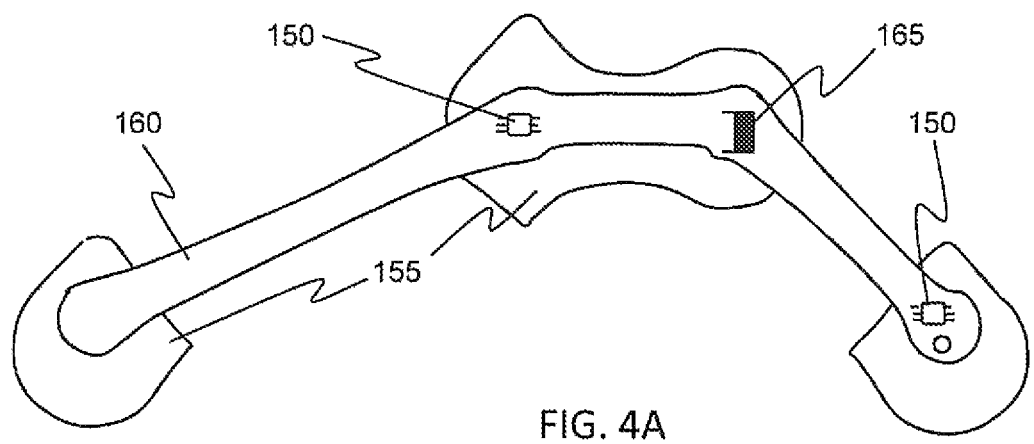
FIG. 4A. Depiction of one embodiment of the flexible substrate with electrode array.
Figure 4B:
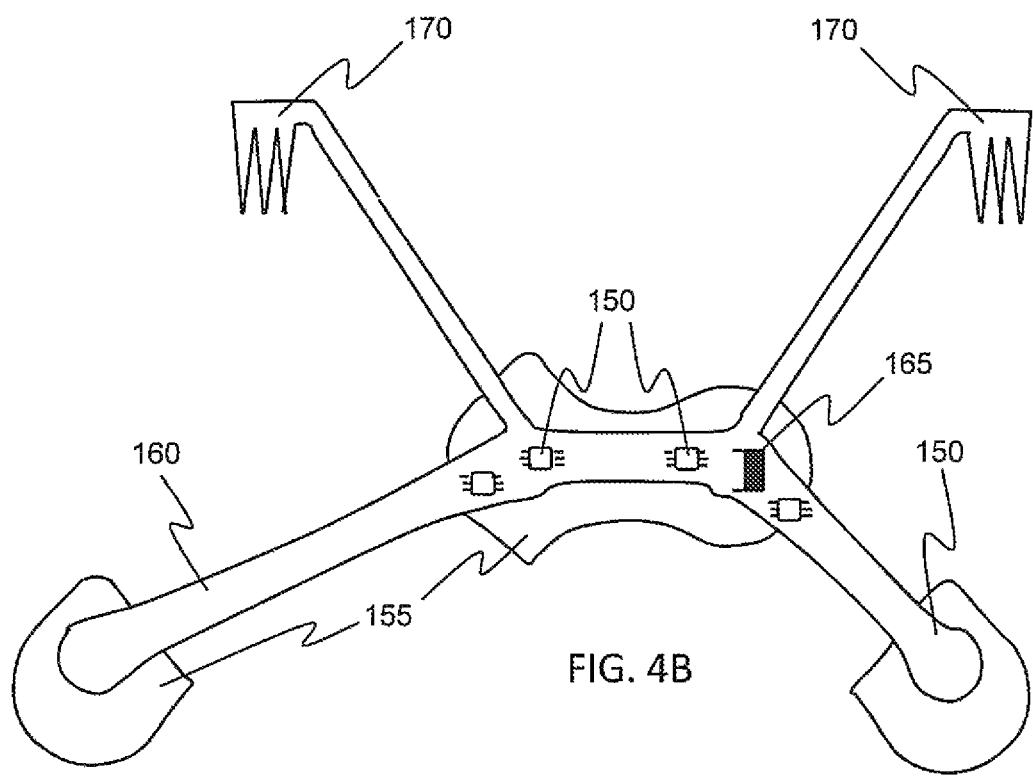
FIG. 4B. Depiction of another embodiment of the flexible substrate with electrode array, this one having semi-rigid comb structures used to help attach the electrode array to the subject's head in the presence of hair.
Figure 5A:
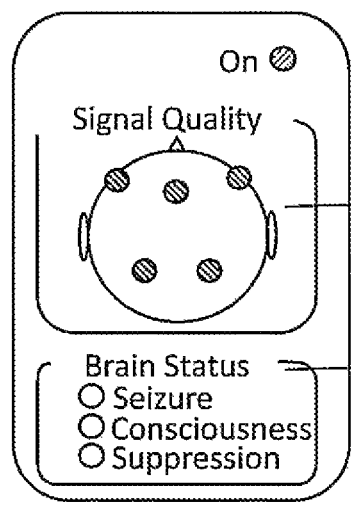
FIG. 5A. Depiction of an embodiment of the display portraying electrode signal quality and injured subject's brain activity with respect to potential presence or absence of seizure, consciousness or suppression.
Figure 5B:
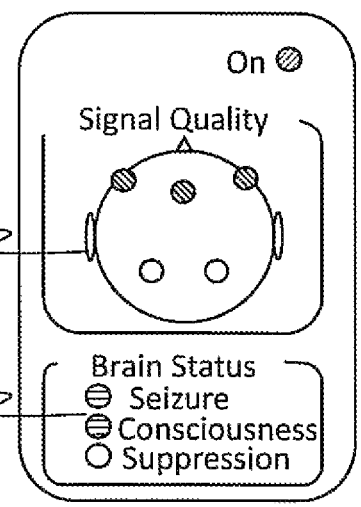
FIG. 5B. Depiction of an embodiment of the display portraying electrode signal quality and injured subject's brain activity with respect to potential presence or absence of seizure, consciousness or suppression.
Figure 5C:
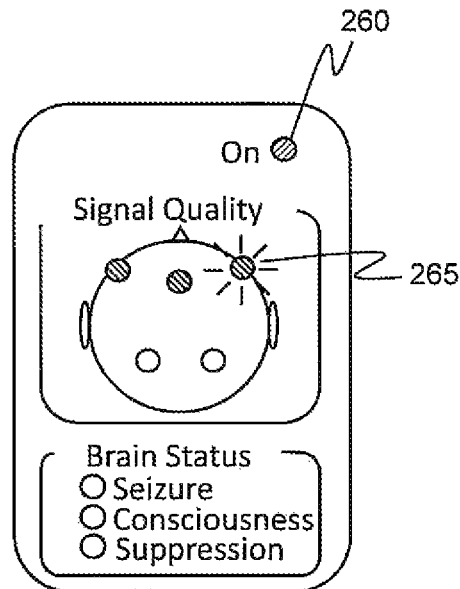
FIG. 5C. Depiction of an embodiment of the display portraying electrode signal quality and injured subject's brain activity with respect to potential presence or absence of seizure, consciousness or suppression.
Figure 5D:
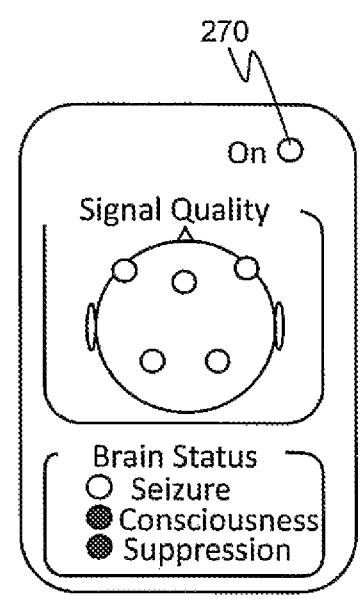
FIG. 5D. Depiction of an embodiment of the display portraying electrode signal quality and injured subject's brain activity with respect to potential presence or absence of seizure, consciousness or suppression.

FIGS. 4A and 4B depict two embodiments of the electrode array. FIG. 4A shows a flexible substrate 160 into which the electrodes (not shown) are embedded or otherwise affixed. The electrodes (not shown) are applied to the subject's (not shown) head and held down securely by adhesive pads 155. Aside from the electrodes, the flexible substrate 160 has embedded ASIC chips or other suitable ICs which comprise the amplification, filtering, and analog-to-digital conversion (signal pre-processing) electronics. Miniaturizing and embedding these ASIC chips or other suitable ICs into the flexible substrate serves to make the device a more integrated, portable, easy to apply device by removing the need for a separate processor to carry out these functions. Further, a connector 165 is provided which allows for the portable, in some embodiments disposable display unit (not shown) to be easily and quickly attached and detached from the electrode array. In FIG. 4B, all of the same features as in the FIG. 4A embodiment are present, with the addition of one or more semi-rigid comb structures 170 which are used to help attach the electrode array to the subject's head in the presence of hair. These comb structures 170 are particularly useful for attaching electrodes for occipital and parietal channel monitoring. The geometry of the comb structures illustrated is intended only to be exemplary of a comb and not a preferred geometry. A person skilled in the art would appreciate that different comb tooth shapes and lengths would be more useful depending on the type and thickness of hair, and that optimal comb tooth shapes and lengths could be arrived at through routine experimentation.

FIGS. 5A through 5D depict an alternate display embodiment whereby signal quality and brain status are displayed simultaneously. Signal quality 250, which may provide a graphical display of the head of the subject or patient and thereby show the electrodes by their relative positions thereon, indicates the electrical impedance of the electrodes. When the electrical impedance of any of the electrodes becomes too high, indicating an issue with the electrode itself or the connection between the electrode and the subject's scalp, and indicator or light 265 alerts the responder or user that the signal quality is poor in that electrode. This alert allows the user or responder an opportunity to replace the electrode or reaffirm its connection. The indicator or light may perform its function by changing color (e.g., from green to yellow, orange, or red, or some sequence thereof as impedance progressively worsens), by blinking (e.g., by blinking progressively faster or more slowly as impedance worsens), by deactivating or de-lighting, or by any other means known in the art to attract the attention of the user. Such indicator or light preferably accompanied by an alert tone, bell or alarm issued from a loudspeaker (not shown) that is optionally provided within the display.

Additionally, the subject's brain status 255 is displayed. In the particular embodiment shown, lights or indicators are given for three different brain conditions: seizure, consciousness, and suppression, though others may additionally or alternatively be included. If any of these conditions are detected in the subject, the light or indicator alerts the responder or user. In some embodiments, the indication of one of these conditions might trigger an attached or integrated IMIS (not shown) to supply some drug in order to counteract the brain status. Additionally, an indicator 260 is provided to give notice of the status of the brain monitor itself. If the light is on (or a particular color, for example green, or in some other way is a positive indicator), that means the device is properly connected to the electrode array and that the device is adequately powered. If the light is off 270 (or has turned another particular color, for example red, or in some other way indicates negatively), then either the device has run out of power, or the electrode array is not connected, and thus the display indicates that no monitoring is taking place. A blinking light 270 (or indicator that progressively changes color from, for example, green to yellow to orange to red) may indicate failing battery power and thus provide warning that the system will cease operation soon.

Figure 6:
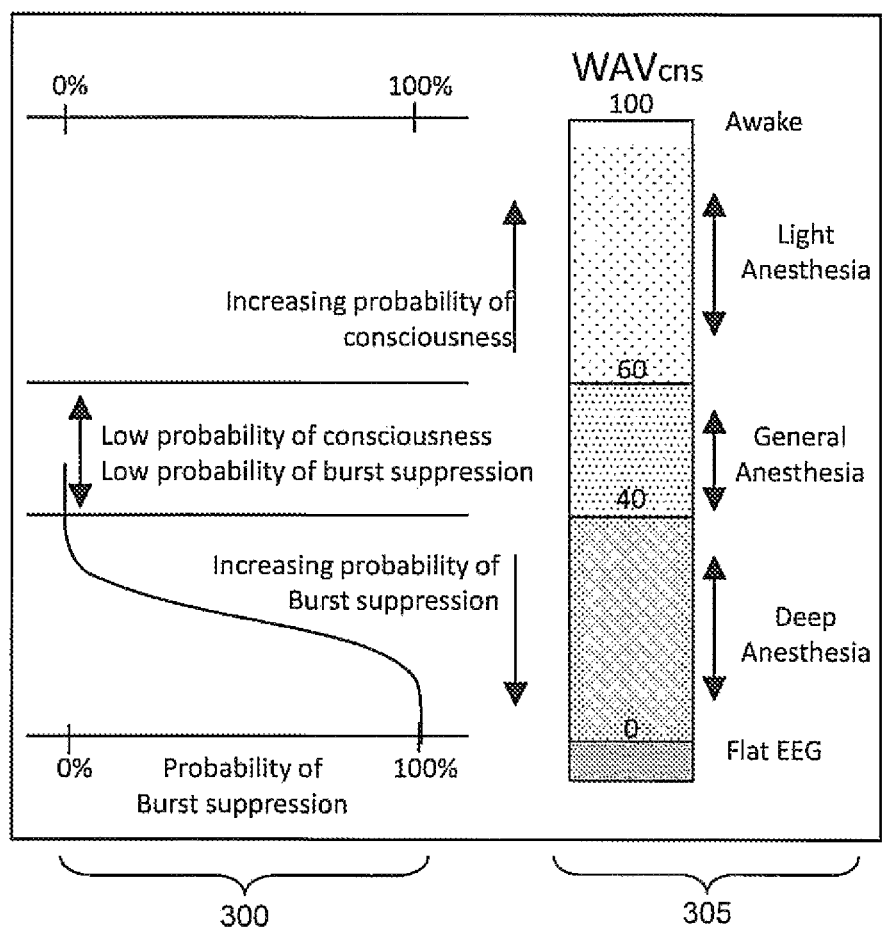
FIG. 6. Graph showing the correlation between the $WAV_{CNS}$ index (an indicator of consciousness used by the present invention) and subject consciousness or level of sedation or anesthesia.

FIG. 6 depicts the $WAV_{CNS}$ scale of the present invention, and provides a comparison of the particular $WAV_{CNS}$ index 305 numbers to the corresponding likelihood 300 of the subject being in a particular brain state. The $WAV_{CNS}$ scale represents the degree of cortical depression achieved through the administration of central nervous system (CNS) depressant drugs, such as sedatives or anesthetics. As the drug effect increases, the $WAV_{CNS}$ index decreases. When the $WAV_{CNS}$ index is at or near 100, it means the subject is very likely fully awake or conscious. As the drug begins to take effect, the patient enters a state of light anesthesia or sedation, and the $WAV_{CNS}$ index drops while the likelihood of the subject being fully conscious decreases. As the subject enters a level of general anesthesia or sedation, corresponding to a $WAV_{CNS}$ index of between 60 and 40, the subject has a very low probability of being conscious, but also a very low probability of burst suppression. However, if the drug effect continues to strengthen, the $WAV_{CNS}$ index drops further (e.g., below 40) and the subject enters deep anesthesia or sedation, and the likelihood of burst suppression activity increases.

Figure 7:
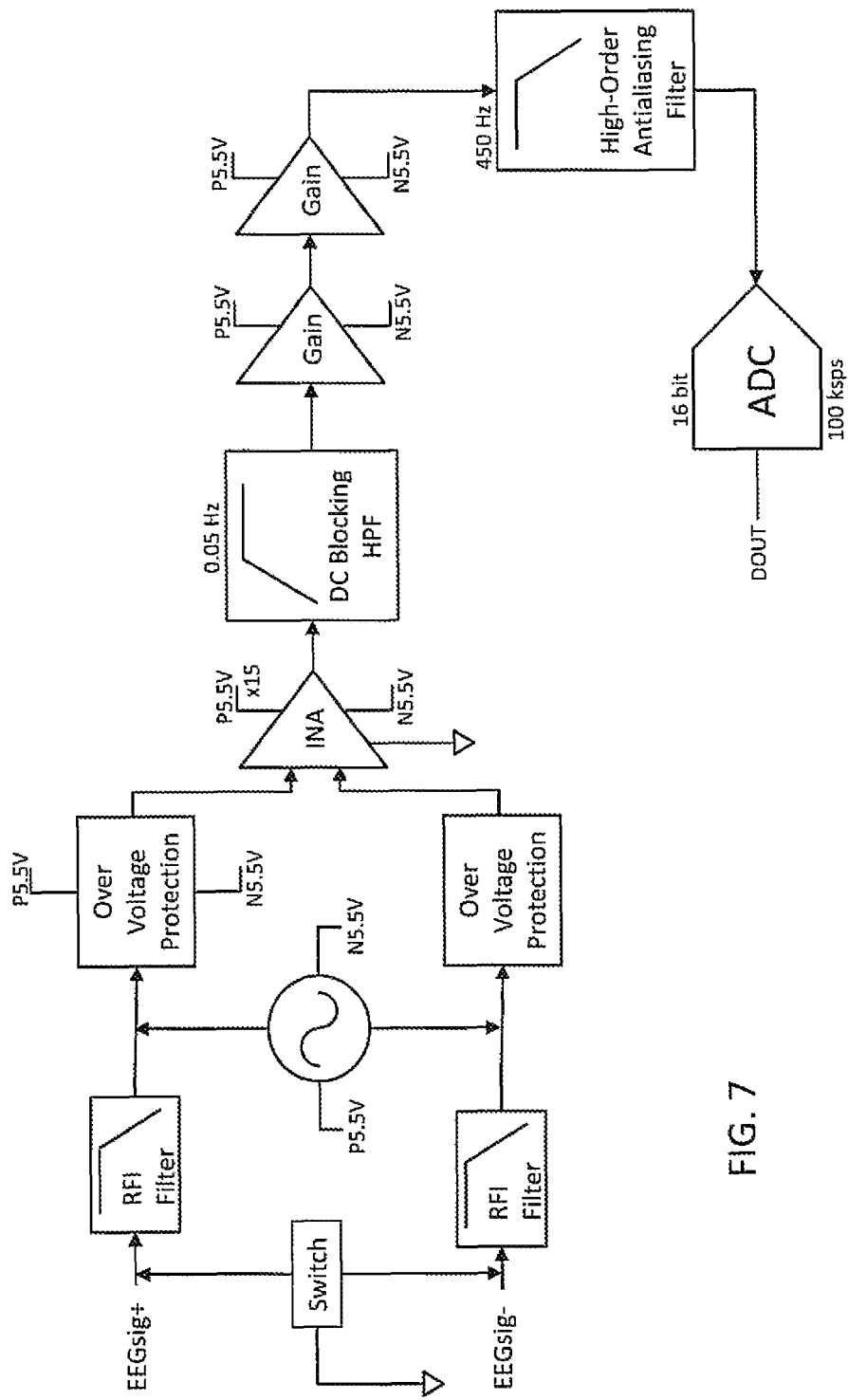
FIG. 7. Block diagram of an application-specific integrated circuit (ASIC) utilized in some embodiments of the device.

FIG. 7 is a block diagram of an application-specific integrated circuit (ASIC) used in certain embodiments of the present invention. The ASIC includes all the signal preprocessing function normally performed by a full-scale processor including amplification of the EEG signal, filtering of the signal, and analog-to-digital conversion. Preferably, the ASIC is constructed to be very small, substantially on the order of 0.2 square inches. Preferably, each channel of the disposable brain monitor has its own dedicated ASIC. This means that each channel has its own analog-to-digital converter, helping to minimize cross-talk between channels in the event that one or more channels should become disconnected during use. Separate amplification for each channel also minimizes amplifier noise, which leads to higher signal-to-noise and common-mode rejection ratios. More importantly, the ASIC chips consume extremely low power in comparison to general-purpose ICs, thus allowing the device to require lower power overall, permitting the device to require a smaller, lighter battery and helping to make the device lighter, longer-lasting, more portable, and disposable.

Figure 8:
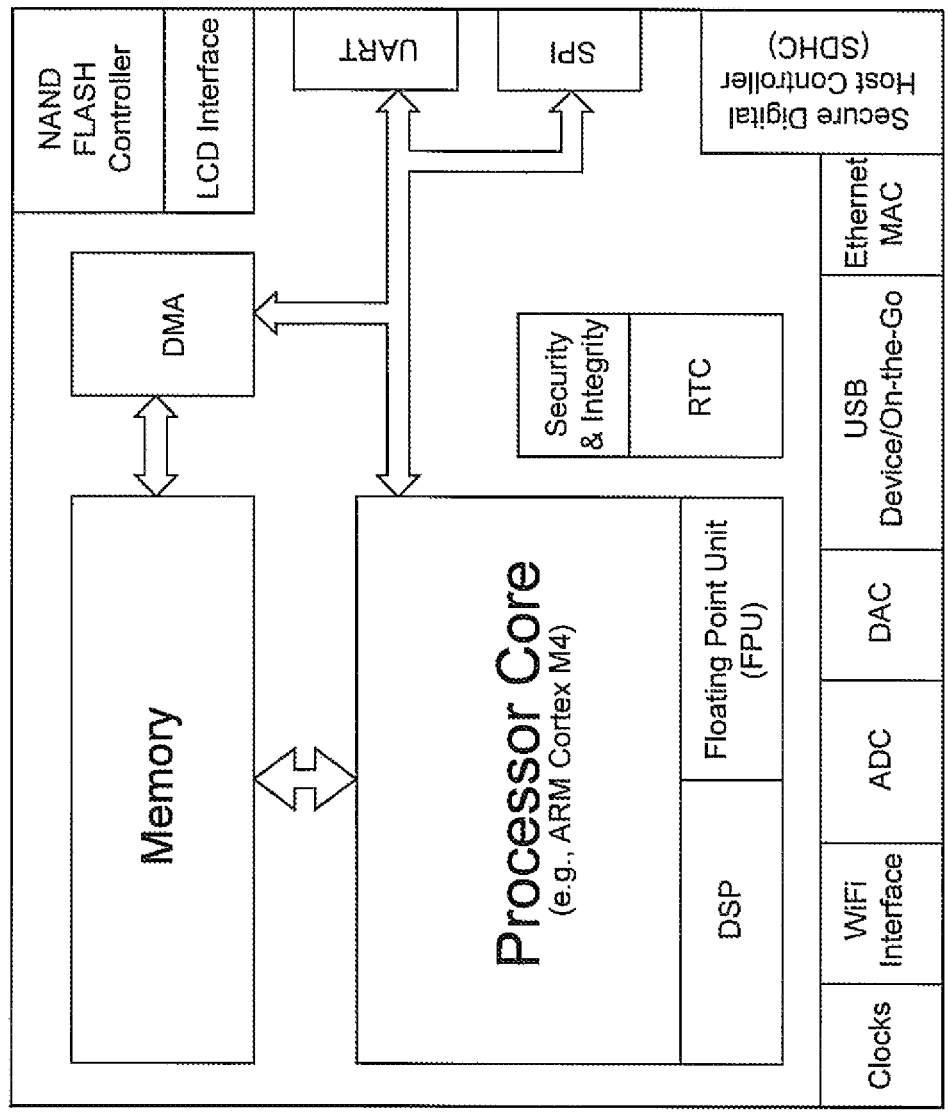
FIG. 8. System overview of one embodiment of the main processor for the disposable brain monitor (DBM).
Figure 9A:
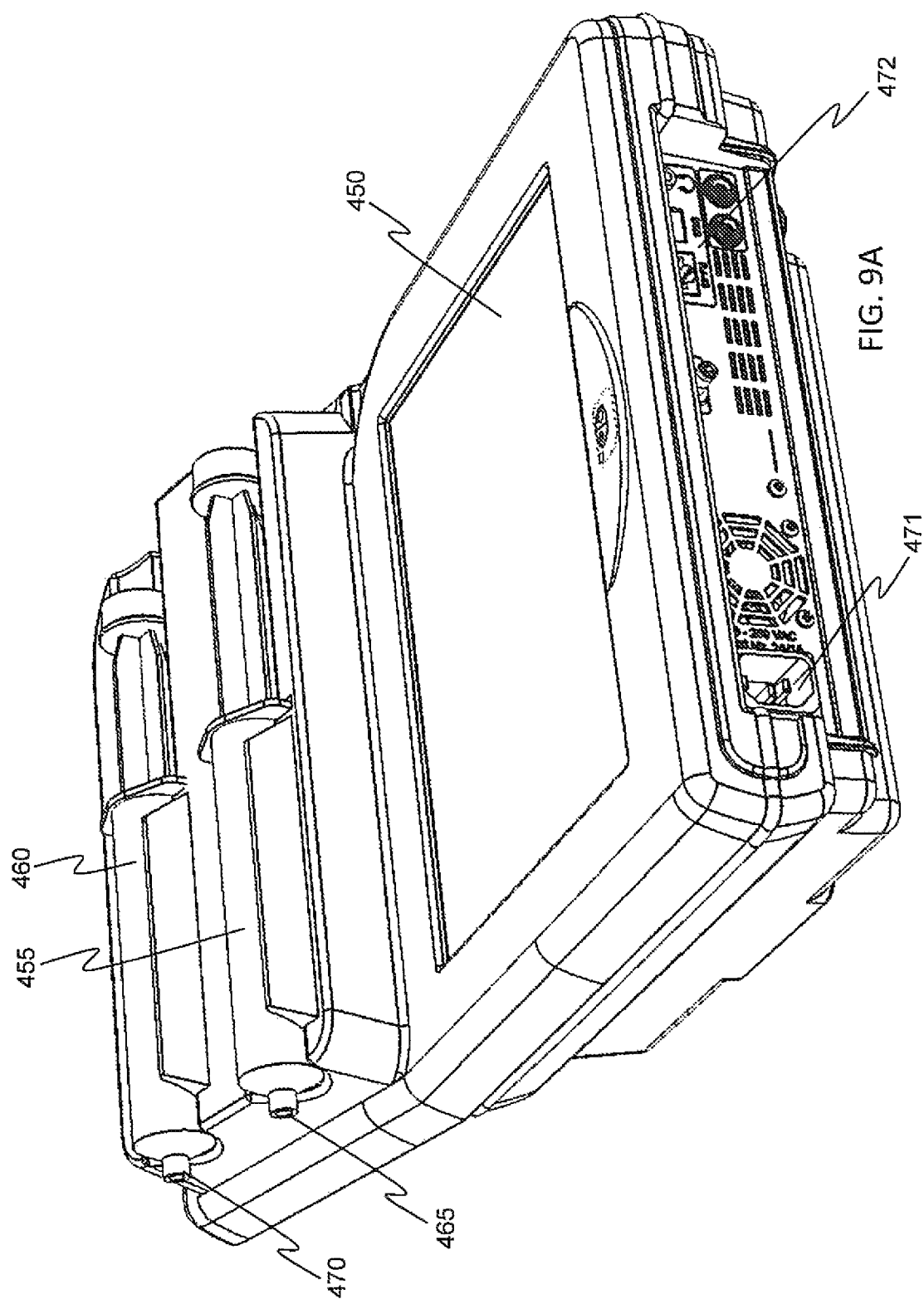
Figure 9C:
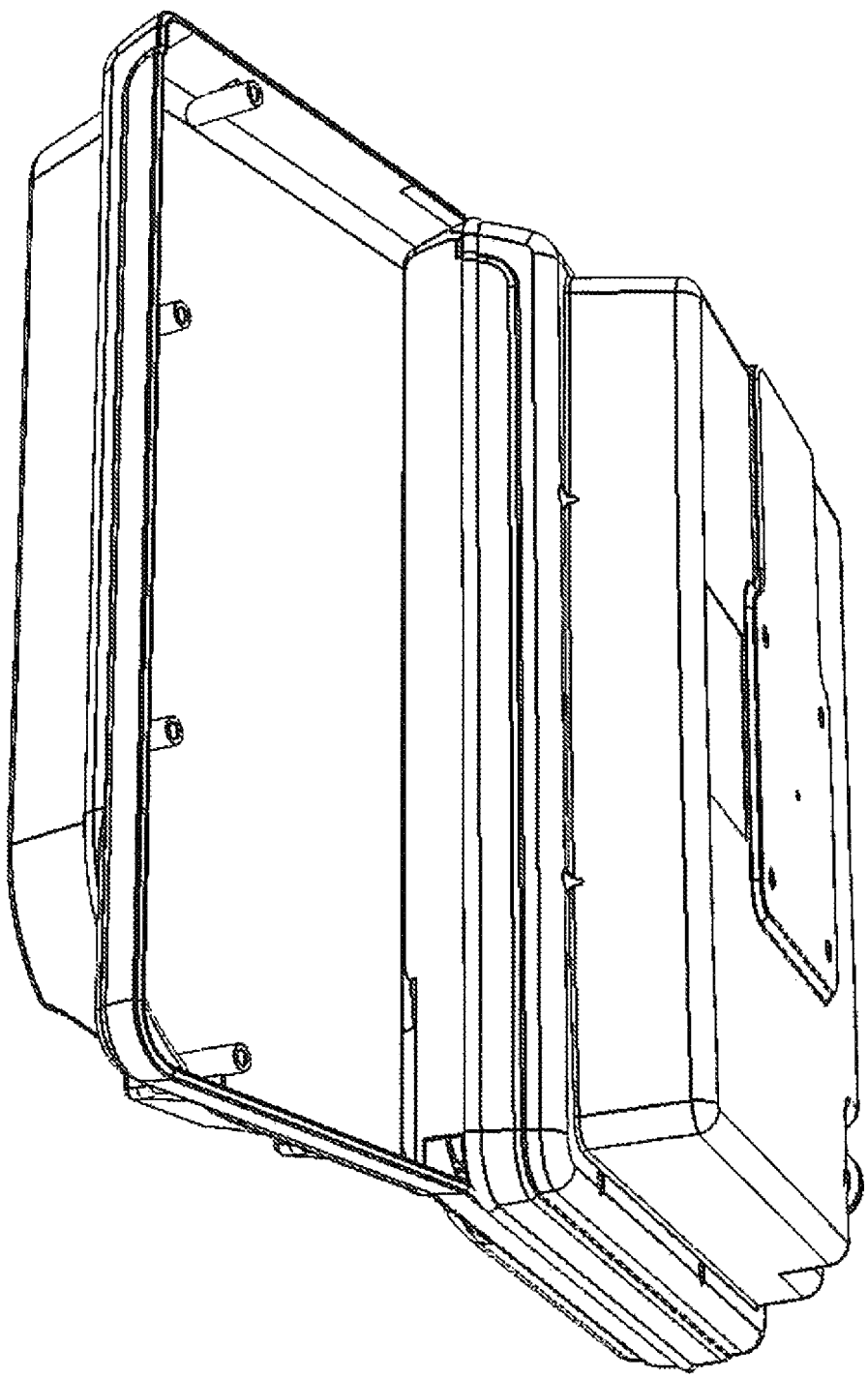
Figure 9D:
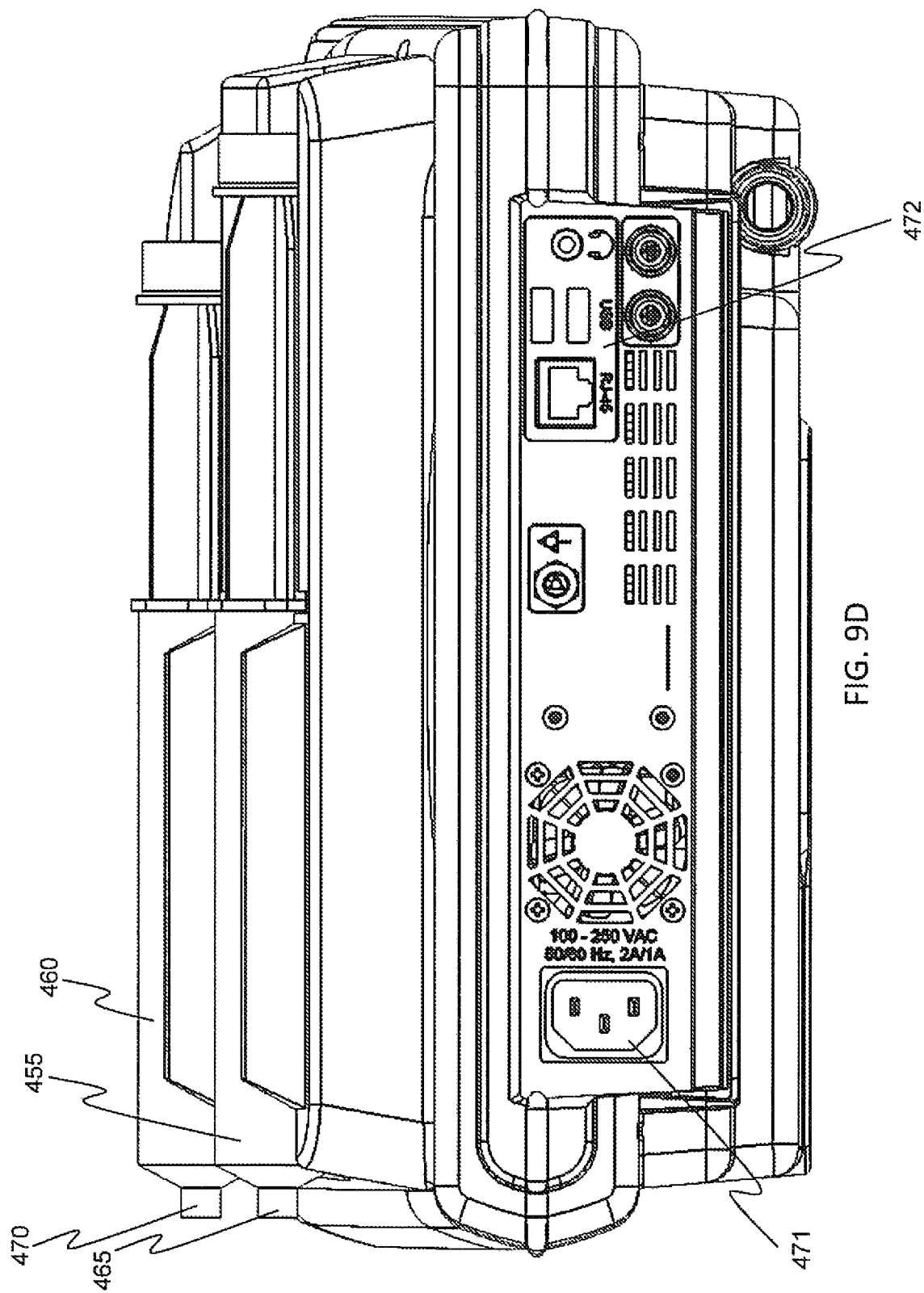
Figure 9E:
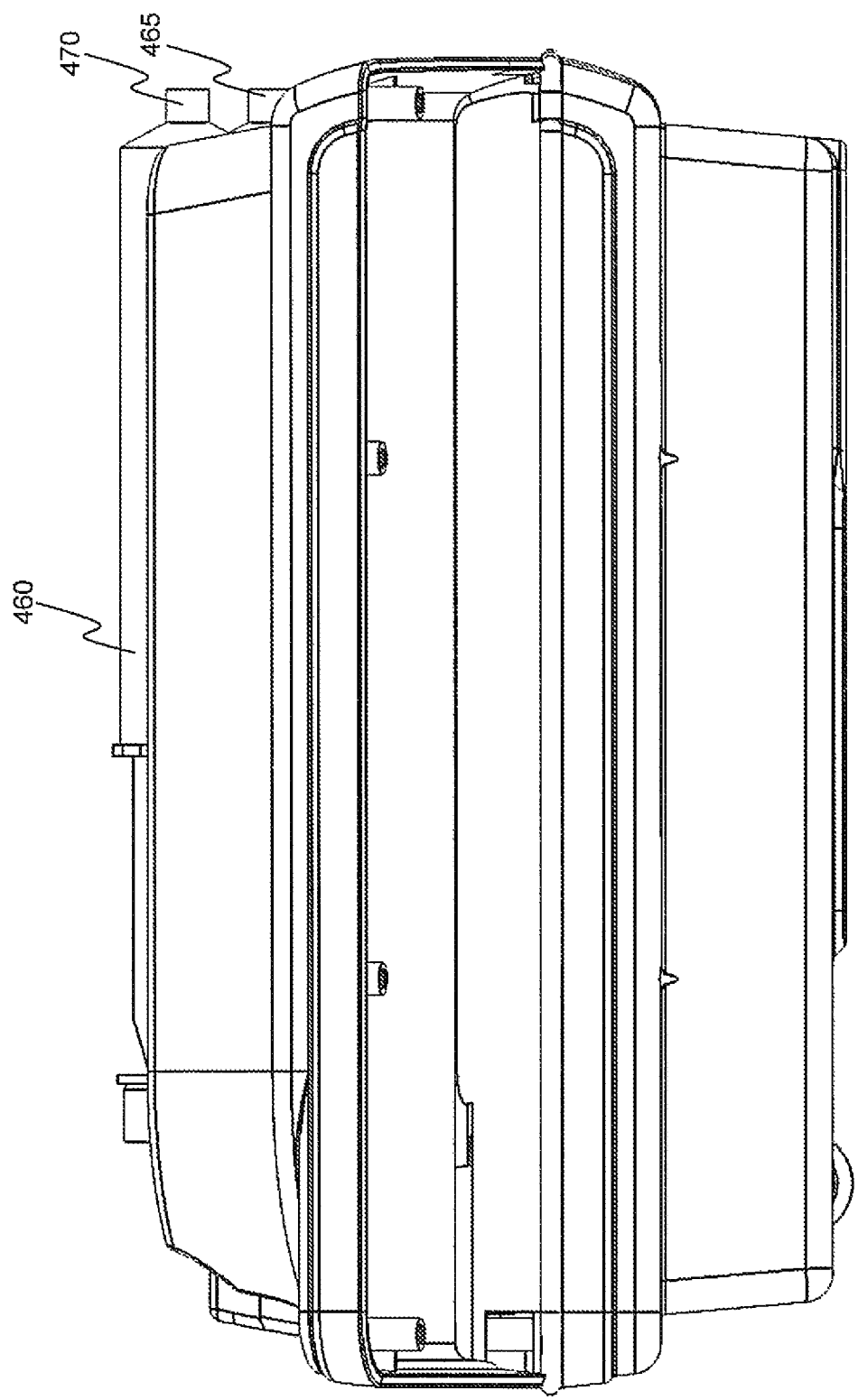
Figure 9F:
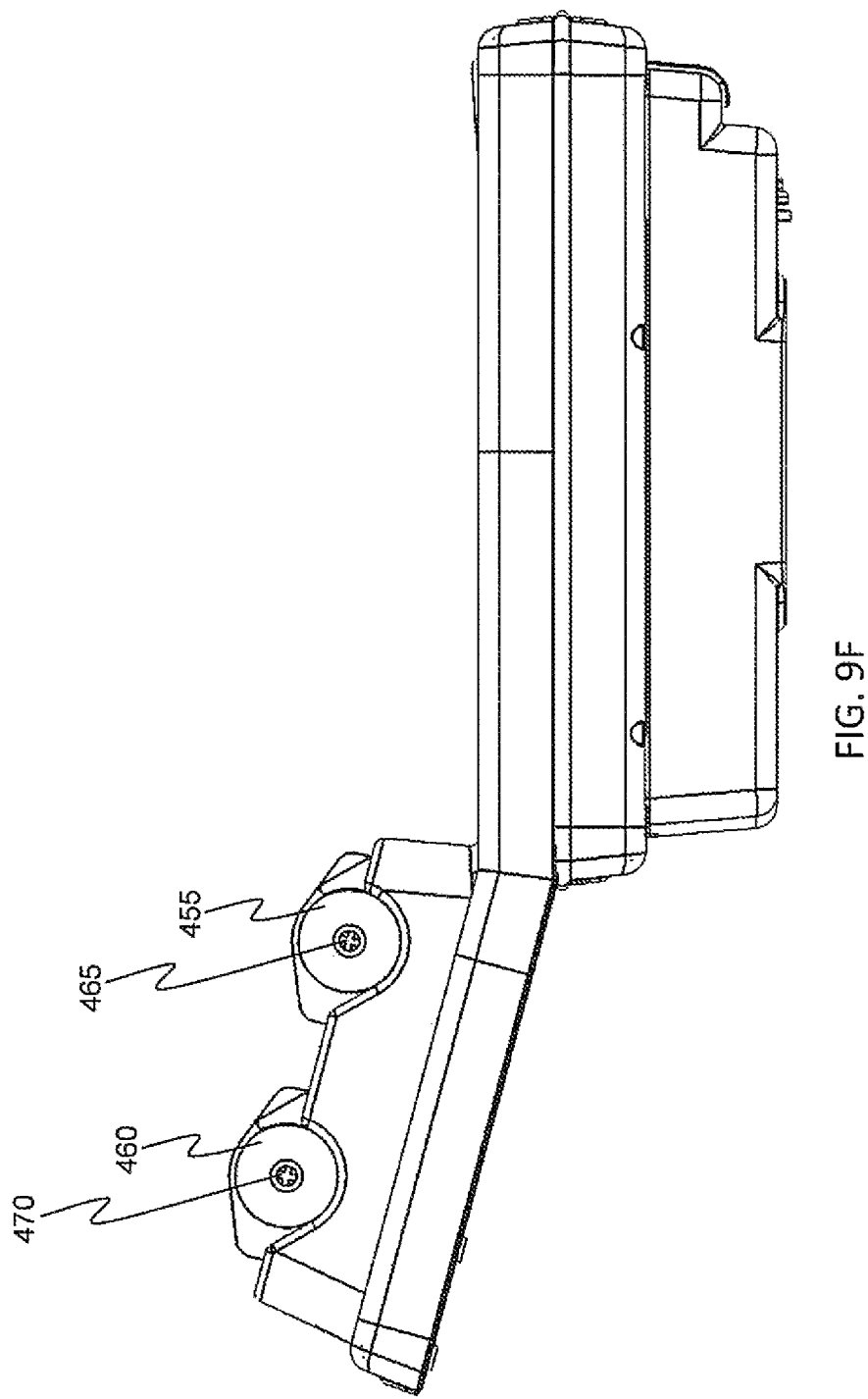
Figure 91:
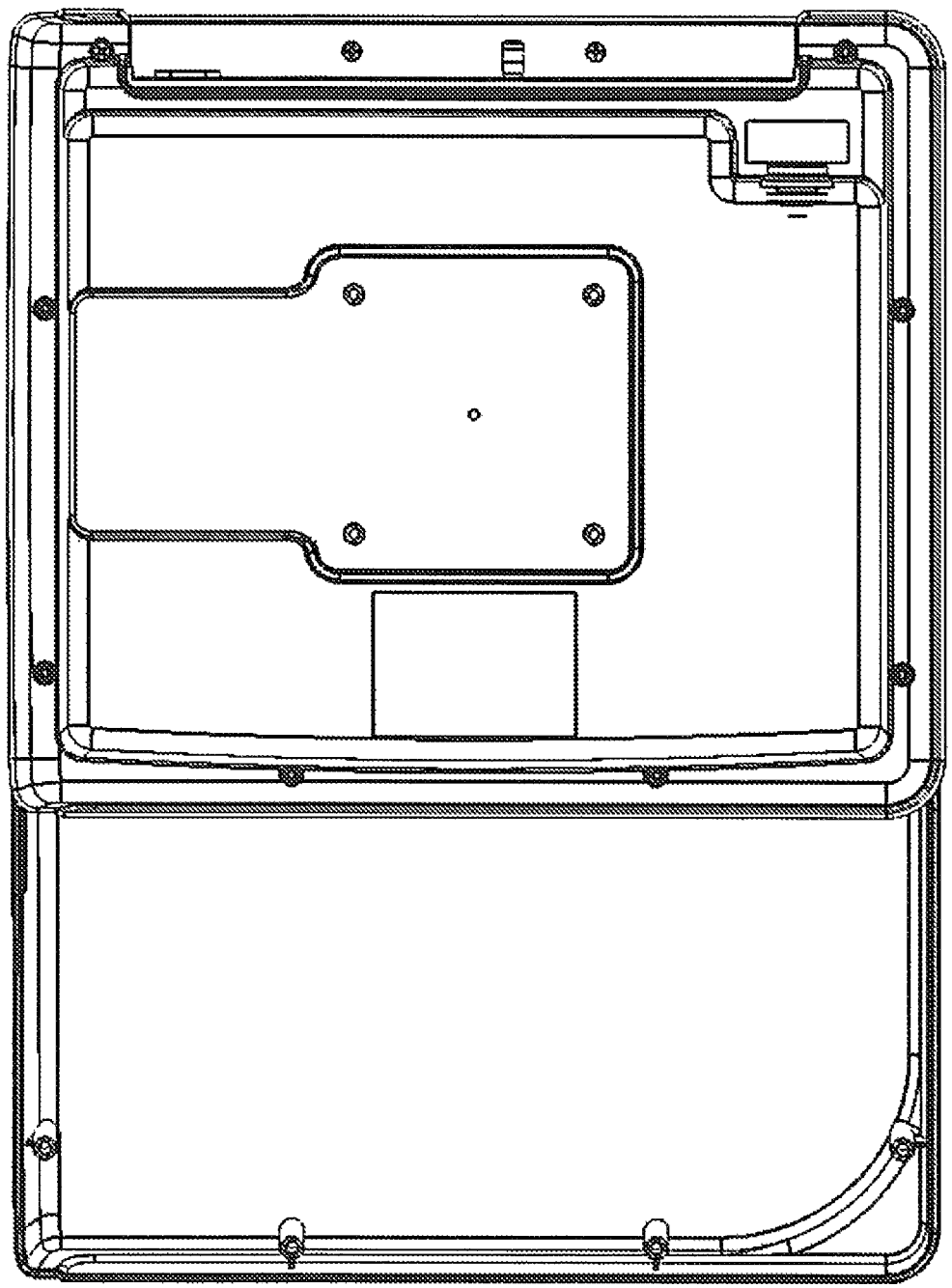
Figure 9J:
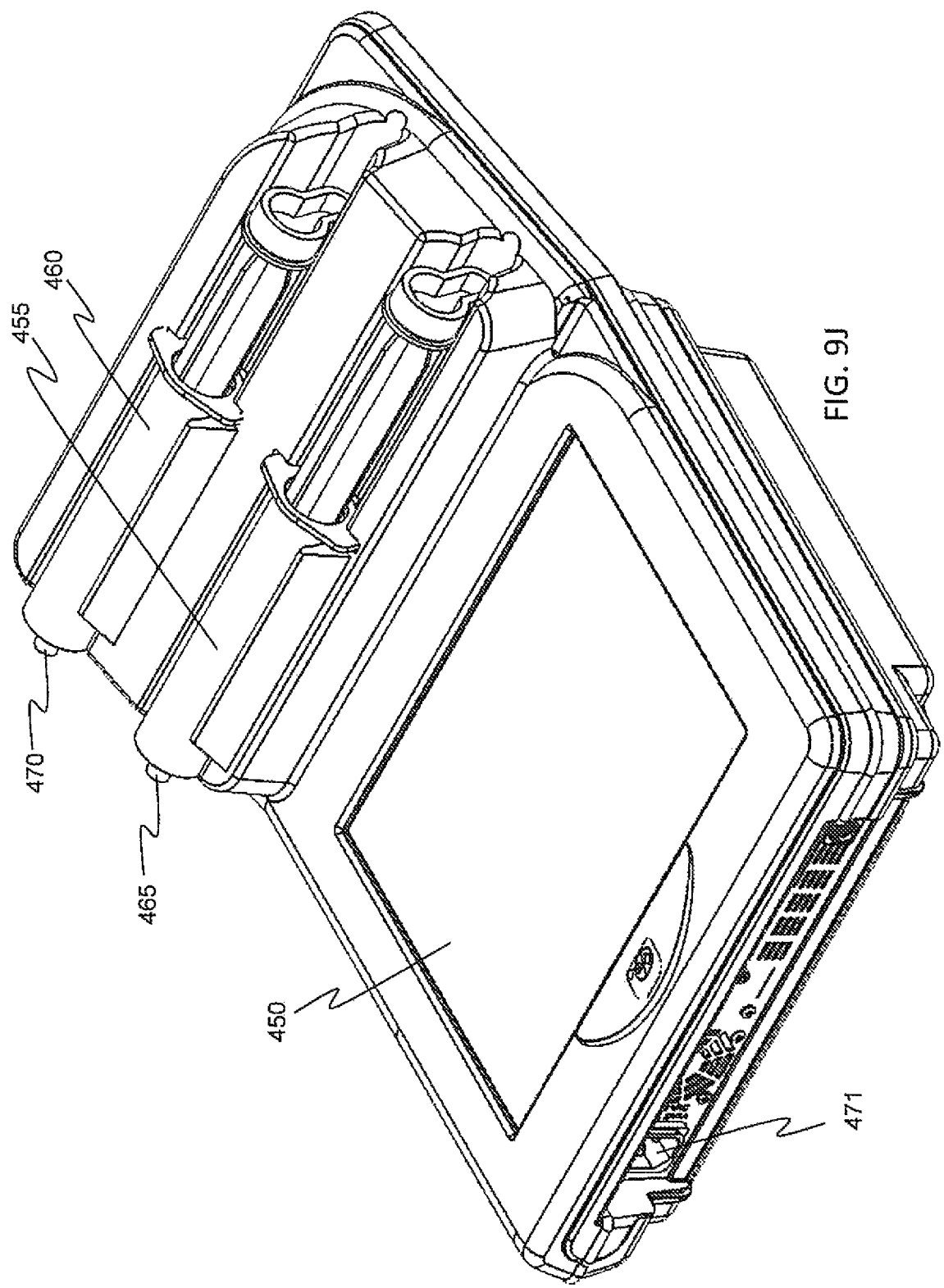

FIG. 8 is a list of features and components utilized in the disposable brain monitor's main processor. This processor is a micro-controller to help ensure the device is small, portable, and disposable, and was designed for mobile applications requiring small size and optimized power consumption. The processor is very low cost, and thus is easily integrated into a disposable product without significantly impacting the overall manufacturing costs. The exemplary depicted processor, an ARM Cortex-M4, provides all the necessary features required for processing a 4-channel EEG signal. First, the ARM processor embeds a powerful floating-point digital signal processor (DSP). This DSP is responsible for running in real-time all the processing algorithms including those for signal quality assessment, artifact detection and removal, seizure detection, cortical suppression detection and diminished consciousness detection.

The processor also features a 12-bit digital-to-analog converter (DAC), which can be used to generate the electrode impedance test signal. The present invention may preferably continuously perform impedance checking functions to verify the proper contact of the electrodes with the patient's skin. The impedance is measured by injecting a very small current at a predefined frequency, and measuring the voltage generated by this current across the electrodes. The frequency is typically outside the EEG bandwidth in order to avoid corruption of the signal of interest. The ARM DAC may be used to generate the sine waveform used to measure the electrode impedance.

Communication with the ASIC or IC chipsets may be carried out through a standard SPU/UART interface. The internal processor clock may sample each channel at 512 samples per second to guarantee a bandwidth up to 200 Hz. The ARM processor then outputs both the EEG and processed data onto its SPI bus or UART port.

FIGS. 9A through 9J illustrate different views of an embodiment of the IMIS device. The device comprises a display 450 and two syringe infusion pumps. The display 450 is used as a touchscreen user interface through which the user interacts with the device. Additionally, the display 450 is used to show any combination of indices, EEG signals, drug infusion rates, alerts or warnings, or any other information which may be useful or necessary to the user. The two syringe infusion pumps 455 and 460 are filled or attached to a drug source. Typically, at least one syringe infusion pump 455 is used to administer anesthetic or sedative medication. The second syringe infusion pump 460 may be an additional reservoir of anesthetic or sedative, or may be used to provide analgesic medication, or perhaps even muscle relaxation medication, or some other medication. Some embodiments may have more than two infusion pumps and thus provide any combination of these medications. The syringe infusion pumps 455 and 460 each have a line connection port 465 and 470, respectively, through which the medication is dispersed. A medical grade IV line is preferably used and connected to an IV inserted into the subject according to appropriate medical procedures. The drugs are pushed out of the syringe infusion pumps, through the line connection ports into the lines and thus into the subject.

The IMIS shown in FIGS. 9A through 9J may be powered by an internal battery (not illustrated), which may be replaceable or rechargeable, and/or by an external power source, and may be plugged in with any standard or special power connector. As illustrated, the IMIS has a standard IEC 60320 C14 AC power connector 471 and, internally, an AC-to-DC converter (not shown) allowing the IMIS to be plugged into a standard wall electrical outlet. Also, the IMIS embodiment illustrated has other connectors 472 such as RJ-45, USB, headphones, etc. for transfer of data and other signals to external sources. Additionally, the internal rechargeable battery of the IMIS may be recharged through any of the connectors 471, 472 which allow for transfer of electrical power, including the Ethernet port and the USB ports.

FIGS. 10A through 10H are screenshots of one embodiment of the display output of the IMIS system in use. The display is preferably a touchscreen interface which has integrated buttons, e.g., 520, 521, 522, by which the user can interact with the display. These touchscreen buttons allow the user to setup the device and begin its operation, change the display parameters, change the drug infusion rate, and otherwise interact with the device. In the upper left corner 500, the recorded EEG signals of each hemisphere are displayed individually. In the upper right corner 505, the WAV$_{CNS}$ index for each hemisphere is displayed individually, as well as the suppression ratio for each hemisphere. The lower left corner 510 shows a graph of the WAV$_{CNS}$ index for each hemisphere, but this corner may be programmed or adjusted to show other graphs, or multiple graphs at once, of different parameters, including WAV$_{CNS}$, suppression ratio, electromyography (EMG) activity in the signal, etc. The left-side portion has several touchscreen buttons which can be used to change the particular parameters which are displayed. The lower right side 515 displays the current volume of each drug (propofol and remifentanil in these particular screenshots) remaining in the device, or available to the system, as well as the rate of each drug's infusion. Each drug has its own window with control buttons thereby providing individual control for each drug. The user may also press the flag button 522 to insert flags 523 representative of important events or observations into the recorded data in real time. These flags can assist with later review of the data by marking such events or observations.

Figure 10A:
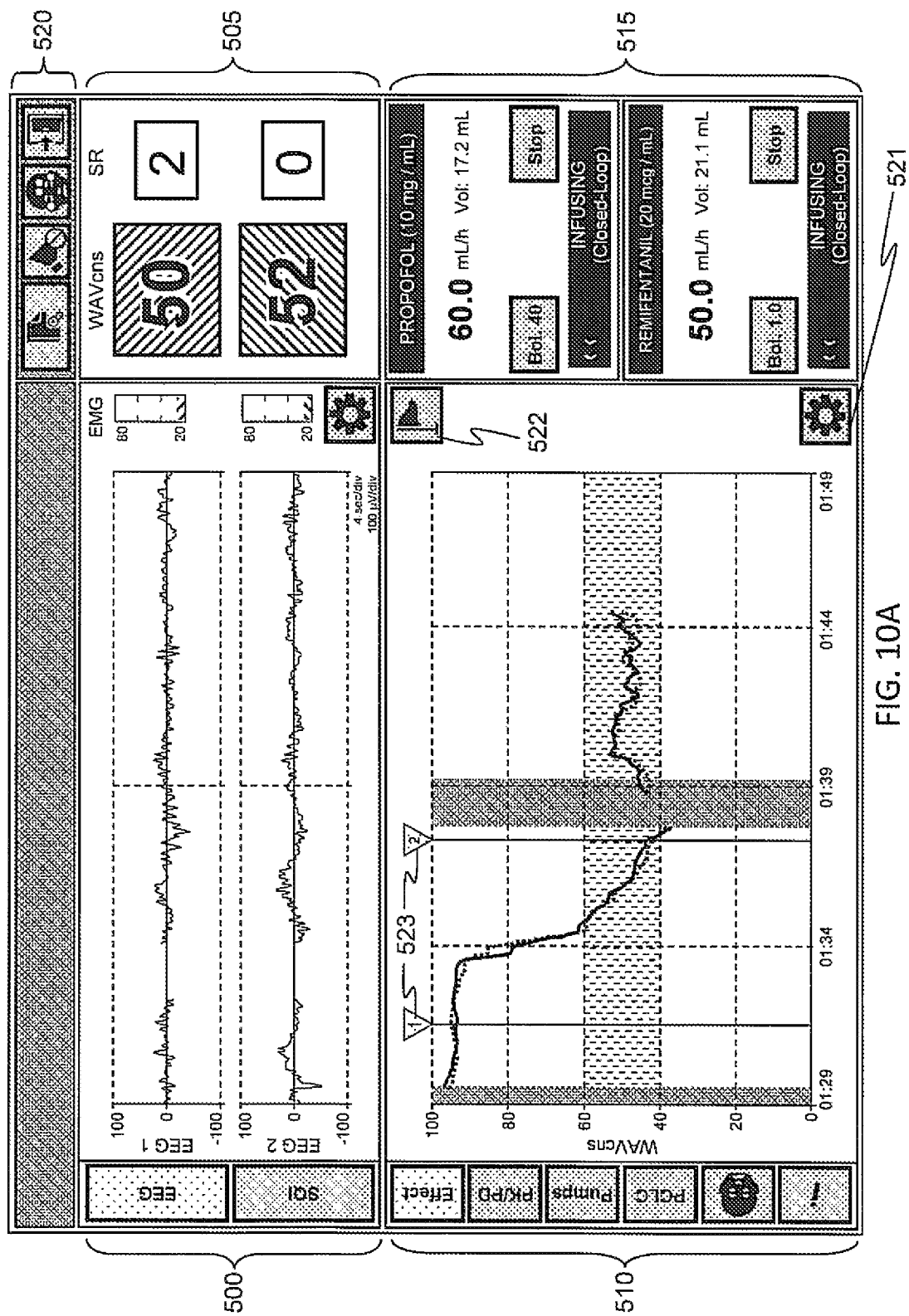
Figure 10B:
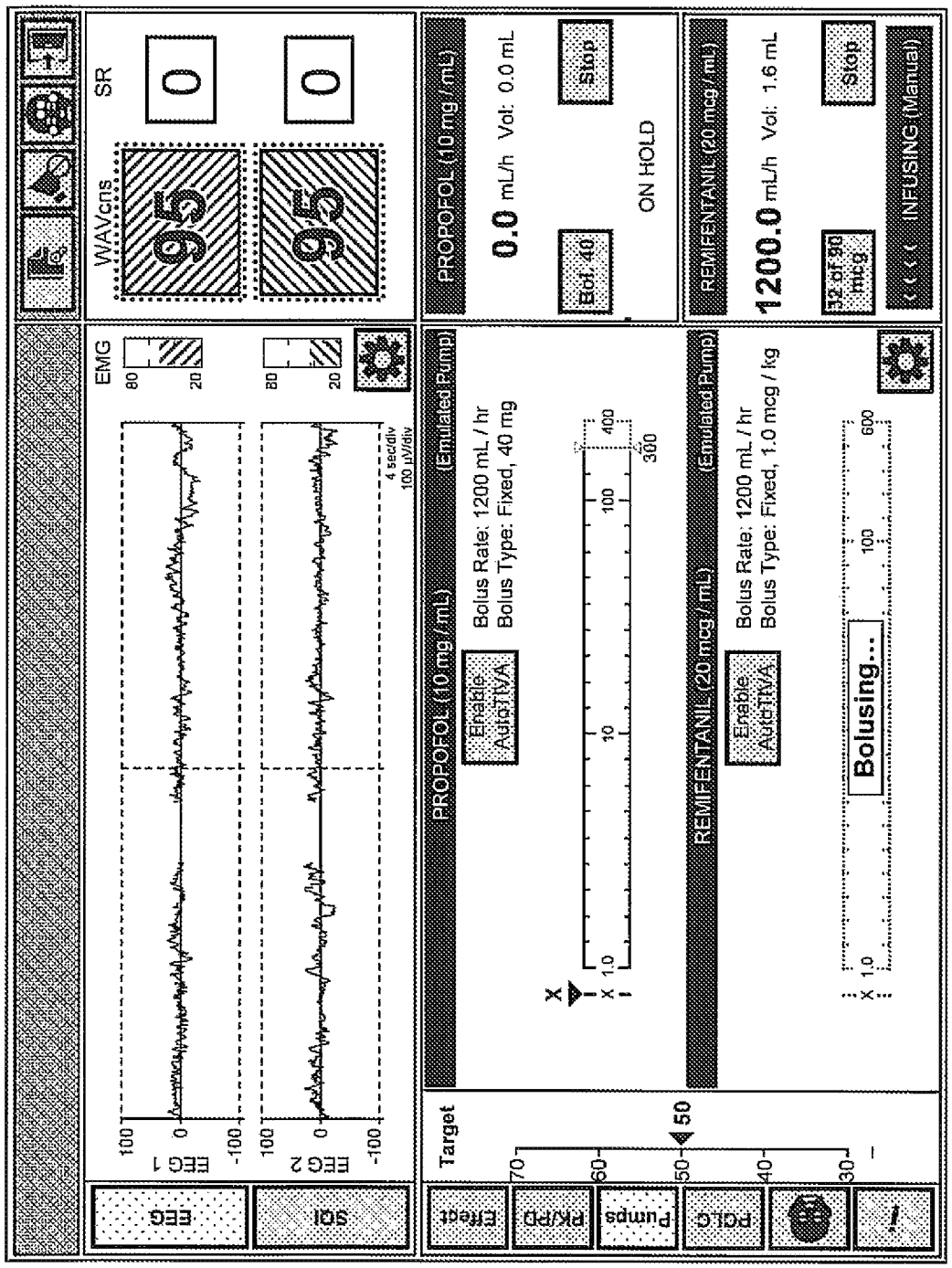
Figure 10C:
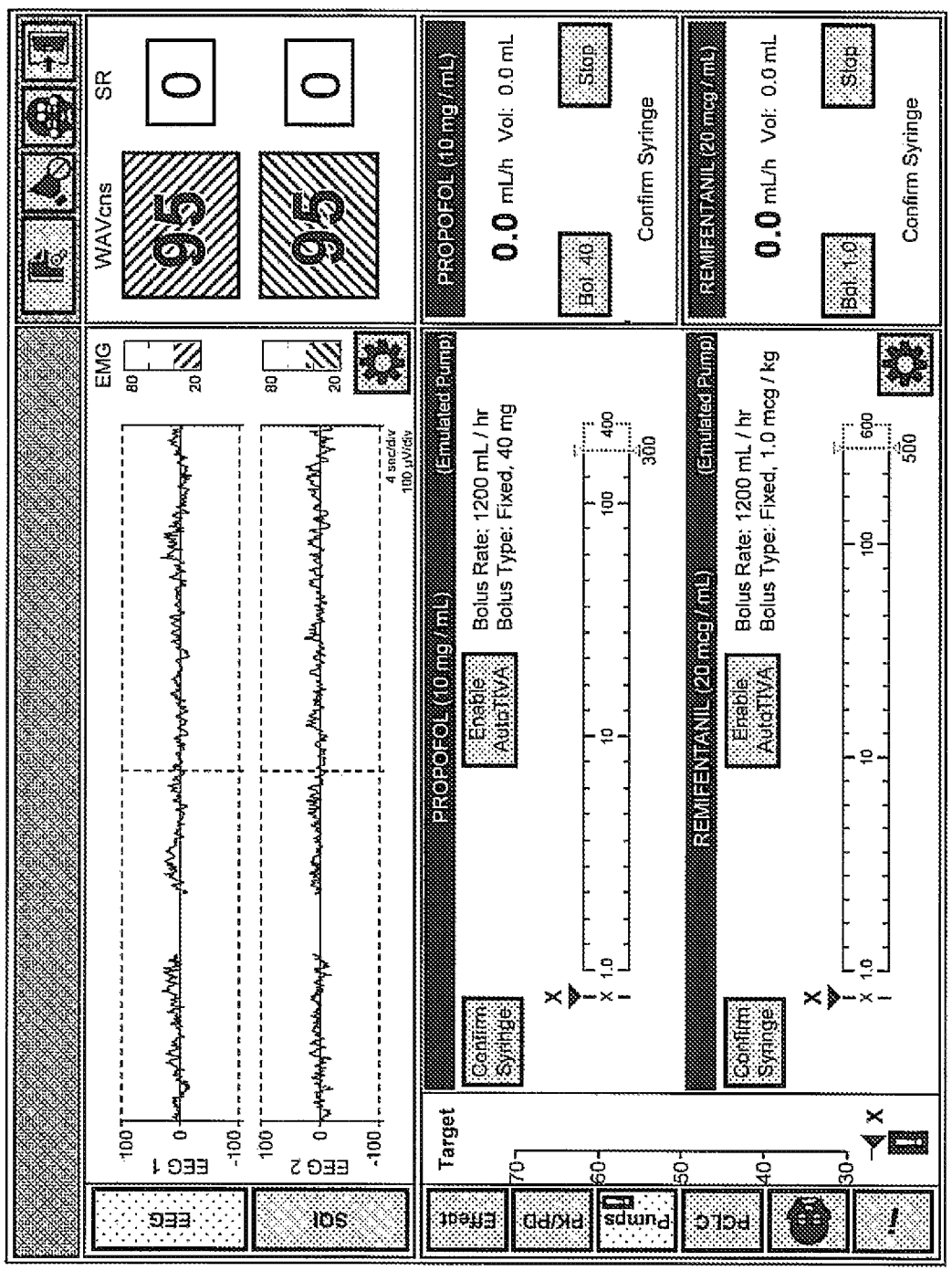

FIG. 10B shows how the drugs may be automatically infused by the system, or put on hold (propofol) or manually infused (remifentanil) in increments by the push of a button on the user interface.

Figure 10D:
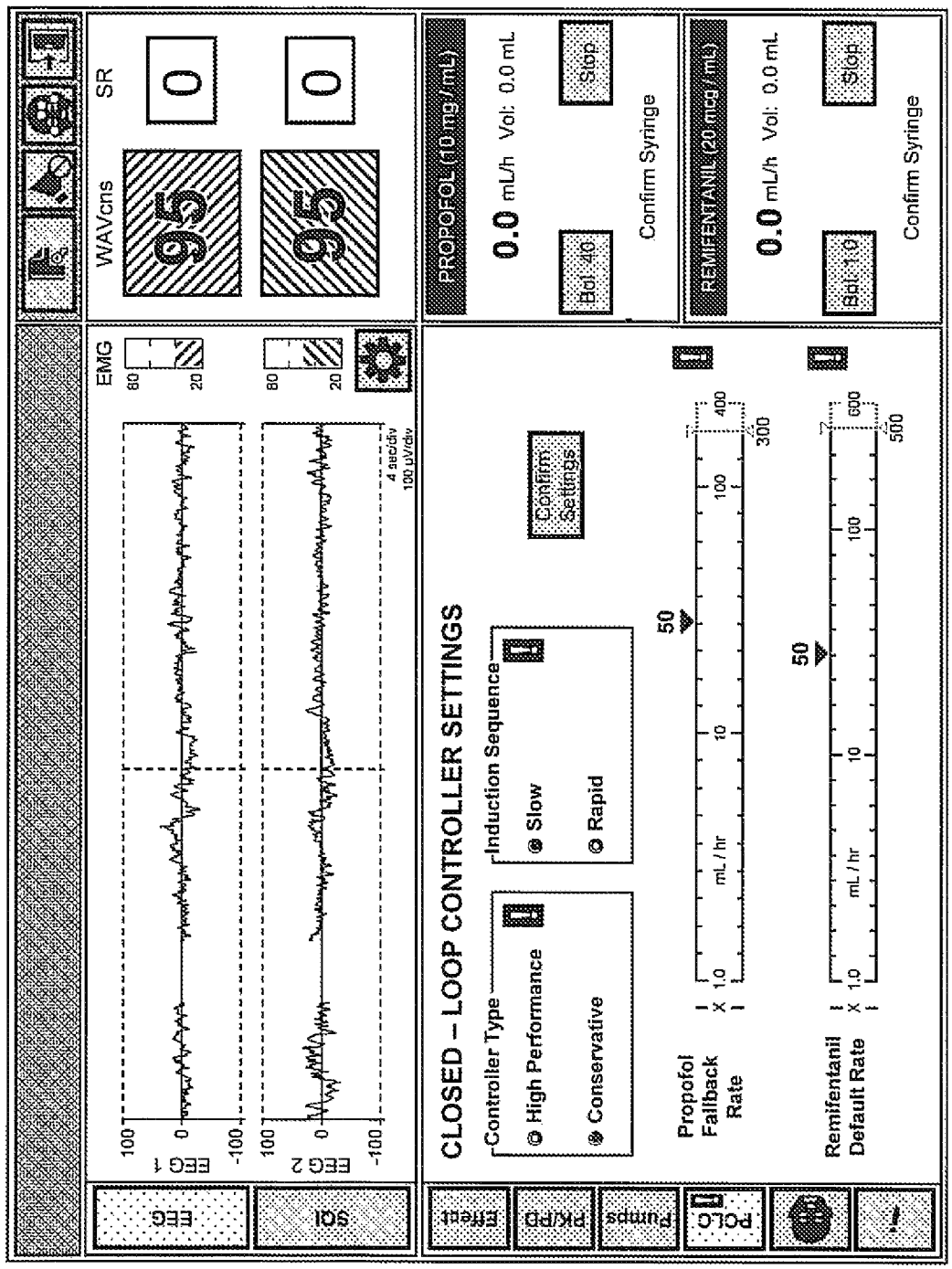
Figure 10E:
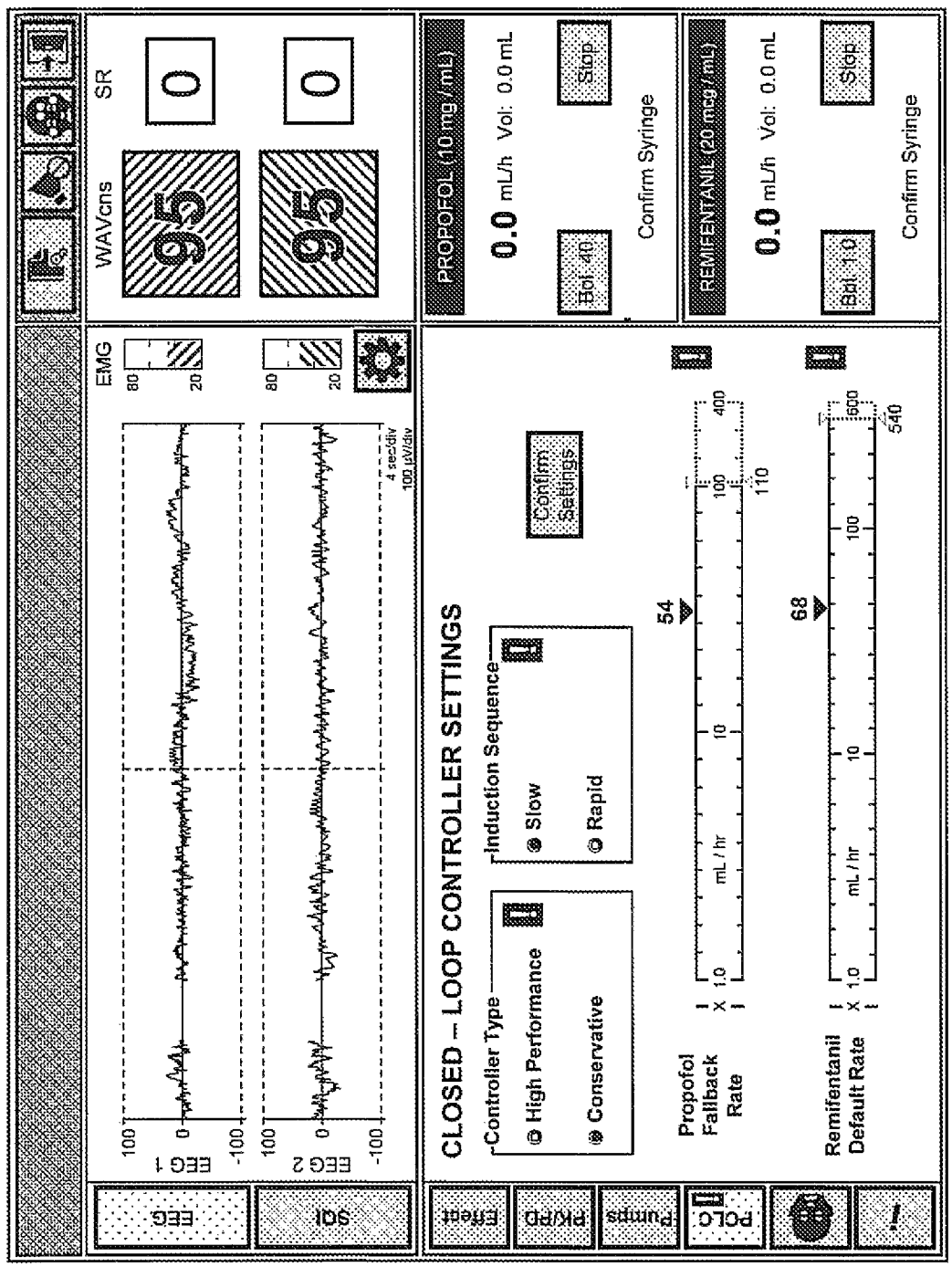
Figure 10F:
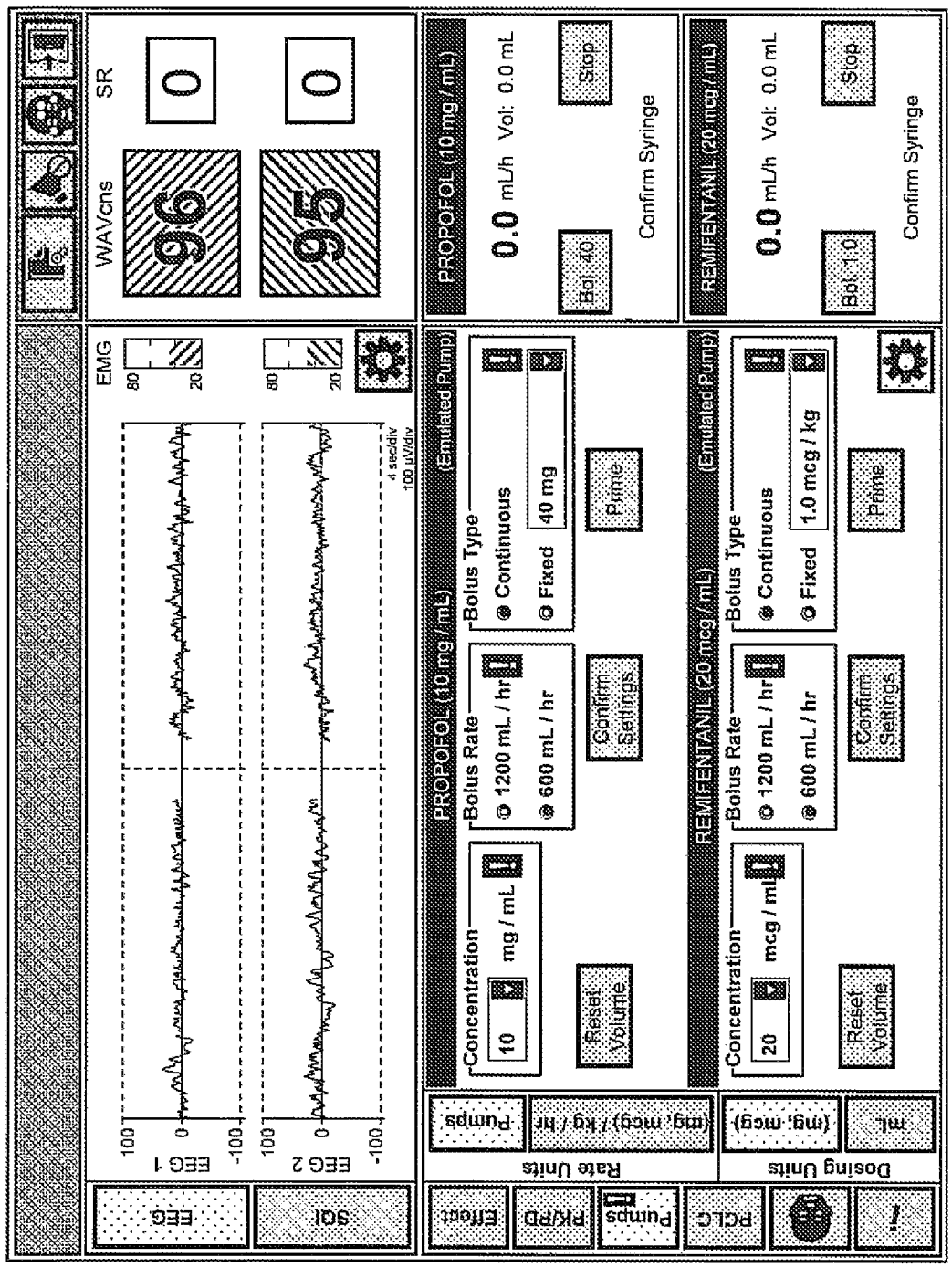
Figure 10G:
Figure 10H:
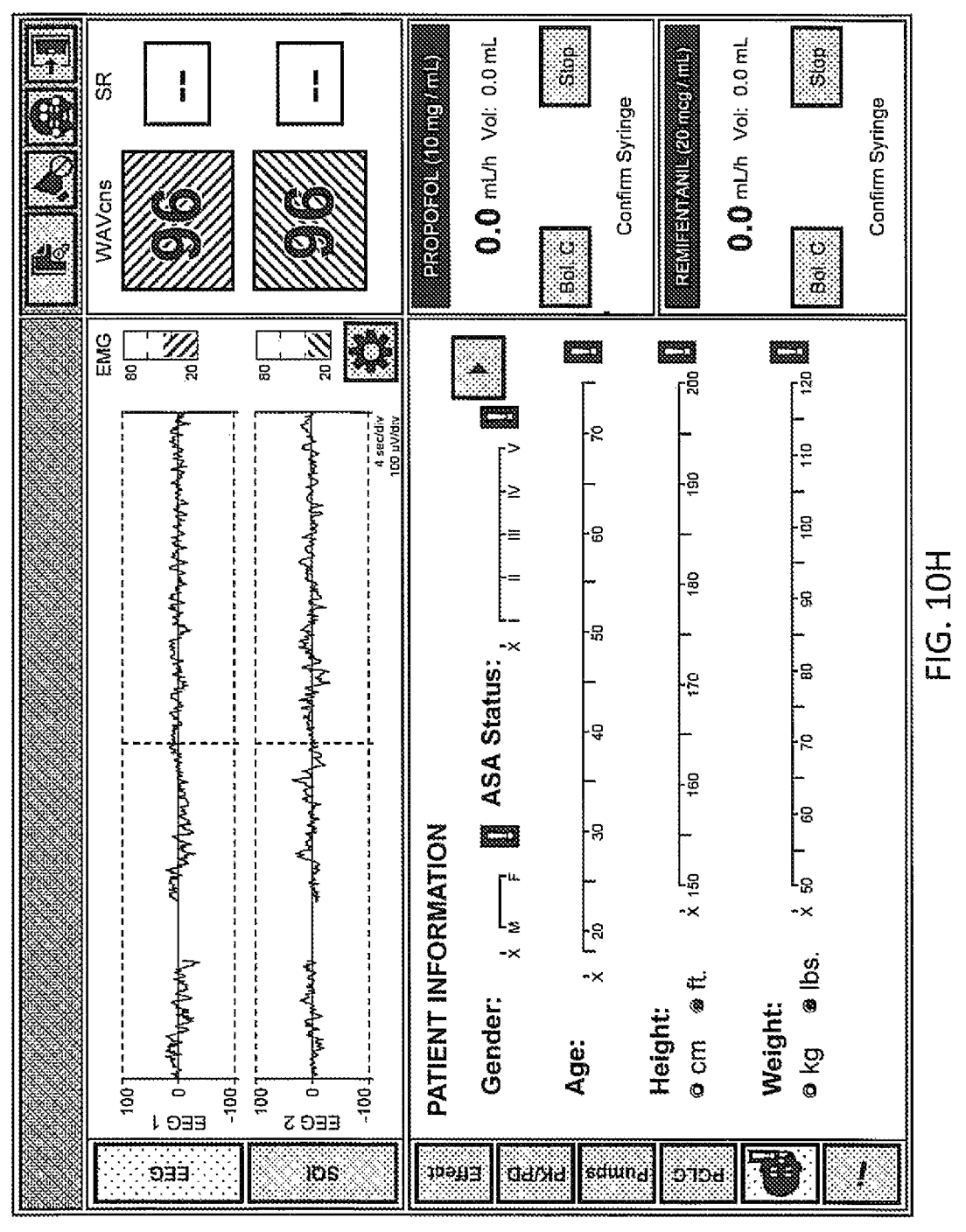

FIGS. 10D, 10E, and 10F show how closed-loop controller settings and drug settings must be entered and confirmed before closed-loop delivery of the drug(s) can begin. FIGS. 10G and 10H show how patient information settings must be entered and confirmed before closed-loop delivery of the drug(s) can begin. In the FIGS. 10C through 10F, "exclamation point" icons mark settings which must be confirmed, or which are otherwise detected as requiring adjustment, before drug delivery can commence.

FIG. 11 is an electrode/display integrated block diagram showing the arrangement of components in the DBM and IMIS of some embodiments of the present invention. EEG signals are collected from an electrode array 1201 having a plurality of electrodes which are printed on, embedded in, etc., a full-flexible or semi-flexible substrate 1220 along with electronic components for RFI filtering and over-voltage protection 1202, amplifying, digitizing, and other signal acquisition tasks 1203, and controlling and/or processing the acquired data 1204. Together all these components form the electrode array 1220 discussed elsewhere in this application. Data from this electrode array is, in some embodiments, wired or wirelessly transmitted over a link 1205 to a monitor 1206 which may further process the data with a processor 1207, store raw and/or processed data in a memory 1208, and output raw and/or processed data to a display 1209. Embodiments that integrate the electrode array and the monitor into one disposable device are called by the term "disposable brain monitor" (DBM) 1230 in this application.

Optionally, the same data link 1205 may be used to also send data from the electrode array 1220 and/or monitor 1206 to an integrated monitoring and infusion system (IMIS) 1210. Here, the raw or processed data is optionally further processed by CPU 1211 which comprises PID controller 1212 for output on a display 1213 and/or control of one or more infusion pumps 1217, 1218, 1219, etc. to deliver drugs to the patient or subject (not shown). The IMIS is controlled by a user interface 1214 which may include a keyboard, mouse, stylus, touchscreen, voice operation, or any other suitable interface. Signals, processed data and/or dosage logs are stored on a memory 1215. Audio feedback, including alarms that indicate dosages and/or patient status such as detected patient consciousness/alertness, may be provided by speaker 1216. As discussed previously, the pumps may be syringe pumps, peristaltic pumps, volumetric pumps, gravity-based pumps, or any other type of pump recognized as preferred for the particular application.

Together, the DBM and IMIS systems form an automated closed-loop sedation or anesthesia system capable of being applied by a person with minimal training, and requiring no continuous human interaction or continuous human presence at the bedside. Preferably, the DBM of the present invention provides that all equipment and functionality of the system is placed directly on the forehead of the patient or subject. The DBM provides at least three EEG electrodes, and preferably at least six EEG electrodes. Preferably, the DBM provides at least two channels of EEG, and more preferably at least four channels.

Figure 12:
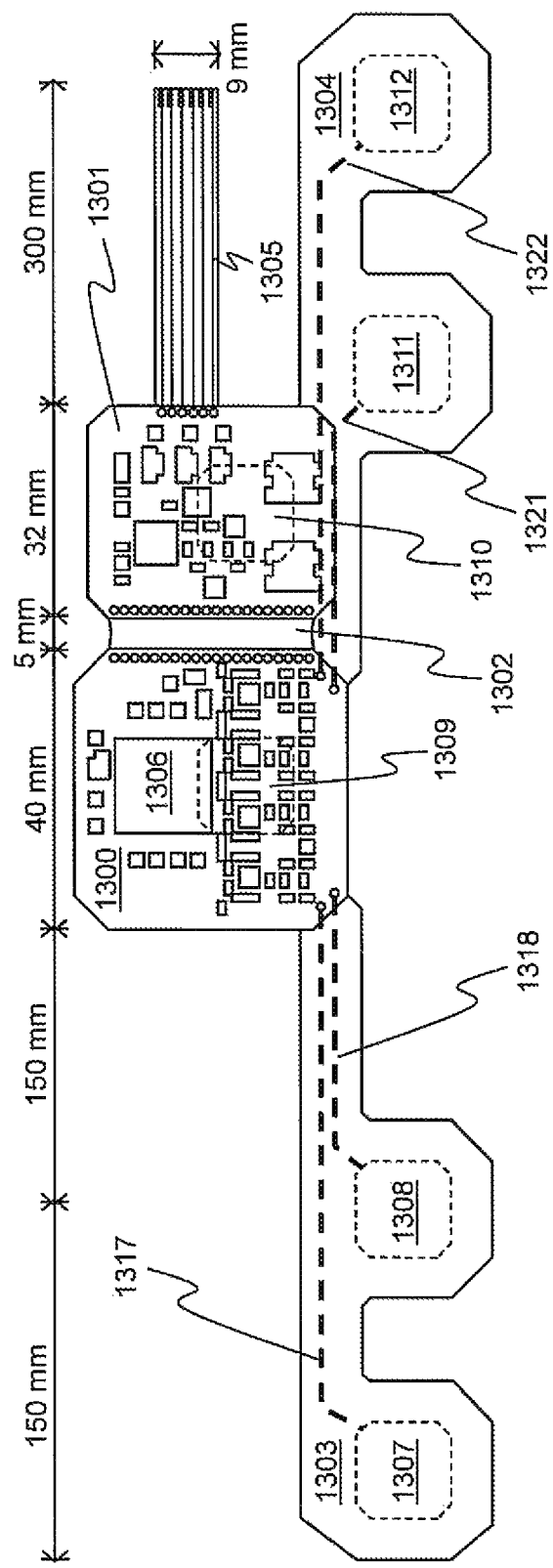
FIG. 12. Electronic schematic of a dual-PCB patch-type electrode array for use in some embodiments.

FIG. 12 illustrates a patch-type electrode array that may be used in some embodiments of the present invention. Two rigid PCBs 1300, 1301 are electrically joined by a flexible PCB bridge 1302. The first rigid PCB 1300, which measures 40 mm by 40 mm, is electrically connected to a left-side flexible PCB 1303 and a right-side flexible PCB 1304, while the second rigid PCB 1301, which measures 32 mm by 40 mm, is electrically connected to a 6-channel flexible PCB data connector 1305 which may be used to connect to a monitor (not shown), components for wireless data transmission (not shown), or to offload stored data following the patch's usage. Traces 1317, 1318, 1321, and 1322 act as embedded electrode leads to carry EEG signals from electrode pads 1307, 1308, 1311, and 1312, respectively—which are silver-plated and are printed on or embedded in the flexible substrates 1303 and 1304—to the first rigid PCB 1300. Two more electrode pads 1309, 1310 are located on the undersides of rigid PCBs 1300, 1301, respectively. The locations of all electrode pads are illustrated with thin broken lines, while the traces to those pads are illustrated with thick broken lines. The rigid PCBs 1300, 1301 have assembled on them electronic components to amplify, filter, digitize, process and/or store the EEG signals collected from the electrode pads. ASIC or IC 1306 is located on the first rigid PCB 1300 to carry out some of these EEG acquisition and processing functions as described above. As discussed above, in some embodiments, this component may be Texas Instruments ADS1299. Other components located on the rigid PCBs include operational amplifiers (e.g., OPA4314), DACs (e.g., DAC101S101), components for filtering radio frequency interference (RFI) or ESU interference, low dropout regulators (e.g., NCP508), voltage inverters (e.g., TPS60400) crystals, microcontrollers (e.g., PIC16F684, PIC18LF26K22), capacitors (e.g., 100 microfarad), and so forth. The scale showing the spacing between electrode pads is illustrated at the top of the FIG. 12 schematic. (The scale shown in FIG. 13 also applies.)

In the particular embodiment shown in FIG. 12, the rigid PCBs preferably comprise four layers, one-ounce copper, silver finished, no blind vias. Preferably, they have a minimum hole size of 0.008", a minimum trace spacing of 0.008", a minimum trace width of 0.008". The flexible PCBs preferably comprise a single layer, one-ounce copper, silver finished, and preferably have a minimum trace spacing of 0.01", a minimum trace width of 0.01", and a minimum trace to edge distance of 0.02". Preferably, the maximum component height on the rigid PCBS is no more than 2 millimeters.

Figure 13:
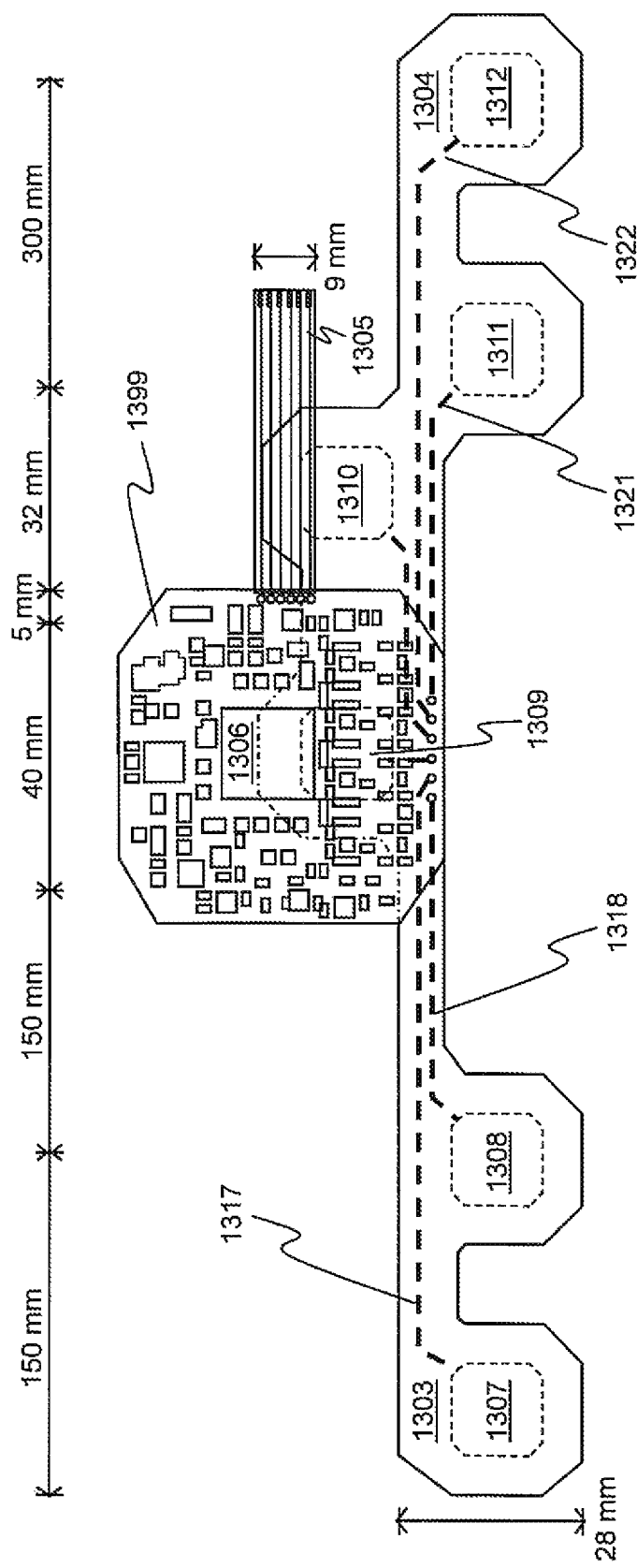
FIG. 13. Electronic schematic of a single-PCB patch-type electrode array for use in some embodiments.

The embodiment shown in FIG. 13 is similar to the one of FIG. 13, but uses a layout that accommodates all necessary electronic components on a single rigid PCB 1399 and thus eliminates the flexible bridge 1302 present in the dual-PCB embodiment of FIG. 12, which can add excessive cost and thus impact the device's disposability.

While a preferred embodiment is disclosed herein, it will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A portable brain monitoring system for determining a level of traumatic brain injury comprising:
   a disposable sensing system comprising an electrode array comprising a flexible substrate and at least two electroencephalogram (EEG) electrodes affixed to or embedded in the flexible adhesive substrate adapted to be applied to a subject's forehead, the at least two electrodes each having a signal, and sensing system electronics comprising at least one sensing system electronic component attached to the flexible substrate or integrated within the electrode array, the at least one sensing system electronic component comprising an input channel for receiving the signals from the at least two electrodes, at least one filter for removing noise or artifacts from the signals, and an output channel for transmitting the filtered signal or data based on the filtered signal;
   a monitoring system comprising monitoring system electronics further comprising at least one monitoring system electronic component, in wired or wireless communication with the sensing system electronics for receiving the transmitted filtered signal, or data based on the filtered signal, and an algorithm for determining a numerical index of the level of traumatic brain injury of the subject based on EEG suppression of the transmitted signal or data, the monitoring system further comprising a display adapted for outputting the index of the level of traumatic brain injury; and
   a therapy system for providing treatment to the subject based on the level of traumatic brain injury of the subject,
   wherein the at least one sensing system electronic component further includes an analog to digital converter adapted for digitizing the filtered signal prior to transmission to the monitoring system.

2. The portable brain monitoring system in claim 1, wherein the flexible substrate further comprises at least one light-emitting diode (LED) adapted to indicate signal quality of the electrodes or proper placement of the electrode array.

3. The portable brain monitoring system in claim 2, wherein the surface area of the flexible substrate of the disposable sensing system is less than 8 square inches.

4. The portable brain monitoring system in claim 1, wherein the portable brain monitoring system is adapted to automatically turn on and begin to perform signal acquisition, processing and analysis upon removal of a thin peelable backing of the flexible substrate and connection to the monitoring system.

5. The portable monitoring system in claim 1, wherein the system operates to detect EEG suppression within 3 minutes of application of the system to the subject's skin or occurrence of the traumatic brain injury.

6. A portable brain monitoring system for determining a level of traumatic brain injury and treating the injury comprising:
   a disposable sensing system comprising
   an electrode array comprising a flexible adhesive substrate and at least two electroencephalogram (EEG) electrodes affixed to or embedded in the flexible substrate, the at least two electrodes each having a signal, the electrode array adapted to be attached to the subject's forehead;
   electrode array electronics comprising at least one electronic component attached to the flexible substrate or integrated within the electrode array, the electrode array electronics comprising an input channel for receiving the signals from the at least two electrodes, at least one filter for removing noise or artifacts from the signals, an analog to digital converter for converting the filtered signals from analog to digital, a processor comprising an algorithm for quantifying at least a portion of the filtered digital signal and an output channel for transmitting the filtered digital signal and/or the quantified at least portion of the filtered digital signal or data based on the filtered digital signal and/or the quantified at least portion of the filtered digital signal;
   a monitoring system comprising monitoring system electronics further comprising at least one monitoring system electronic component, in wired or wireless communication with the electrode array electronics for receiving the transmitted filtered digital signal or data based on the filtered digital signal, and an algorithm for determining the level of traumatic brain injury of the subject based on EEG suppression of the transmitted signal or data, the monitoring system further comprising a display adapted for outputting the level of traumatic brain injury; and
   a therapy system for providing treatment to the subject based on the level of traumatic brain injury of the subject.

7. The portable brain monitoring system in claim 6, wherein the at least one monitoring system electronic component is a processor, which is encapsulated into a cable, which connects the disposable sensing system with the display, and the processor is adapted to calculate with the algorithm the level of traumatic brain injury from the transmitted filtered digital signal or data and output a brain status to the display.

8. The portable brain monitoring system in claim 6, wherein the flexible substrate further comprises at least one light-emitting diode (LED) adapted to indicate signal quality of the electrodes or proper placement of the electrode array.

9. The portable brain monitoring system in claim 6, wherein the portable brain monitoring system is adapted to automatically turn on and begin to perform signal acquisition, processing and analysis upon removal of a thin peelable backing of the flexible substrate and connection to the monitoring system.

10. The portable brain monitoring system in claim 9, wherein the surface area of the flexible substrate of the disposable sensing system is less than 8 square inches.

\* \* \* \* \*